(12) United States Patent
Hayashi et al.

(10) Patent No.: US 10,364,222 B2
(45) Date of Patent: Jul. 30, 2019

(54) CYCLIC AMINE DERIVATIVE AND MEDICAL USE THEREOF

(71) Applicant: Toray Industries, Inc., Tokyo (JP)

(72) Inventors: Shinnosuke Hayashi, Kamakura (JP); Martial Vallet, Kamakura (JP); Shinya Yokosaka, Kamakura (JP); Kazuya Osumi, Kamakura (JP); Takumi Aoki, Tokyo (JP); Hiroyuki Meguro, Kamakura (JP); Mie Kaino, Kamakura (JP); Kozue Takagaki, Kamakura (JP); Takehiro Takahashi, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 16/072,482

(22) PCT Filed: Jan. 27, 2017

(86) PCT No.: PCT/JP2017/002924
§ 371 (c)(1),
(2) Date: Jul. 24, 2018

(87) PCT Pub. No.: WO2017/131156
PCT Pub. Date: Aug. 3, 2017

(65) Prior Publication Data
US 2018/0370916 A1 Dec. 27, 2018

(30) Foreign Application Priority Data

Jan. 29, 2016 (JP) .................................. 2016-015512
Oct. 31, 2016 (JP) .................................. 2016-212629

(51) Int. Cl.
| C07D 211/60 | (2006.01) |
| C07D 211/36 | (2006.01) |
| C07D 211/38 | (2006.01) |
| C07D 211/44 | (2006.01) |
| C07D 211/96 | (2006.01) |
| C07D 401/06 | (2006.01) |
| C07D 405/06 | (2006.01) |
| C07D 413/06 | (2006.01) |
| A61K 31/451 | (2006.01) |
| A61K 31/454 | (2006.01) |
| A61P 17/06 | (2006.01) |
| A61P 37/06 | (2006.01) |
| A61P 25/00 | (2006.01) |

(52) U.S. Cl.
CPC .......... C07D 211/60 (2013.01); A61K 31/451 (2013.01); A61K 31/454 (2013.01); A61P 17/06 (2018.01); A61P 25/00 (2018.01); A61P 37/06 (2018.01); C07D 211/36 (2013.01); C07D 211/38 (2013.01); C07D 211/44 (2013.01); C07D 211/96 (2013.01); C07D 401/06 (2013.01); C07D 405/06 (2013.01); C07D 413/06 (2013.01)

(58) Field of Classification Search
CPC ... C07D 211/60; C07D 211/36; C07D 211/38; C07D 211/44; C07D 211/96; C07D 401/06; C07D 405/06; C07D 413/06; A61K 31/451; A61K 31/454
See application file for complete search history.

(56) References Cited

U.S. PATENT DOCUMENTS

| 2008/0113961 | A1 | 5/2008 | Nishi et al. |
| 2012/0322837 | A1 | 12/2012 | Maeba et al. |
| 2014/0296306 | A1 | 10/2014 | Maeba et al. |
| 2015/0065507 | A1 | 3/2015 | Birault et al. |
| 2015/0175562 | A1 | 6/2015 | Gege et al. |
| 2016/0346256 | A1 | 12/2016 | Maeba et al. |

FOREIGN PATENT DOCUMENTS

| JP | 2012-236822 A | 12/2012 |
| JP | 2015-514794 A | 5/2015 |
| JP | 2015-521193 A | 7/2015 |
| RU | 2382781 C2 | 2/2010 |
| WO | 2006/129199 A1 | 12/2006 |
| WO | 2010/007046 A2 | 1/2010 |
| WO | 2010/096371 A2 | 8/2010 |

(Continued)

OTHER PUBLICATIONS

Chen, Z. et al., "FOXP3 and RORγt: Transcriptional regulation of Treg and Th17," *International Immunopharmacology*, 2011, vol. 11, pp. 536-542.

(Continued)

*Primary Examiner* — Timothy R Rozof
(74) *Attorney, Agent, or Firm* — DLA Piper LLP (US)

(57) ABSTRACT

A compound has retinoid-related orphan receptor γ antagonist activity and shows a therapeutic effect or a preventive effect on autoimmune diseases such as multiple sclerosis or psoriasis or allergic diseases, including allergic dermatitis or the like, such as contact dermatitis or atopic dermatitis. The cyclic amine derivative is represented by the formula or a pharmacologically acceptable salt thereof.

11 Claims, 12 Drawing Sheets

(56) References Cited

FOREIGN PATENT DOCUMENTS

| WO | 2012/027965 A1 | 3/2012 |
| WO | 2015/103507 A1 | 7/2015 |
| WO | 2015/103508 A1 | 7/2015 |

OTHER PUBLICATIONS

Hofmann, M. A. et al., "A systematic review of the role of interleukin-17 and the interleukin-20 family in inflammatory allergic skin diseases," *Current Opinion in Allergy and Clinical Immunology*, 2016, vol. 16, pp. 451-457.

Ivanov, I. L. et al., "The Orphan Nuclear Receptor RORγt Directs the Differentiation Program of Proinflammatoly IL-17$^+$ T Helper Cells," *Cell*, 2006, vol. 126, pp. 1121-1133.

Jetten, A. M., "Retinoid-related orphan receptors (RORs): critical roles in development, immunity, circadian rhythm, and cellular metabolism," *Nuclear Receptor Signaling*, 2009, vol. 7, e003, pp. 1-32.

Hamzaoui, K. et al., "Expression of Th-17 and RORγt mRNA in Behçet's Disease," *Medical Science Monitor*, 2011, vol. 17, pp. CR227-CR234.

Ma, L. et al., "The Imbalance of Th17 cells and CD4$^+$ CD25$^{high}$Foxp3$^+$ Treg cells in patients with atopic dermatitis," *Journal of the European Academy of Dermatology and Venereology*, 2014, vol. 28, pp. 1079-1086.

Zhao, Y. et al., "Th-17/Tc-17 infiltration and associated cytokine gene expression in elicitation phase of allergic contact dermatitis," *British Journal of Dermatology*, 2009, vol. 161, pp. 1301-1306.

Leppkes, M. et al., "RORγ-Expressing Th17 Cells Induce Murine Chronic Intestinal Inflammation via Redundant Effects of IL-17A and IL-17F," *Gastroenterology*, 2009, vol. 136, pp. 257-267.

Tilley, S. L. et al., "Retinoid-Related Orphan Receptor γ Controls Immunoglobulin Production and Th1/Th2 Cytokine Balance in the Adaptive Immune Response to Allergen," *The Journal of Immunology*, 2007, vol. 178, pp. 3208-3218.

Jin, L. et al., "Structural Basis for Hydroxycholesterols as Natural Ligands of Orphan Nuclear Receptor RORγ," *Molecular Endocrinology*, 2010, vol. 24. pp. 923-929.

Solt, L. A. et al., "Suppression of $T_H17$ differentiation and autoimmunity by a synthetic ROR ligand," *Nature*, 2011, vol. 472, pp. 491-494.

Fauber, B. P. et al., "Discovery of 1-{4-[3-Fluoro-4-((3S,6R)-3-methyl-1,1-dioxo-6-phenyl-[1,2]thiazinan-2-ylmethyl)-phenyl]-piperazin-1-yl}-ethanone (GNE-3500): a Potent, Selective, and Orally Bioavailable Retinoic Acid Receptor-Related Orphan Receptor C (RORc or RORγ) Inverse Agonist," *Journal of Medicinal Chemistry*, 2015, vol. 58, pp. 5308-5322, Abstract only.

Office Action dated Feb. 28, 2019, of counterpart Russian Patent Application No. 2018126968, along with an English translation.

CYCLIC AMINE DERIVATIVE AND MEDICAL USE THEREOF

TECHNICAL FIELD

This disclosure relates to a cyclic amine derivative and medical use thereof.

BACKGROUND

An autoimmune disease is a general term for diseases in which excessive immune responses attack an individual's own normal cells and tissues, resulting in symptoms, and examples thereof include multiple sclerosis, psoriasis, rheumatoid arthritis, systemic lupus erythematosus, ankylosing spondylitis, uveitis, or polymyalgia rheumatica.

An allergic disease is a disease derived from excessive immune responses to specific antigens, and examples thereof include allergic dermatitis, atopic dermatitis, allergic rhinitis (pollinosis), allergic conjunctivitis, allergic gastroenteritis, bronchial asthma, childhood asthma, or food allergy.

Various mechanisms have been proposed for the onset and progress of autoimmune diseases and allergic diseases. As one of these mechanisms, it is known that Th17 cells, which is one of a subset of helper T cells, and IL-17, which is an inflammatory cytokine produced by Th17 cells, play an important role in the onset and progress of autoimmune diseases and allergic diseases (Chen et al., International Immunopharmacology, 2011, Vol. 11, p. 536-542 and Hofmann et al., Current Opinion in Allergy and Clinical Immunology, 2016, Vol. 16, p. 451-457).

IL-17 acts on various cells such as fibroblasts, epithelial cells, vascular endothelial cells, and macrophages, and is involved in the induction of inflammatory cytokines, chemokines, metalloproteases and other inflammatory mediators and the migration of neutrophils. Therefore, it is considered that potent anti-inflammatory effects are shown if the production or function of IL-17 can be suppressed, and clinical studies of anti-IL-17 antibodies with indications for various autoimmune diseases have been conducted.

Recently, it became clear that retinoid-related orphan receptor γ (hereinafter referred to as RORγ), which is a nuclear receptor, functions as a transcription factor essential for the differentiation and proliferation of Th17 cells and the expression of IL-17 (Ivanov et al., Cell, 2006, Vol. 126, p. 1121-1133), and it was shown that suppression of the expression or function of RORγ results in suppression of the differentiation and activation of Th17 cells and the production of IL-17 (Jetten, Nuclear Receptor Signaling, 2009, Vol. 7, e003).

It has been reported that the expression level of RORγ in peripheral blood mononuclear cells or skin tissue in patients with autoimmune diseases (multiple sclerosis, psoriasis, systemic lupus erythematosus and the like) or patients with allergic diseases (allergic dermatitis and the like) is higher than that of healthy individuals (Hamzaoui et al., Medical Science Monitor, 2011, Vol. 17, p. CR227-234, Ma et al., Journal of the European Academy of Dermatology and Venereology, 2014, Vol. 28, p. 1079-1086 and Zhao et al., British Journal of Dermatology, 2009, Vol. 161, p. 1301-1306). It has been reported that, in a knockout mouse of RORγ, the pathological state of a mouse experimental autoimmune encephalomyelitis model, which is an animal model of multiple sclerosis, is suppressed and that symptoms of autoimmune diseases such as colitis, and symptoms of allergic diseases such as asthma, are suppressed (Ivanov et al., Cell, 2006, Vol. 126, p. 1121-1133, Leppkes et al., Gastroenterology, 2009, Vol. 136, p. 257-267 and Jetten et al., The Journal of Immunology, 2007, Vol. 178, p. 3208-3218).

Furthermore, it has been suggested that binding between RORγ and a coactivator is necessary for RORγ to function as a transcription factor (Li et al., Molecular Endocrinology, 2010, Vol. 24. p. 923-929). Therefore, an RORγ antagonist, which is a compound that inhibits the binding between RORγ and a coactivator, is expected to be useful as a therapeutic agent or preventive agent for autoimmune diseases or allergic diseases.

On the other hand, as the RORγ antagonist, N-(5-(N-(4-(1,1,1,3,3,3-hexafluoro-2-hydroxypropan-2-yl)phenyl)sulfamoyl)-4-methylthiazol-2-yl)acetamide (Burris et al., Nature, 2011, Vol. 472, p. 491-494), substituted azole derivatives (JP 2012-236822 A) such as 6-(2-chloro-4-methylphenyl)-3-(4-cyclopropyl-5-(3-neopentylcyclobutyl)isoxazol-3-yl)-5-oxohexanoic acid, and sulfonylbenzene derivatives (WO 2012/027965) such as N-(5-(2-chlorobenzoyl)-4-(3-chlorophenyl)thiazol-2-yl)-2-(4-(ethylsulfonyl)phenyl)acetamide have been reported previously, but compounds having a cyclic amine structure such as 1-substituted piperidine-2-carboxamide, have not been disclosed.

As the compound having a cyclic amine structure such as 1-substituted piperidine-2-carboxamide, (S)-1-(2-(3,3-difluoropyrrolidin-1-yl)acetyl)-N-(1-ethyl-5-phenyl-1H-1,2,4-triazol-3-yl)piperidine-2-carboxamide and the like has been reported as a cannabinoid 2 receptor agonist (WO 2010/096371), and (R)-N-(5-benzyl-4-phenylthiazol-2-yl)-1-(2-cyclopentylacetyl)piperidine-2-carboxamide and the like has been reported as an acyl-coenzyme A: diacylglycerol acyltransferase 1 inhibitor (WO 2010/007046), but the effects of these compounds on RORγ have been neither disclosed nor suggested.

As the therapeutic agent or preventive agent for multiple sclerosis, (S)-(3-(5-(4-fluorobenzyl)-1,2,4-oxadiazol-3-yl)piperidin-1-yl)(4-fluorophenyl)methanone and the like has been reported as a positive allosteric modulator of a metabotropic glutamate receptor (WO 2006/129199), but concrete data on the drug efficacy of these compounds on multiple sclerosis have not been shown at all, and the usefulness has not been shown at all. In WO 2006/129199, the effects of these compounds on RORγ have been neither disclosed nor suggested, and compounds having a 1-substituted piperidine-2-carboxamide structure have not been disclosed.

For the actual treatment of autoimmune diseases and allergic diseases, steroids or immunosuppressive agents acting on the whole immune system are used as internal medicines. However, due to concerns about serious side effects such as infection, currently there are many clinical cases in which administration must be discontinued before sufficient drug efficacy is obtained. Therefore, there is a need to develop a new medicament targeted to a molecule playing an important role in the mechanism of the onset and progress of autoimmune diseases and allergic diseases.

Therefore, it could be helpful to provide a novel compound having RORγ antagonist activity and a therapeutic agent or preventive agent for an autoimmune disease or allergic disease based on the effect to suppress the function of RORγ by RORγ antagonist activity.

SUMMARY

We thus provide:
A cyclic amine derivative represented by formula (I)

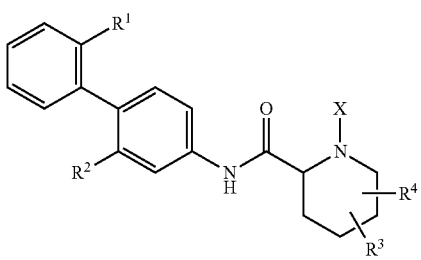

wherein
$R^1$ represents an alkyloxy group having 1 to 3 carbon atoms, any 1 to 3 hydrogen atoms of which are optionally substituted with a halogen atom(s);
$R^2$ represents a halogen atom;
$R^3$ represents a hydrogen atom, a halogen atom, or a hydroxy group;
$R^4$ represents a hydrogen atom or a halogen atom;
X represents —C(=O)—(CH$_2$)$_n$—R$^5$ or —S(=O)$_2$—R$^6$;
n is an integer of 0 to 5;
$R^5$ represents a hydrogen atom, —OR$^7$, —SR$^7$, —S(=O)$_2$—R$^7$, —C(=O)—OR$^7$, —N(R$^7$)R$^8$, an alkyl group having 1 to 3 carbon atoms, any 1 to 3 hydrogen atoms of which are optionally substituted with a halogen atom(s), or a heteroaryl group, any hydrogen atom(s) of which is/are optionally substituted with an alkyl group(s) having 1 to 3 carbon atoms;
$R^6$ represents an alkyl group having 1 to 5 carbon atoms;
$R^7$ represents a hydrogen atom or an alkyl group having 1 to 3 carbon atoms, any 1 to 3 hydrogen atoms of which are optionally substituted with a halogen atom(s); and
$R^8$ represents a hydrogen atom, an alkyl group having 1 to 3 carbon atoms, an acyl group having 2 to 4 carbon atoms, or an alkylsulfonyl group having 1 to 3 carbon atoms,
or a pharmacologically acceptable salt thereof.

In the cyclic amine derivative represented by formula (I) above, it is preferable that $R^1$ is an alkyloxy group having 1 to 3 carbon atoms, any 1 to 3 hydrogen atoms of which are optionally substituted with a fluorine atom(s) or a chlorine atom(s), $R^2$ is a fluorine atom or a chlorine atom, $R^3$ is a hydrogen atom, a fluorine atom, a chlorine atom, or a hydroxy group, $R^4$ is a hydrogen atom, a fluorine atom, or a chlorine atom, $R^5$ is a hydrogen atom, —OR$^7$, —SR$^7$, —S(=O)$_2$—R$^7$, —C(=O)—OR$^7$, —N(R$^7$)R$^8$, an alkyl group having 1 to 3 carbon atoms, any 1 to 3 hydrogen atoms of which are optionally substituted with a fluorine atom(s) or a chlorine atom(s), or a heteroaryl group, any hydrogen atom(s) of which is/are optionally substituted with a methyl group(s), $R^6$ is an alkyl group having 1 to 3 carbon atoms, and $R^7$ is a hydrogen atom or an alkyl group having 1 to 3 carbon atoms, any 1 to 3 hydrogen atoms of which are optionally substituted with a fluorine atom(s) or a chlorine atom(s).

In this case, higher RORγ antagonist activity can be expected.

In the cyclic amine derivative represented by formula (I) above, it is more preferable that $R^1$ is a methoxy group, any 1 to 3 hydrogen atoms of which are optionally substituted with a fluorine atom(s), $R^2$ is a fluorine atom or a chlorine atom, $R^3$ is a hydrogen atom, a fluorine atom, or a hydroxy group, $R^4$ is a hydrogen atom or a fluorine atom, n is an integer of 0 to 4, $R^5$ is a hydrogen atom, —OR$^7$, —N(R$^7$)R$^8$, an alkyl group having 1 to 3 carbon atoms, any 1 to 3 hydrogen atoms of which are optionally substituted with a fluorine atom(s), or a 5-membered ring heteroaryl group, any hydrogen atom(s) of which is/are optionally substituted with a methyl group(s), $R^6$ is a methyl group or an ethyl group, $R^7$ is a hydrogen atom or an alkyl group having 1 to 3 carbon atoms, any 1 to 3 hydrogen atoms of which are optionally substituted with a fluorine atom(s), and $R^8$ is a hydrogen atom, a methyl group, an acyl group having 2 to 4 carbon atoms, or an alkylsulfonyl group having 1 to 3 carbon atoms.

In this case, higher RORγ antagonist activity can be expected and, furthermore, an excellent therapeutic effect or preventive effect in autoimmune diseases such as multiple sclerosis or psoriasis, or allergic diseases such as allergic dermatitis, can be expected.

In the cyclic amine derivative represented by formula (I) above, it is still more preferable that $R^1$ is a trifluoromethoxy group, $R^2$ is a chlorine atom, $R^3$ is a hydrogen atom, $R^4$ is a hydrogen atom, X is —C(=O)—(CH$_2$)$_n$—R$^5$, n is an integer of 0 to 3, $R^5$ is a methyl group, a trifluoromethyl group, —N(R$^7$)R$^8$, or an imidazolyl, triazolyl, or tetrazolyl group, any hydrogen atom(s) of which is/are optionally substituted with a methyl group(s), $R^7$ is a hydrogen atom, a methyl group, or an ethyl group, and $R^8$ is a hydrogen atom, a methyl group, an acetyl group, a propionyl group, a methylsulfonyl group, or an ethylsulfonyl group.

In this case, higher RORγ antagonist activity can be expected and, furthermore, an excellent therapeutic effect or preventive effect in autoimmune diseases such as multiple sclerosis or psoriasis, or allergic diseases such as allergic dermatitis, can be expected.

We provide a medicament and an RORγ antagonist, each of which contains the cyclic amine derivative represented by formula (I) above or a pharmacologically acceptable salt thereof as an active ingredient.

The abovementioned medicament is preferably a therapeutic agent or preventive agent for an autoimmune disease or an allergic disease, more preferably a therapeutic agent or preventive agent for multiple sclerosis or psoriasis as the abovementioned therapeutic agent or preventive agent for an autoimmune disease, more preferably a therapeutic agent or preventive agent for allergic dermatitis as the abovementioned therapeutic agent or preventive agent for an allergic disease, and more preferably a therapeutic agent or preventive agent for contact dermatitis or atopic dermatitis as the abovementioned therapeutic agent or preventive agent for allergic dermatitis.

Since the cyclic amine derivative or a pharmacologically acceptable salt thereof has RORγ antagonist activity, it can effectively suppress the function of RORγ and can be used as a therapeutic agent or preventive agent for autoimmune diseases or allergic diseases.

DETAILED DESCRIPTION

Figure 1:
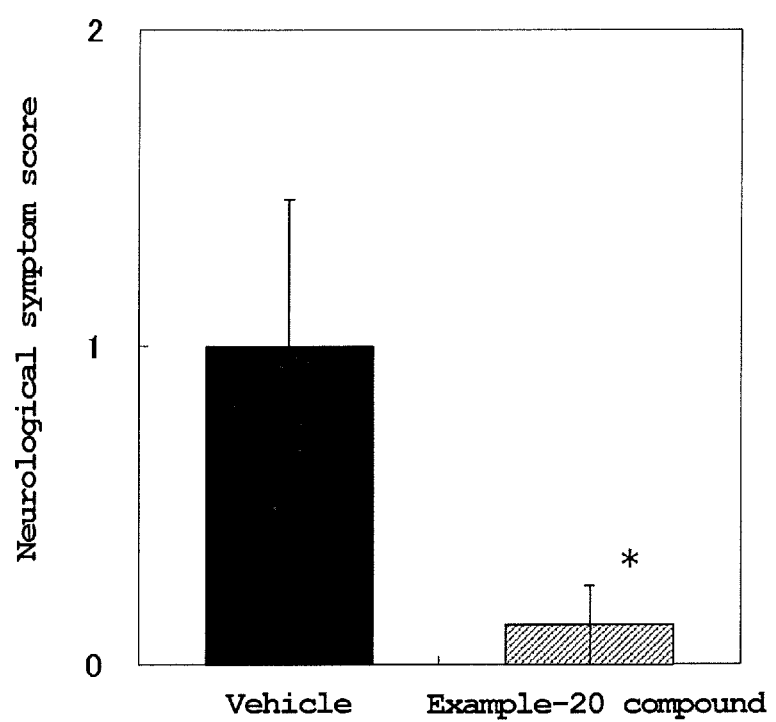
FIG. 1 is a graph showing the suppressive effect of the compound of Example 20 on the increase in the neurological symptom score in a mouse experimental autoimmune encephalomyelitis model.

The cyclic amine derivative is characterized by being represented by formula (I)

wherein $R^1$ represents an alkyloxy group having 1 to 3 carbon atoms, any 1 to 3 hydrogen atoms of which are optionally substituted with a halogen atom(s);

$R^2$ represents a halogen atom;

$R^3$ represents a hydrogen atom, a halogen atom, or a hydroxy group;

$R^4$ represents a hydrogen atom or a halogen atom;

X represents —C(=O)—(CH$_2$)$_n$—R$^5$ or —S(=O)$_2$—R$^6$;

n represents an integer of 0 to 5;

$R^5$ represents a hydrogen atom, —OR$^7$, —SR$^7$, —S(=O)$_2$—R$^7$, —C(=O)—OR$^7$, —N(R$^7$)R$^8$, an alkyl group having 1 to 3 carbon atoms, any 1 to 3 hydrogen atoms of which are optionally substituted with a halogen atom(s), or a heteroaryl group, any hydrogen atom(s) of which is/are optionally substituted with an alkyl group having 1 to 3 carbon atoms;

$R^6$ represents an alkyl group having 1 to 5 carbon atoms;

$R^7$ represents a hydrogen atom or an alkyl group having 1 to 3 carbon atoms, any 1 to 3 hydrogen atoms of which are optionally substituted with a halogen atom(s); and $R^8$ represents a hydrogen atom, an alkyl group having 1 to 3 carbon atoms, an acyl group having 2 to 4 carbon atoms, or an alkylsulfonyl group having 1 to 3 carbon atoms.

The following terms used herein are defined as follows, unless otherwise specified.

The term "alkyl group having 1 to 3 carbon atoms" means a methyl group, an ethyl group, a propyl group, or an isopropyl group.

The term "alkyl group having 1 to 5 carbon atoms" means a linear saturated hydrocarbon group having 1 to 5 carbon atoms or a branched saturated hydrocarbon group having 3 to 5 carbon atoms, and examples thereof include a methyl group, an ethyl group, a propyl group, an isopropyl group, a butyl group, an isobutyl group, a sec-butyl group, a tert-butyl group, a pentyl group, an isopentyl group, a neopentyl group, or a tert-pentyl group.

The term "alkyloxy group having 1 to 3 carbon atoms" means a methoxy group, an ethoxy group, a propyloxy group, or an isopropyloxy group.

The term "acyl group having 2 to 4 carbon atoms" means an acetyl group, a propionyl group, a butanoyl group, or a 2-methylpropanoyl group.

The term "alkylsulfonyl group having 1 to 3 carbon atoms" means a methylsulfonyl group, an ethylsulfonyl group, a propylsulfonyl group, or an isopropylsulfonyl group.

The term "heteroaryl group" means a heterocyclic aromatic group containing 1 to 4 hetero atoms independently selected from the group consisting of a nitrogen atom, an oxygen atom, and a sulfur atom, and examples thereof include a thienyl group, a pyrrolyl group, a furyl group, a thiazolyl group, an imidazolyl group, an oxazolyl group, a pyrazolyl group, an isothiazolyl group, an isoxazolyl group, a triazolyl group, an oxadiazolyl group, a tetrazolyl group, a pyridyl group, a pyridazinyl group, a pyrimidinyl group, a pyrazinyl group, or a triazinyl group.

The term "5-membered ring heteroaryl group" means a heterocyclic aromatic group having 5 ring-constituting atoms containing 1 to 4 hetero atoms independently selected from the group consisting of a nitrogen atom, an oxygen atom, and a sulfur atom, and examples thereof include a thienyl group, a pyrrolyl group, a furyl group, a thiazolyl group, an imidazolyl group, an oxazolyl group, a pyrazolyl group, an isothiazolyl group, an isoxazolyl group, a triazolyl group, an oxadiazolyl, or a tetrazolyl group.

The term "halogen atom" means a fluorine atom, a chlorine atom, a bromine atom, or an iodine atom.

The term "alkyl group having 1 to 3 carbon atoms, any 1 to 3 hydrogen atoms of which are optionally substituted with a halogen atom(s)" means an alkyl group having 1 to 3 carbon atoms as defined above, any 1 to 3 hydrogen atoms of which may be each independently substituted with a halogen atom as defined above, and examples thereof include a methyl group, an ethyl group, a propyl group, an isopropyl group, a fluoromethyl group, a difluoromethyl group, a trifluoromethyl, a 2-fluoroethyl group, a trifluoroethyl group, a trichloromethyl group, or a trichloroethyl group.

The term "alkyl group having 1 to 3 carbon atoms, any 1 to 3 hydrogen atoms of which are optionally substituted with a fluorine atom(s) or a chlorine atom(s)" means an alkyl group having 1 to 3 carbon atoms as defined above, any 1 to 3 hydrogen atoms of which may be each independently substituted with a fluorine atom or a chlorine atom, and examples thereof include a methyl group, an ethyl group, a propyl group, an isopropyl group, a fluoromethyl group, a difluoromethyl group, a trifluoromethyl group, a 2-fluoroethyl group, a trifluoroethyl group, a trichloromethyl group, or a trichloroethyl group.

The term "alkyl group having 1 to 3 carbon atoms, any 1 to 3 hydrogen atoms of which are optionally substituted with a fluorine atom(s)" means an alkyl group having 1 to 3 carbon atoms as defined above, any 1 to 3 hydrogen atoms of which may be substituted with a fluorine atom(s), and examples thereof include a methyl group, an ethyl group, a propyl group, an isopropyl group, a fluoromethyl group, a difluoromethyl group, a trifluoromethyl group, a 2-fluoroethyl group, or a trifluoroethyl group.

The term "alkyloxy group having 1 to 3 carbon atoms, any 1 to 3 hydrogen atoms of which are optionally substituted with a halogen atom(s)" means an alkyloxy group having 1 to 3 carbon atoms as defined above, any 1 to 3 hydrogen atoms of which may be each independently substituted with a halogen atom as defined above, and examples thereof include a methoxy group, an ethoxy group, a propyloxy group, an isopropyloxy group, a fluoromethoxy group, a difluoromethoxy group, a trifluoromethoxy group, a 2-fluoroethoxy group, a trifluoroethoxy group, a trichloromethoxy group, or a trichloroethoxy group.

The term "alkyloxy group having 1 to 3 carbon atoms, any 1 to 3 hydrogen atoms of which are optionally substituted with a fluorine atom(s) or a chlorine atom(s)" means an alkyloxy group having 1 to 3 carbon atoms as defined above, any 1 to 3 hydrogen atoms of which may be each independently substituted with a fluorine atom or a chlorine atom, and examples thereof include a methoxy group, an ethoxy group, a propyloxy group, an isopropyloxy group, a fluoromethoxy group, a difluoromethoxy group, a trifluoromethoxy group, a 2-fluoroethoxy group, a trifluoroethoxy group, a trichloromethoxy group, or a trichloroethoxy group.

The term "methoxy group, any 1 to 3 hydrogen atoms of which are optionally substituted with a fluorine atom(s)" means a methoxy group, a fluoromethoxy group, a difluoromethoxy group, or a trifluoromethoxy group.

The term "heteroaryl group, any hydrogen atom(s) of which is/are optionally substituted with an alkyl group(s) having 1 to 3 carbon atoms" means a heteroaryl group as defined above, any hydrogen atom(s) of which may be each independently substituted with an alkyl group having 1 to 3 carbon atoms as defined above, and examples thereof include a thienyl group, a pyrrolyl group, a furyl group, a thiazolyl group, an imidazolyl group, an oxazolyl group, a pyrazolyl group, an isothiazolyl group, an isoxazolyl group, a triazolyl group, an oxadiazolyl group, a tetrazolyl group, a pyridyl group, a pyridazinyl group, a pyrimidinyl group, a pyrazinyl group, a triazinyl group, a methylthienyl group, a dimethylthienyl group, an ethylthienyl group, a methylpyrrolyl group, a dimethylpyrrolyl group, an ethylpyrrolyl group, a methylfuryl group, a dimethylfuryl group, an ethylfuryl group, a methylthiazolyl group, a dimethylthiazolyl group, an ethylthiazolyl group, a methylimidazolyl group, a dimethylimidazolyl group, an ethylimidazolyl group, a methyloxazolyl group, a dimethyloxazolyl group, an ethyloxazolyl group, a methylpyrazolyl group, a dimethylpyrazolyl group, an ethylpyrazolyl group, a methylisothiazolyl group, a dimethylisothiazolyl group, an ethylisothiazolyl group, a methylisoxazolyl group, a dimethylisoxazolyl group, an ethylisoxazolyl group, a methyltriazolyl group, a dimethyltriazolyl group, an ethyltriazolyl group, a methyloxadiazolyl group, a dimethyloxadiazolyl group, an ethyloxadiazolyl group, a methyltetrazolyl group, an ethyltetrazolyl group, a methylpyridyl group, a dimethylpyridyl group, an ethylpyridyl group, a methylpyridazinyl group, a dimethylpyridazinyl group, an ethylpyridazinyl group, a methylpyrimidinyl group, a dimethylpyrimidinyl group, an ethylpyrimidinyl group, a methylpyrazinyl group, a dimethylpyrazinyl group, an ethylpyrazinyl group, a methyltriazinyl group, a dimethyltriazinyl group, or an ethyltriazinyl group.

The term "heteroaryl group, any hydrogen atom(s) of which is/are optionally substituted with a methyl group(s)" means a heteroaryl group as defined above, any hydrogen atom(s) of which may be each independently substituted with a methyl group, and examples thereof include a thienyl group, a pyrrolyl group, a furyl group, a thiazolyl group, an imidazolyl group, an oxazolyl group, a pyrazolyl group, an isothiazolyl group, an isoxazolyl group, a triazolyl group, an oxadiazolyl group, a tetrazolyl group, a pyridyl group, a pyridazinyl group, a pyrimidinyl group, a pyrazinyl group, a triazinyl group, a methylthienyl group, a dimethylthienyl group, a methylpyrrolyl group, a dimethylpyrrolyl group, a methylfuryl group, a dimethylfuryl group, a methylthiazolyl group, a dimethylthiazolyl group, a methylimidazolyl group, dimethylimidazolyl group, a methyloxazolyl group, a dimethyloxazolyl group, a methylpyrazolyl group, a dimethylpyrazolyl group, a methylisothiazolyl group, a dimethylisothiazolyl group, a methylisoxazolyl group, a dimethylisoxazolyl group, a methyltriazolyl group, dimethyltriazolyl group, a methyloxadiazolyl group, a dimethyloxadiazolyl group, a methyltetrazolyl group, a methylpyridyl group, a dimethylpyridyl group, a methylpyridazinyl group, a dimethylpyridazinyl group, a methylpyrimidinyl group, a dimethylpyrimidinyl group, a methylpyrazinyl group, a dimethylpyrazinyl group, a methyltriazinyl group, or a dimethyltriazinyl group.

The term "5-membered ring heteroaryl group, any hydrogen atom(s) of which is/are optionally substituted with a methyl group(s)" means a 5-membered ring heteroaryl group as defined above, any hydrogen atom(s) of which may be each independently substituted with a methyl group, and examples thereof include a thienyl group, a pyrrolyl group, a furyl group, a thiazolyl group, an imidazolyl group, an oxazolyl group, a pyrazolyl group, an isothiazolyl group, an isoxazolyl group, a triazolyl group, an oxadiazolyl group, a tetrazolyl group, a methylthienyl group, a dimethylthienyl group, a methylpyrrolyl group, a dimethylpyrrolyl group, a methylfuryl group, a dimethylfuryl group, a methylthiazolyl group, a dimethylthiazolyl group, a methylimidazolyl group, a dimethylimidazolyl group, a methyloxazolyl group, a dimethyloxazolyl group, a methylpyrazolyl group, a dimethylpyrazolyl group, a methylisothiazolyl group, a dimethylisothiazolyl group, a methylisoxazolyl group, a dimethylisoxazolyl group, a methyltriazolyl group, dimethyltriazolyl group, a methyloxadiazolyl group, a dimethyloxadiazolyl group, or a methyltetrazolyl group.

Regarding the abovementioned cyclic amine derivative, in formula (I), $R^1$ is preferably an alkyloxy group having 1 to 3 carbon atoms, any 1 to 3 hydrogen atoms of which are optionally substituted with a fluorine atom(s) or a chlorine atom(s), more preferably a methoxy group, any 1 to 3 hydrogen atoms of which are optionally substituted with a fluorine atom(s), and still more preferably a trifluoromethoxy group.

R² is preferably a fluorine atom or a chlorine atom, and more preferably a chlorine atom.

R³ is preferably a hydrogen atom, a fluorine atom, a chlorine atom, or a hydroxy group, more preferably a hydrogen atom, a fluorine atom, or a hydroxy group, and still more preferably a hydrogen atom.

R⁴ is preferably a hydrogen atom, a fluorine atom, or a chlorine atom, more preferably a hydrogen atom or a fluorine atom, and still more preferably a hydrogen atom.

X is preferably —C(=O)—(CH$_2$)$_n$—R⁵.

n is preferably an integer of 0 to 4, and more preferably an integer of 0 to 3.

R⁵ is preferably a hydrogen atom, —OR⁷, —SR⁷, —S(=O)$_2$—R⁷, —C(=O)—OR⁷, —N(R⁷)R⁸, an alkyl group having 1 to 3 carbon atoms, any 1 to 3 hydrogen atoms of which are optionally substituted with a fluorine atom(s) or a chlorine atom(s), or a heteroaryl group, any hydrogen atom(s) of which is/are optionally substituted with a methyl group(s), more preferably a hydrogen atom, —OR⁷, —N(R⁷)R⁸, an alkyl group having 1 to 3 carbon atoms, any 1 to 3 hydrogen atoms of which are optionally substituted with a fluorine atom(s), or a 5-membered ring heteroaryl group, any hydrogen atom(s) of which is/are optionally substituted with a methyl group(s), and still more preferably a methyl group, a trifluoromethyl group, —N(R⁷)R⁸, or an imidazolyl, triazolyl, or tetrazolyl group, any hydrogen atom(s) of which is/are optionally substituted with a methyl group(s).

R⁶ is preferably an alkyl group having 1 to 3 carbon atoms, and more preferably a methyl group or an ethyl group.

R⁷ is preferably a hydrogen atom, or an alkyl group having 1 to 3 carbon atoms, any 1 to 3 hydrogen atoms of which are optionally substituted with a fluorine atom(s) or a chlorine atom(s), more preferably a hydrogen atom, or an alkyl group having 1 to 3 carbon atoms, any 1 to 3 hydrogen atoms of which are optionally substituted with a fluorine atom(s), and still more preferably a hydrogen atom, a methyl group, or an ethyl group.

R⁸ is more preferably a hydrogen atom, a methyl group, an acyl group having 2 to 4 carbon atoms, or an alkylsulfonyl group having 1 to 3 carbon atoms, and still more preferably a hydrogen atom, a methyl group, an acetyl group, a propionyl group, a methylsulfonyl group, or an ethylsulfonyl group.

Specific examples of preferred compound of the cyclic amine derivative represented by formula (I) are shown in Tables 1-1 to 1-3, but this disclosure is not limited thereto.

TABLE 1-1

Structural formula

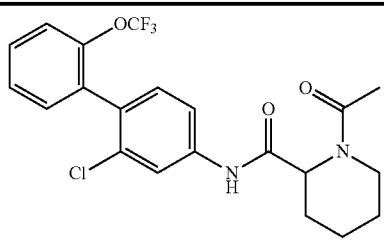

TABLE 1-1-continued

Structural formula

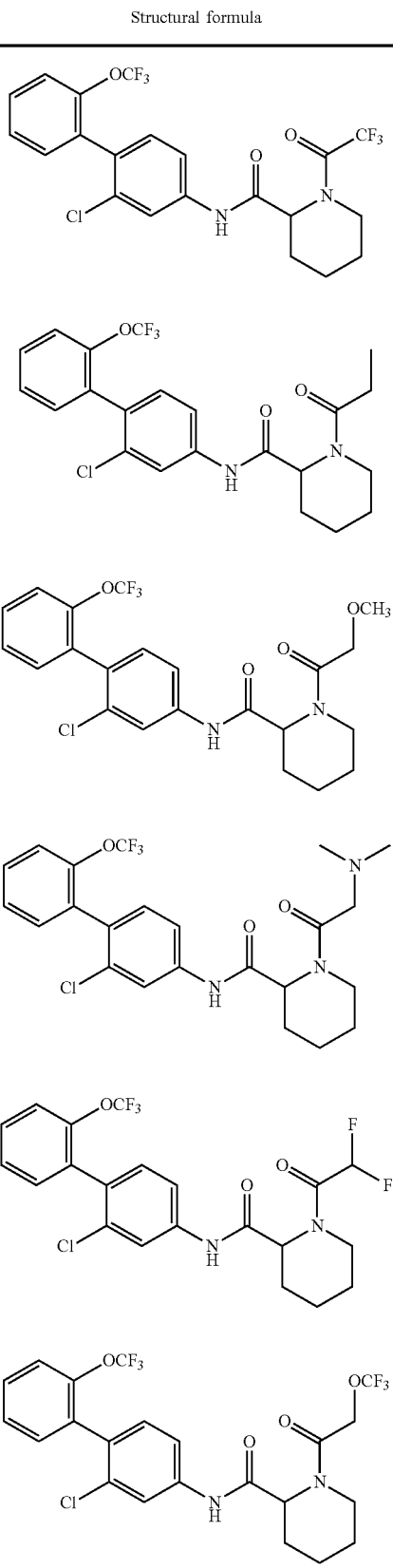

TABLE 1-1-continued
Structural formula
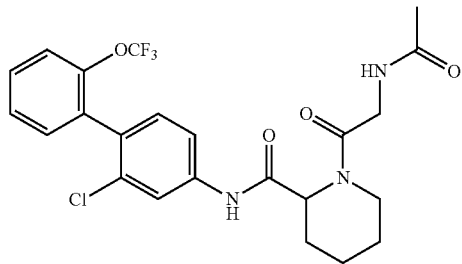 [SMILES: CC(=O)NCC(=O)N1CCCCC1C(=O)Nc1ccc(-c2ccccc2OC(F)(F)F)c(Cl)c1]
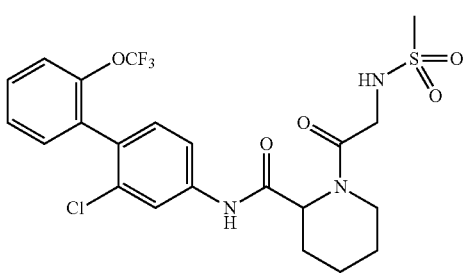 [SMILES: CS(=O)(=O)NCC(=O)N1CCCCC1C(=O)Nc1ccc(-c2ccccc2OC(F)(F)F)c(Cl)c1]
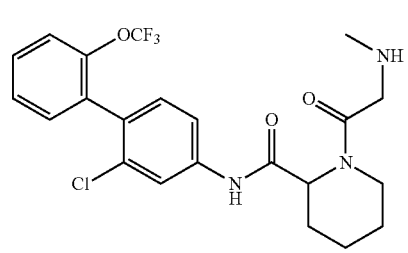 [SMILES: CNCC(=O)N1CCCCC1C(=O)Nc1ccc(-c2ccccc2OC(F)(F)F)c(Cl)c1]
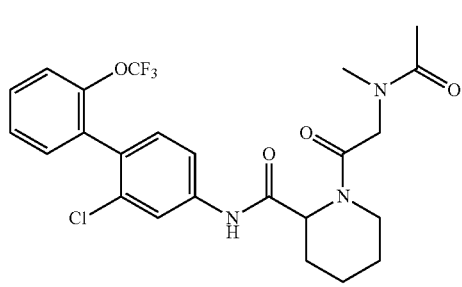 [SMILES: CC(=O)N(C)CC(=O)N1CCCCC1C(=O)Nc1ccc(-c2ccccc2OC(F)(F)F)c(Cl)c1]
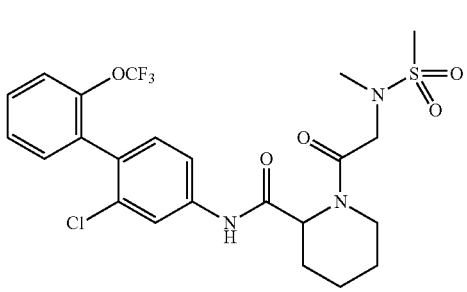 [SMILES: CN(CC(=O)N1CCCCC1C(=O)Nc1ccc(-c2ccccc2OC(F)(F)F)c(Cl)c1)S(C)(=O)=O]
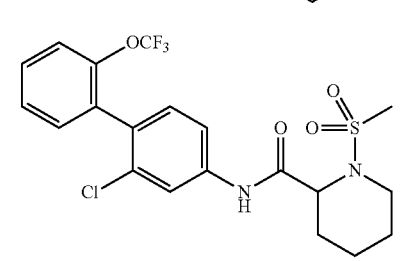
TABLE 1-1-continued
Structural formula
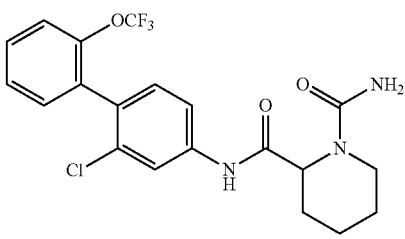 [SMILES: NC(=O)N1CCCCC1C(=O)Nc1ccc(-c2ccccc2OC(F)(F)F)c(Cl)c1]
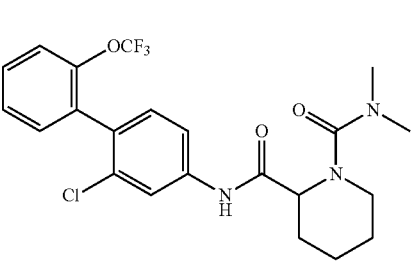 [SMILES: CN(C)C(=O)N1CCCCC1C(=O)Nc1ccc(-c2ccccc2OC(F)(F)F)c(Cl)c1]
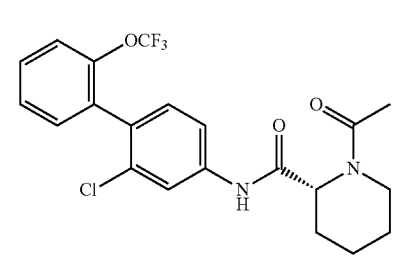
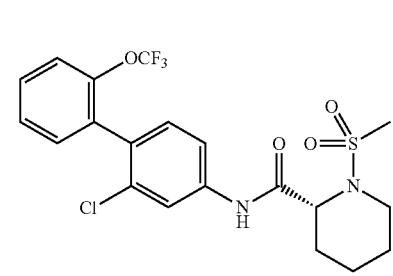
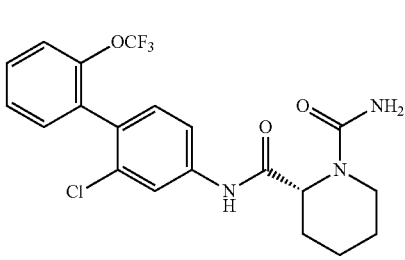 [SMILES: NC(=O)N1CCCC[C@@H]1C(=O)Nc1ccc(-c2ccccc2OC(F)(F)F)c(Cl)c1]
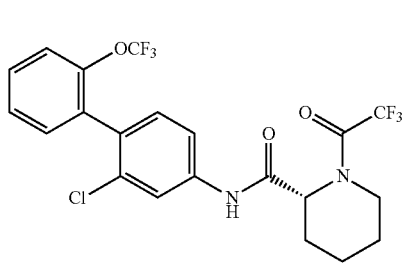 [SMILES: O=C(Nc1ccc(-c2ccccc2OC(F)(F)F)c(Cl)c1)[C@H]1CCCCN1C(=O)C(F)(F)F]

TABLE 1-1-continued

Structural formula

TABLE 1-2

Structural formula

TABLE 1-2-continued

Structural formula

TABLE 1-2-continued
Structural formula
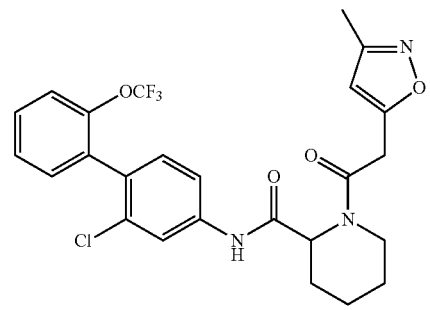 [SMILES: Cc1cc(CC(=O)N2CCCCC2C(=O)Nc2ccc(-c3ccccc3OC(F)(F)F)c(Cl)c2)on1]
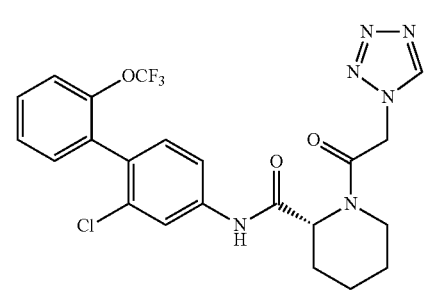 [SMILES: O=C(Nc1ccc(-c2ccccc2OC(F)(F)F)c(Cl)c1)[C@H]1CCCCN1C(=O)Cn1cnnn1]
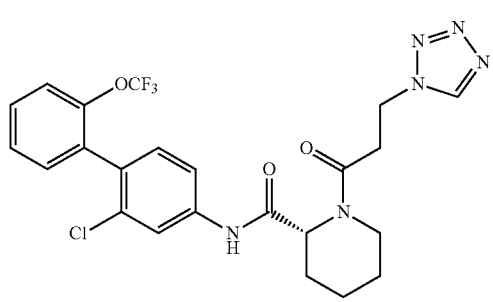 [SMILES: O=C(Nc1ccc(-c2ccccc2OC(F)(F)F)c(Cl)c1)[C@H]1CCCCN1C(=O)CCn1cnnn1]
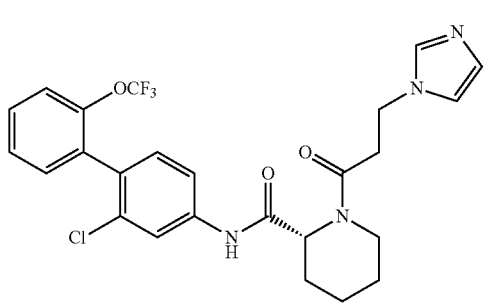 [SMILES: O=C(Nc1ccc(-c2ccccc2OC(F)(F)F)c(Cl)c1)[C@H]1CCCCN1C(=O)CCn1ccnc1]
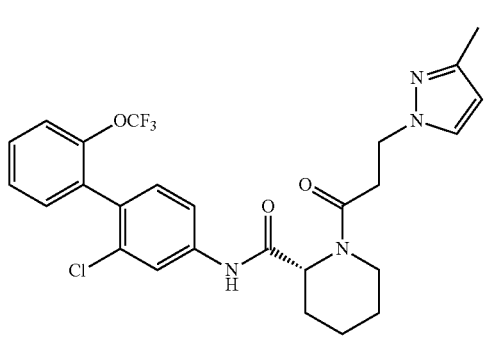 [SMILES: Cc1ccn(CCC(=O)N2CCCC[C@@H]2C(=O)Nc2ccc(-c3ccccc3OC(F)(F)F)c(Cl)c2)n1]
TABLE 1-3
Structural formula
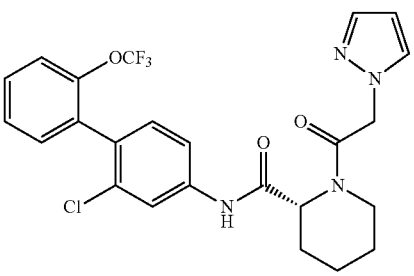 [SMILES: O=C(Nc1ccc(-c2ccccc2OC(F)(F)F)c(Cl)c1)[C@H]1CCCCN1C(=O)Cn1cccn1]
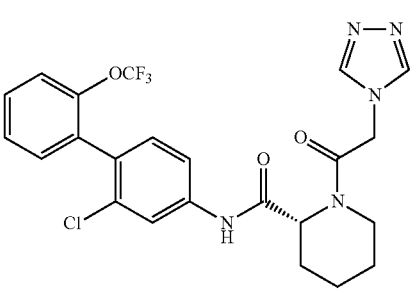
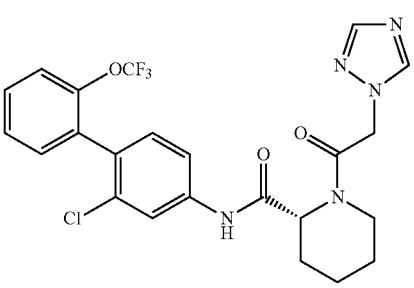
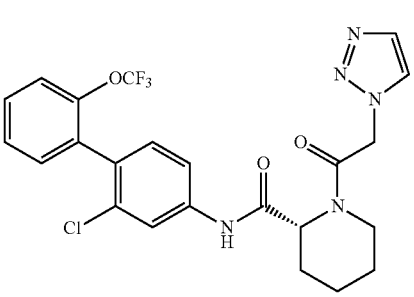
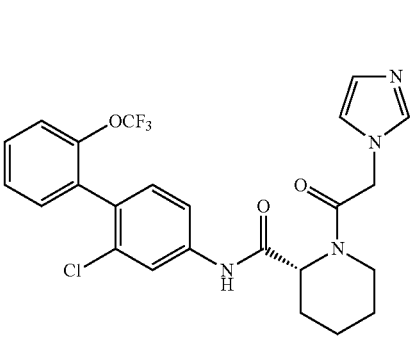

TABLE 1-3-continued

Structural formula

[Chemical structures showing cyclic amine derivatives with OCF₃, Cl-substituted biphenyl, amide linkage, and piperidine groups with various substituents]

The compounds mentioned in Tables 1-1 to 1-3 also include pharmacologically acceptable salts thereof.

The cyclic amine derivative represented by formula (I) might include conformational isomers, rotamers, tautomers, optical isomers, diastereomers and the like, and include not only a single isomer but also racemates and diastereomer mixtures.

The cyclic amine derivative represented by formula (I) may be labeled with one or more isotopes, and examples of the labeled isotope include $^2H$, $^3H$, $^{13}C$, $^{14}C$, $^{15}N$, $^{15}O$, $^{18}O$ and/or $^{125}I$.

Examples of the "pharmacologically acceptable salt" of the cyclic amine derivative represented by formula (I) include a salt with an inorganic base, a salt with an organic base, a salt with an inorganic acid, and a salt with an organic acid. Examples of the salt with an inorganic base include an alkali metal salt such as a sodium salt or a potassium salt, an alkaline earth metal salt such as a calcium salt or a magnesium salt, an ammonium salt, an aluminum salt or a zinc salt, and examples of the salt with an organic base include a salt with an organic amine such as triethylamine, ethanolamine, morpholine, piperidine or dicyclohexylamine, or a salt with a basic amino acid such as arginine or lysine. Examples of the salt with an inorganic acid include a hydrochloride, a sulfate, a nitrate, a hydrobromide, a hydroiodide, a phosphate or the like, and examples of the salt with an organic acid include an oxalate, a malonate, a citrate, a fumarate, a lactate, a malate, a succinate, a tartrate, an acetate, a trifluoroacetate, a maleate, a gluconate, a benzoate, an ascorbate, a glutarate, a mandelate, a phthalate, a methanesulfonate, an ethanesulfonate, a benzenesulfonate, a p-toluenesulfonate, a camphorsulfonate, an aspartate, a glutamate, a cinnamate or the like.

The cyclic amine derivative represented by formula (I) or a pharmacologically acceptable salt thereof may be an anhydride or a solvate such as a hydrate. Here, the solvate is preferably a pharmacologically acceptable solvate. The pharmacologically acceptable solvate may be either a hydrate or a non-hydrate and is preferably a hydrate. Examples of the solvent constituting the solvate include alcohol-based solvents such as methanol, ethanol, or n-propanol, N,N-dimethylformamide (hereinafter abbreviated to DMF), dimethylsulfoxide (hereinafter abbreviated to DMSO), or water.

The cyclic amine derivative represented by formula (I) (hereinafter referred to as a cyclic amine derivative (I)) can be produced by an appropriate method based on features derived from a basic skeleton and types of substituents thereof. A starting material and a reagent used in the production of these compounds can generally be commercially available or produced by known methods.

The cyclic amine derivative (I) and the intermediate and starting material to be used in the production thereof can be isolated and purified by known means. Examples of known means for isolation and purification include solvent extraction, recrystallization, or chromatography.

When the cyclic amine derivative (I) contains an optical isomer or a stereoisomer, each isomer can be obtained as a single compound by a known method. Examples of the known method include crystallization, enzymatic resolution, or chiral chromatography.

In each of the reactions of the production methods mentioned below, when the starting compound has an amino group or a carboxyl group, a protective group may be introduced into these groups, and after the reaction, the protective group can be deprotected as appropriate to obtain the target compound.

Examples of the protective group of the amino group include an alkylcarbonyl group having 2 to 6 carbon atoms (e.g., an acetyl group), a benzoyl group, an alkyloxycarbonyl group having 2 to 8 carbon atoms (e.g., a tert-butoxycarbonyl group or a benzyloxy carbonyl group), an aralkyl group having 7 to 10 carbon atoms (e.g., a benzyl group), or a phthaloyl group.

Examples of the protective group of the carboxyl group include an alkyl group having 1 to 6 carbon atoms (e.g., a methyl group, an ethyl group, or a tert-butyl group) or an aralkyl group having 7 to 10 carbon atoms (e.g., a benzyl group).

The deprotection of the protective group varies depending on the kind of the protective group, but deprotection can be performed according to a known method (for example, Greene, TW, "Greene's Protective Groups in Organic Synthesis", Wiley-Interscience) or a method analogous thereto.

As shown in, for example, Scheme 1, the cyclic amine derivative (I) can be obtained by a coupling reaction (first step) of a boronic acid derivative (II) with an aryl halide derivative (III) in the presence of a metal catalyst and a base, followed by a condensation reaction (second step) of the biphenylamine derivative (IV) obtained in the first step with a pipecolic acid derivative (V) in the presence of a condensing agent and a base, followed by a deprotection reaction (third step) of the N-tert-butoxycarbonylpipecolic acid amide derivative (VI) obtained in the second step in the presence of an acid, and followed by a condensation reaction (fourth step) of the pipecolic acid amide derivative (VII) obtained in the third step with an organic acid anhydride derivative (VIII) in the presence of a base. The cyclic amine derivative (I) can also be obtained by a condensation reaction of the pipecolic acid amide derivative (VII) with an organic acid ester derivative (IX). The cyclic amine derivative (I) can also be obtained by a condensation reaction of the pipecolic acid amide derivative (VII) with an organic acid chloride derivative (X) in the presence of a base. The cyclic amine derivative (I) can also be obtained by a condensation reaction of the pipecolic acid amide derivative (VII) and an organic acid derivative (XI) in the presence of a condensing agent and a base. The cyclic amine derivative (I) can also be obtained by a condensation reaction of the pipecolic acid amide derivative (VII) with trimethylsilyl isocyanate in the presence of a base.

When the cyclic amine derivative (I) contains, for example, an amino group, the amino group may be converted into an amide group, a sulfonamide group or the like, or an N-alkyl derivative by a condensation reaction, a reductive amination reaction or the like. When the cyclic amine derivative (I) contains a sulfide group, the sulfide group may be converted into a sulfonyl group by an oxidation reaction. When the cyclic amine derivative (I) contains an ester group, the ester group may be converted into a carboxyl group by a hydrolysis reaction.

Scheme 1

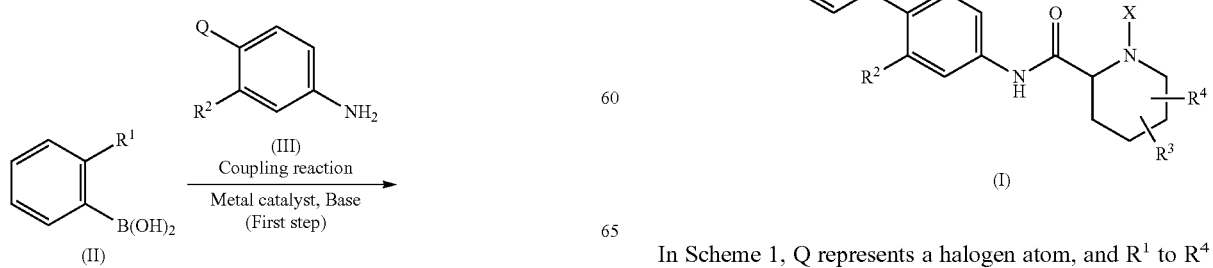

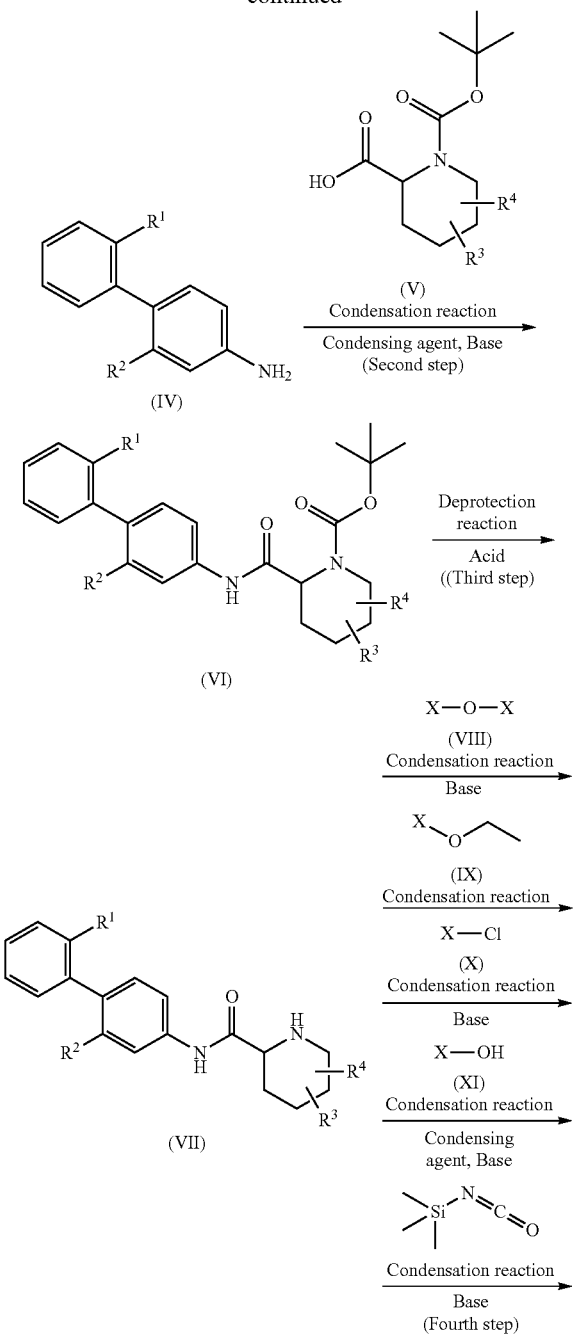

In Scheme 1, Q represents a halogen atom, and $R^1$ to $R^4$ and X are as defined above.

First Step

The amount of the aryl halide derivative (III) used in the coupling reaction is preferably 0.5 to 10 equivalents, and more preferably 0.7 to 3 equivalents, based on the boronic acid derivative (II).

Examples of the metal catalyst used in the coupling reaction include 1,1'-bis(diphenylphosphino)ferrocene dichloropalladium(II) dichloromethane adduct, palladium (II) chloride, bis(dibenzylideneacetone)palladium(0), tetrakistriphenylphosphine palladium(0), or dichlorobistriphenylphosphine palladium(0), and 1,1'-bis(diphenylphosphino) ferrocene dichloropalladium(II) dichloromethane adduct is preferable.

The amount of the metal catalyst used for the coupling reaction is preferably 0.01 to 5 equivalents, and more preferably 0.05 to 0.5 equivalents, based on the boronic acid derivative (II).

Examples of the base used in the coupling reaction include an organic base such as triethylamine or diisopropylethylamine, an inorganic base such as sodium carbonate or potassium carbonate, a lithium amide such as lithium hexamethyldisilazide or lithium diisopropylamide, or a metal alkoxide such as tert-butyloxy sodium, tert-butyloxy potassium, or a mixture thereof, and an inorganic base such as sodium carbonate or potassium carbonate, is preferable.

The amount of the base used in the coupling reaction is preferably 0.5 to 10 equivalents, and more preferably 1 to 3 equivalents, based on the boronic acid derivative (II).

The reaction solvent used for the coupling reaction is appropriately selected according to the type of reagent to be used or the like, but is not particularly limited as long as it does not inhibit the reaction, and examples thereof include ether-based solvents such as tetrahydrofuran, 1,4-dioxane, ethylene glycol dimethyl ether, or dimethoxyethane, nitrile-based solvents such as acetonitrile or propionitrile, aromatic hydrocarbon solvents such as benzene or toluene, aprotic polar solvents such as DMF or DMSO, water, or a mixture thereof. A mixed solvent of nitrile-based solvents such as acetonitrile or propionitrile, and water, is preferable.

The reaction temperature of the coupling reaction is preferably 0 to 200° C., and more preferably from 50 to 150° C.

The reaction time of the coupling reaction is appropriately selected according to the conditions such as the reaction temperature, and the reaction time is preferably 1 to 30 hours.

The concentration of the boronic acid derivative (II) used in the coupling reaction at the start of the reaction is preferably 1 mmol/L to 1 mol/L.

The boronic acid derivative (II) and aryl halide derivative (III) used in the coupling reaction can be purchased or produced by a known method.

Step 2

The amount of the pipecolic acid derivative (V) used in the condensation reaction is preferably 0.1 to 10 equivalents, and more preferably 0.5 to 3 equivalents, based on the biphenylamine derivative (IV).

Examples of the condensing agent used in the condensation reaction include N,N'-dicyclohexylcarbodiimide, N-ethyl-N'-3-dimethylaminopropylcarbodiimide hydrochloride, N,N'-carbodiimidazole, {{[(1-cyano-2-ethoxy-2-oxoethylidene)amino]oxy}-4-morpholinomethylene}dimethylammonium hexafluorophosphate (hereinafter abbreviated to COMU), O-(7-azabenzotriazol-1-yl)-1,1,3,3-tetramethyluronium hexafluorophosphate (hereinafter abbreviated to HATU), or O-(benzotriazol-1-yl)-N,N,N',N'-tetramethyluronium hexafluorophosphate (hereinafter abbreviated to HBTU), and HATU or HBTU is preferable.

The amount of the condensing agent used in the condensation reaction is preferably 0.5 to 10 equivalents, and more preferably 1 to 3 equivalents, based on the biphenylamine derivative (IV).

Examples of the base used in the condensation reaction include an organic base such as triethylamine or diisopropylethylamine, an inorganic base such as sodium hydrogen carbonate or potassium carbonate, a hydrogenated metal compound such as sodium hydride, potassium hydride, or calcium hydride, an alkyl lithium such as methyl lithium or butyl lithium, a lithium amide such as lithium hexamethyldisilazide or lithium diisopropylamide, or a mixture thereof, and an organic base such as triethylamine or diisopropylethylamine, is preferable.

The amount of the base used in the condensation reaction is preferably 0.5 to 10 equivalents, and more preferably 1 to 5 equivalents, based on the biphenylamine derivative (IV).

The biphenylamine derivative (IV) used in the condensation reaction may be a free form or a salt such as a hydrochloride.

The reaction solvent used in the condensation reaction is appropriately selected according to the type of the reagent to be used or the like, but is not particularly limited as long as it does not inhibit the reaction, and examples thereof include ether-based solvents such as tetrahydrofuran, 1,4-dioxane, ethylene glycol dimethyl ether, or dimethoxyethane, halogen-based solvents such as dichloromethane, chloroform, or 1,2-dichloroethane, aprotic polar solvents such as DMF or DMSO, or nitrile-based solvents such as acetonitrile or propionitrile, and halogen-based solvents such as dichloromethane, chloroform, or 1,2-dichloroethane, or aprotic polar solvents such as DMF or DMSO, are preferable.

The reaction temperature of the condensation reaction is preferably 0 to 200° C., and more preferably 20 to 100° C.

The reaction time of the condensation reaction is appropriately selected according to the conditions such as the reaction temperature, and is preferably 0.5 to 100 hours.

The concentration of the biphenylamine derivative (IV) used in the condensing reaction at the start of the reaction is preferably 1 mmol/L to 1 mol/L.

The pipecolic acid derivative (V) used in the condensation reaction can be purchased or produced by a known method or a method analogous thereto.

Third Step

Examples of the acid used in the deprotection reaction include hydrochloric acid, trifluoroacetic acid, or hydrofluoric acid, and hydrochloric acid or trifluoroacetic acid is preferable.

The amount of the acid used in the deprotection reaction is preferably 0.5 to 100 equivalents, and more preferably 1 to 30 equivalents, based on the N-tert-butoxycarbonylpipecolic acid amide derivative (VI).

The reaction solvent used in the deprotection reaction is appropriately selected according to the type of the reagent to be used, but is not particularly limited as long as it does not inhibit the reaction, and examples thereof include ether-based solvents such as diethyl ether, tetrahydrofuran, dimethoxyethane, or 1,4-dioxane, ester-based solvents such as ethyl acetate or propyl acetate, chlorine-based solvents such as dichloromethane, chloroform, or 1,2-dichloroethane, alcohol-based solvents such as methanol or ethanol, aprotic polar solvents such as DMF or DMSO, or mixed solvents thereof, and halogen-based solvents such as dichloromethane, chloroform, or 1,2-dichloroethane, or aprotic polar solvents such as DMF or DMSO, are preferable.

The reaction temperature of the deprotection reaction is preferably −78° C. to 200° C., and more preferably −20° C. to 100° C.

The reaction time of the deprotection reaction is appropriately selected according to the conditions such as the reaction temperature, and the reaction time is preferably 1 to 50 hours.

The concentration of the N-tert-butoxycarbonylpipecolic acid amide derivative (VI) used in the deprotection reaction at the start of the reaction is preferably 1 mmol/L to 1 mol/L.

Step 4

The amount of the organic acid anhydride derivative (VIII), the organic acid ester derivative (IX), the organic acid chloride derivative (X), the organic acid derivative (XI), or trimethylsilyl isocyanate used in the condensation reaction is preferably 1 to 200 equivalents, and more preferably 1 to 80 equivalents, based on the pipecolic acid amide derivative (VII).

Examples of the condensing agent used in the condensation reaction include N,N'-dicyclohexylcarbodiimide, N-ethyl-N'-3-dimethylaminopropylcarbodiimide hydrochloride, N,N'-carbodiimidazole, COMU, HATU, or HBTU, and HATU or HBTU is preferable.

The amount of the condensing agent used in the condensation reaction is preferably 0 to 10 equivalents, and more preferably 0 to 3 equivalents, based on the pipecolic acid amide derivative (VII).

Examples of the base used in the condensation reaction include an organic base such as triethylamine or diisopropylethylamine, an inorganic base such as sodium hydrogen carbonate or potassium carbonate, a hydrogenated metal compound such as sodium hydride, potassium hydride, or calcium hydride, an alkyl lithium such as methyl lithium or butyl lithium, lithium amide such as lithium hexamethyldisilazide or lithium diisopropylamide, or a mixture thereof, and an organic base such as triethylamine or diisopropylethylamine, is preferable.

The amount of the base used in the condensation reaction is preferably 0 to 10 equivalents, and more preferably 0 to 5 equivalents, based on the pipecolic acid amide derivative (VII).

The pipecolic acid amide derivative (VII) used in the condensation reaction may be a free form or a salt such as a hydrochloride.

The reaction solvent used in the condensation reaction is appropriately selected according to the type of the reagent to be used or the like, but is not particularly limited as long as it does not inhibit the reaction, and examples thereof include ether-based solvents such as tetrahydrofuran, 1,4-dioxane, ethylene glycol dimethyl ether, or dimethoxyethane, chlorine-based solvents such as dichloromethane, chloroform, or 1,2-dichloroethane, aprotic polar solvents such as DMF or DMSO, or nitrile-based solvents such as acetonitrile or propionitrile, and halogen-based solvents such as dichloromethane, chloroform, or 1,2-dichloroethane, or aprotic polar solvents such as DMF or DMSO, are preferable.

The reaction temperature of the condensation reaction is preferably −78° C. to 200° C., and more preferably −20° C. to 100° C.

The reaction time of the condensation reaction is appropriately selected according to the conditions such as the reaction temperature, and the reaction time is preferably 0.5 to 100 hours.

The concentration of the pipecolic acid amide derivative (VII) used in the coupling reaction at the start of the reaction is preferably 1 mmol/L to 1 mol/L.

The organic acid anhydride derivative (VIII), the organic acid ester derivative (IX), the organic acid chloride derivative (X), the organic acid derivative (XI), and the trimethylsilyl isocyanate used in the condensation reaction can be purchased or produced by a known method or a method analogous thereto.

The medicament, the RORγ antagonist, and the therapeutic agent or preventive agent for an autoimmune disease or allergic disease are characterized by containing the cyclic amine derivative (I) or a pharmacologically acceptable salt thereof as an active ingredient. The autoimmune disease mentioned above is preferably multiple sclerosis or psoriasis, and the allergic disease mentioned above is preferably allergic dermatitis, and more preferably contact dermatitis or atopic dermatitis.

"RORγ antagonist" means a compound having an effect to suppress the function of RORγ, thereby eliminating or attenuating the activity thereof.

"Autoimmune disease" is a general term for diseases in which excessive immune responses attack an individual's own normal cells and tissues, resulting in symptoms, and examples thereof include multiple sclerosis, psoriasis, rheumatoid arthritis, systemic lupus erythematosus, ankylosing spondylitis, uveitis, polymyalgia rheumatica, scleroderma, vasculitis, pemphigus, pemphigoid, or dermatomyositis. In addition, the autoimmune disease includes acne or vitiligo.

"Allergic disease" is a disease derived from excessive immune responses to specific antigens, and examples thereof include allergic dermatitis, contact dermatitis, atopic dermatitis, allergic rhinitis (pollinosis), allergic conjunctivitis, allergic gastroenteritis, bronchial asthma, childhood asthma, or food allergy.

"Multiple sclerosis" is a disease characterized by demyelination in which the myelin sheath covering nerve fibers such as the brain, spinal cord, and optic nerve, is destroyed, and characterized by progression of the disorder with repeated relapse and remission. The symptoms vary depending on the site of the lesion, and represent various neurological symptoms such as visual impairment, quadriplegia, sensory disturbance, and gait disturbance. Examples of multiple sclerosis include relapsing-remitting multiple sclerosis, primary progressive multiple sclerosis, and secondary progressive multiple sclerosis.

"Psoriasis" is an inflammatory disease of the skin associated with invasion and activation of immune cells and resultant acanthosis. Typically, a symptom called desquamation in which white scales thickly adhere to red rashes in various parts of the whole body and then peel off occurs. Examples of psoriasis include plaque psoriasis, pustular psoriasis, psoriasis arthropathica, guttate psoriasis, and erythrodermic psoriasis.

"Allergic dermatitis" is a general term for skin diseases caused by allergic reactions and is characterized by chronic itching and rashes on the face, neck, elbow and/or knee. Examples of allergic dermatitis include contact dermatitis, atopic dermatitis and the like.

"Contact dermatitis" is an eczematous inflammatory disease that develops when an exogenous antigen is brought into contact with the skin, and examples thereof include allergic contact dermatitis, photocontact dermatitis, systemic contact dermatitis, and contact urticaria. Examples of the antigen include metal allergens (cobalt, nickel and the like), plant allergens (poison oak, primrose and the like), and food allergens (mango, ginkgo nut and the like).

"Atopic dermatitis" is a skin disease in which many patients have atopic predisposition. It is characterized by symmetric systemic eczema that repeats exacerbation and remission. Examples thereof include diffuse neurodermatitis, atopic eczema, atopic neurodermatitis, Besnier prurigo, acute infantile eczema, flexural eczema, pediatric eczema in extremities, pediatric atopic eczema, pediatric dry eczema, pediatric eczema, adult atopic dermatitis, endogenic eczema, infantile dermatitis, and chronic infantile eczema.

The cyclic amine derivative (I) or a pharmacologically acceptable salt thereof is characterized by suppressing the function of RORγ by inhibiting the binding between RORγ and a coactivator. Since it is known that RORγ is involved in various diseases and that improvement in the pathological state or remission of the symptoms can be expected by suppression of the function of RORγ, the cyclic amine derivative (I) or a pharmacologically acceptable salt thereof can be used as a medicament for diseases in which improvement in the pathological state or remission of the symptoms can be expected by suppression of the function of RORγ, particularly as a therapeutic agent or preventive agent for autoimmune diseases or allergic diseases. The therapeutic agent or preventive agent for autoimmune diseases mentioned above can be preferably used as a therapeutic agent or preventive agent for multiple sclerosis, psoriasis, rheumatoid arthritis, systemic lupus erythematosus, ankylosing spondylitis, uveitis, polymyalgia rheumatica, scleroderma, vasculitis, pemphigus, pemphigoid, dermatomyositis, acne, or vitiligo, and more preferably used as a therapeutic agent or preventive agent for multiple sclerosis or psoriasis. The therapeutic agent or preventive agent for allergic diseases mentioned above can be preferably used as a therapeutic agent or preventive agent for allergic dermatitis, atopic dermatitis, allergic rhinitis (pollinosis), allergic conjunctivitis, allergic gastroenteritis, bronchial asthma, childhood asthma, or food allergy, and more preferably used as a therapeutic agent or preventive agent for contact dermatitis or atopic dermatitis.

It is possible to evaluate that the cyclic amine derivative (I) or a pharmacologically acceptable salt thereof has RORγ antagonist activity that inhibits the binding between RORγ and a coactivator, using an in vitro study. Examples of the in vitro study include a method of evaluating the binding between RORγ and an agonist (e.g., cholesterol) (WO 2012/158784, WO 2013/018695) and a method of evaluating the binding between a ligand-binding domain of RORγ and a coactivator (WO 2012/064744, WO 2013/018695). The inhibitory effect on the transcription activity of RORγ can be evaluated using various reporter gene assays (WO 2012/158784, WO 2012/064744, WO 2013/018695).

The fact that the cyclic amine derivative (I) or a pharmacologically acceptable salt thereof suppresses the function of RORγ can be evaluated using lymphocytic cells derived from various organs such as spleen or peripheral blood, with IL-17 production or Th17 cell differentiation as an index. Examples of the method using IL-17 production as an index include a method of measuring IL-17 production by IL-23 stimulation using mouse splenocytes (The Journal of Biological Chemistry, 2003, Vol. 278, No. 3, p. 1910-1914). Examples of the method using Th17 cell differentiation as an index include a method of measuring the IL-17 production amount or the proportion of IL-17-positive cells and the like by stimulating CD4-positive naive T cells derived from mouse splenocytes or human PBMC with various cytokines (e.g., IL-1β, IL-6, IL-23, and/or TGF-β) and various antibodies (e.g., anti-CD3 antibody, anti-CD28 antibody, anti-IL-4 antibody, anti-IFN-γ antibody, and/or anti-IL-2 antibody) to be differentiated into Th17 (WO 2012/158784, WO 2013/018695).

The fact that the cyclic amine derivative (I) or a pharmacologically acceptable salt thereof is effective for treatment or prevention of autoimmune diseases can be evaluated using a disease model. Examples of the disease model include an experimental autoimmune encephalomyelitis model (Journal of Neuroscience Research, 2006, Vol. 84, p. 1225-1234), an imiquimod-induced psoriasis model (Journal of Immunology, 2009, Vol. 182, p. 5836-5845), a collagen arthritis model (Annual Review of Immunology, 1984, Vol. 2, p. 199-218), a spontaneous model of systemic lupus erythematosus (Nature, 2000, Vol. 404, p. 995-999), an ankylosing spondylitis model (Arthritis Research & Therapy, 2012, Vol. 14, p. 253-265), an experimental autoimmune uveitis model (Journal of Immunology, 2006, Vol. 36, p. 30'71-3081), a scleroderma model (Journal of Investigative Dermatology, 1999, Vol. 112, p. 456-462), a vasculitis model (The Journal of Clinical Investigation, 2002, Vol. 110, p. 955-963), a pemphigus model (The Journal of Clinical Investigation, 2000, Vol. 105, p. 625-631), a pemphigoid model (Experimental Dermatology, 2012, Vol. 21, p. 901-905), a dermatomyositis model (American Journal of Pathology, 1985, Vol. 120, p. 323-325), a spontaneous model of acne (European Journal of Dermatology, 2005, Vol. 15, p. 459-464), or a vitiligo model (Pigment Cell & Melanoma Research, 2014, Vol. 27, p. 1075-1085). The experimental autoimmune encephalomyelitis model is generally used as a multiple sclerosis model. The imiquimod-induced psoriasis model is generally used as a psoriasis model.

The fact that the cyclic amine derivative (I) or a pharmacologically acceptable salt thereof is effective for treatment or prevention of allergic diseases can be evaluated using a disease model. Examples of the disease model include a dinitrofluorobenzene (hereinafter abbreviated to DNFB)-induced allergic dermatitis model (Pharmacological Reports, 2013, Vol. 65, p. 1237-1246), an oxazolone-induced atopic dermatitis model (Journal of Investigative Dermatology, 2014, Vol. 134, p. 2122-2130), an ovalbumin-induced allergic rhinitis model (Journal of Animal Science, 2010, Vol. 81, p. 699-705), an IgE-induced allergic conjunctivitis model (British Journal of Ophthalmology, 2012, Vol. 96, p. 1332-1336), an allergic gastroenteritis model (Gastroenterology, 1997, Vol. 113, p. 1560-1569), an ovalbumin-induced asthma model (American Journal of Respiratory and Critical Care Medicine, 1997, Vol. 156, p. 766-775), or an ovalbumin-induced food allergy model (Clinical & Experimental Allergy, 2005, Vol. 35, p. 461-466). The DNFB-induced allergic dermatitis model is generally used as an allergic dermatitis model, particularly as a contact dermatitis model. The oxazolone-induced atopic dermatitis model is generally used as an atopic dermatitis model.

The efficacy of the cyclic amine derivative (I) or a pharmacologically acceptable salt thereof for treatment or prevention of autoimmune diseases or allergic diseases can be evaluated using the in vitro study mentioned above, for example, with decrease in the amount of binding between a ligand-binding domain of RORγ and a coactivator, or decrease in the IL-17 production amount, which is an index of the function of RORγ, as an index. The efficacy for treatment or prevention of multiple sclerosis can be evaluated using the experimental autoimmune encephalomyelitis model mentioned above, for example, with decrease in the neurological symptom score, which is a characteristic index of multiple sclerosis, as an index. The efficacy for treatment or prevention of psoriasis can be evaluated using the imiquimod-induced psoriasis model mentioned above, for example, with decrease in the thickness of the skin such as auricle, which increases with progression of symptoms of the psoriasis model, as an index. The efficacy for treatment or prevention of allergic dermatitis, particularly contact dermatitis, can be evaluated using the DNFB-induced allergic dermatitis model mentioned above, for example, with decrease in the thickness of the skin such as auricle, which increases with progression of dermatitis symptoms, as an index. The efficacy for treatment or prevention of atopic dermatitis can be evaluated using the oxazolone-induced atopic dermatitis model mentioned above, for example, with decrease in the thickness of the skin such as auricle, which increases with progression of dermatitis symptoms, as an index.

The cyclic amine derivative (I) or a pharmacologically acceptable salt thereof can be used as a useful medicament (particularly, a therapeutic agent or preventive agent for an autoimmune disease or an allergic disease) when administered to a mammal (for example, mouse, rat, hamster, rabbit, dog, monkey, bovine, sheep, or human), particularly human. When the cyclic amine derivative (I) or a pharmacologically acceptable salt thereof is clinically used as a medicament, the cyclic amine derivative (I) or a pharmacologically acceptable salt thereof may be used as it is or may be appropriately mixed with additives such as excipients, stabilizers, preservatives, buffers, solubilizers, emulsifiers, diluents, or isotonizing agents. The medicament mentioned above can be manufactured by a usual method using these drug carriers appropriately. Examples of the dosage form of the medicament mentioned above include oral preparations such as tablets, capsules, granules, powders, or syrups; parenteral preparations such as inhalants, injections, suppositories, or liquids; or ointments, creams, or patches for topical administration. Furthermore, known long-acting preparations may be used.

The medicament mentioned above preferably contains 0.00001 to 90% by weight, and more preferably 0.01 to 70% by weight of the cyclic amine derivative (I) or a pharmacologically acceptable salt thereof. The dose is appropriately selected according to the symptoms, age, and body weight of the patient, and the administration method. As an amount of effective ingredients for an adult, 0.1 μg to 1 g per day for injections, 1 μg to 10 g per day for oral preparations, and 1 μg to 10 g per day for patches are preferable, and each can be administered once or several times in divided doses.

Examples of the pharmacologically acceptable carrier or diluent of the abovementioned medicament include a binder (syrup, gelatin, gum arabic, sorbitol, polyvinyl chloride, tragacanth or the like), an excipient (sugar, lactose, corn starch, calcium phosphate, sorbitol, glycine or the like), or a lubricant (magnesium stearate, polyethylene glycol, talc, silica or the like).

To supplement or enhance the therapeutic or preventive effect or to reduce the dosage, the medicament may be used in mixture or combination with other medicaments in suitable amounts.

Our derivatives, treatments and methods will be described in more detail by way of the following Reference Examples and Examples, but this disclosure is not limited thereto.

EXAMPLES

Commercially available compounds were used for the compounds used in the synthesis of the compounds of Reference Examples and Examples, no mention being made on the synthesis method thereof. "Room temperature" in the following Reference Examples and Examples usually indicates the temperature in a range of about 10° C. to about 35° C. Percentage (%) is mol/mol % for yield, % by volume for solvents used in column chromatography and high-performance liquid chromatography, and % by weight for others unless otherwise specified. The name of the solvent shown in the NMR data indicates the solvent used for the measurement. 400 MHz NMR spectrum was measured using JNM-AL 400 nuclear magnetic resonance spectrometer (JEOL Ltd.) or JNM-ECS 400 nuclear magnetic resonance spectrometer (JEOL Ltd.). Chemical shift was indicated by δ (unit: ppm) with tetramethylsilane as a standard, signals were indicated by s (singlet), d (doublet), t (triplet), q (quartet), quint (quintet), sept (septet), m (multiplet), br (broad), dd (double doublet), dt (double triplet), ddd (double double doublet), dq (double quartet), td (triplet doublet), and tt (triplet triplet). Mention is not made when protons of a hydroxyl group, an amino group or the like have a very gentle peak. ESI-MS spectra were measured using Agilent Technologies 1200 Series, G6130A (Agilent Technologies). Silica gel 60 (Merck) was used as silica gel, amine silica gel DM 1020 (Fuji Silysia Chemical Ltd.) was used as amine silica gel, and YFLC W-prep2XY (Yamazen Corporation) was used as chromatography.

Reference Example 1

Synthesis of 2-chloro-2'-(trifluoromethoxy)-[1,1'-biphenyl]-4-amine

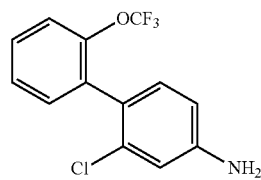 [SMILES: Nc1ccc(-c2ccccc2OC(F)(F)F)c(Cl)c1]

To an acetonitrile (9.0 mL) solution of 2-trifluoromethoxyphenylboronic acid (1.10 g, 5.33 mmol), 4-bromo-3-chloroaniline (1.00 g, 4.84 mmol), potassium carbonate (1.00 g, 7.27 mmol), 1,1'-bis(diphenylphosphino) ferrocene dichloropalladium(II) dichloromethane adduct (0.396 g, 0.484 mmol), and distilled water (3.0 mL) were added at room temperature and the temperature was raised to 90° C., followed by stirring for 18 hours. The reaction solution was filtered through silica gel and then the filtrate was concentrated under reduced pressure. The residue was purified by column chromatography (silica gel, n-hexane/ethyl acetate=85/15 to 67/33) to obtain 2-chloro-2'-(trifluoromethoxy)-[1,1'-biphenyl]-4-amine (hereinafter referred to as the compound of Reference Example 1) (1.03 g, 3.57 mmol, 73.6%) as a yellow oily product.

$^1$H-NMR (400 MHz, CDCl$_3$) δ: 3.79(s, 2H), 6.62(dd, J=8.3, 2.3 Hz, 1H), 6.80(d, J=2.3 Hz, 1H), 7.05(d, J=8.3 Hz, 1H), 7.30-7.41(m, 4H).

ESI-MS: m/z=288(M+H)$^+$.

Reference Example 2

Synthesis of tert-butyl 2-((2-chloro-2'-(trifluoromethoxy)-[1,1'-biphenyl]-4-yl)carbamoyl)piperidine-1-carboxylate

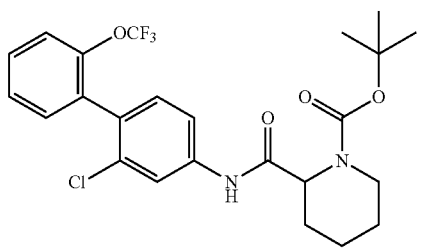

To a DMF (2.0 mL) solution of 1-(tert-butoxycarbonyl)piperidine-2-carboxylic acid (0.263 g, 1.15 mmol), a DMF (2.0 mL) solution of the compound of Reference Example 1 (0.300 g, 1.04 mmol), HATU (0.436 g, 1.15 mmol), and diisopropylethylamine (0.273 mL, 1.56 mmol) were added at room temperature, followed by stirring at the same temperature for 16 hours. To the reaction solution, distilled water was added, and the solution was extracted with a mixed solvent of n-hexane/ethyl acetate=20/80 (v/v). The organic layer was washed with saturated brine, dried over anhydrous sodium sulfate and filtered, and then the filtrate was concentrated under reduced pressure. The residue was purified by column chromatography (silica gel, n-hexane/ethyl acetate=90/10 to 67/33) to obtain tert-butyl 2-((2-chloro-2'-(trifluoromethoxy)-[1,1'-biphenyl]-4-yl)carbamoyl)piperidine-1-carboxylate (hereinafter referred to as the compound of Reference Example 2) (0.483 g, 0.968 mmol, 92.8%) as a white solid.

$^1$H-NMR (400 MHz, CDCl$_3$) δ: 1.43-1.51(m, 2H), 1.53(s, 9H), 1.60-1.75(m, 3H), 2.35(d, J=12.7 Hz, 1H), 2.80-2.89 (m, 1H), 4.03-4.13(m, 1H), 4.86-4.89(m, 1H), 7.22(d, J=8.3 Hz, 1H), 7.29-7.45(m, 6H), 7.80(br, 1H).

ESI-MS: m/z=499(M+H)$^+$.

Reference Example 3

Synthesis of N-(2-chloro-2'-(trifluoromethoxy)-[1,1'-biphenyl]-4-yl)piperidine-2-carboxamide

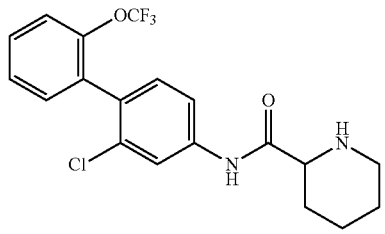 [SMILES: O=C(Nc1ccc(-c2ccccc2OC(F)(F)F)c(Cl)c1)C1CCCCN1]

To a dichloromethane (5.0 mL) solution of the compound of Reference Example 2 (0.483 g, 0.968 mmol), trifluoroacetic acid (0.522 mL, 6.78 mmol) was added at room temperature, followed by stirring at the same temperature for 20 hours. The reaction solution was concentrated under reduced pressure, neutralized with an aqueous potassium carbonate solution, and then extracted with chloroform. The organic layer was dried over anhydrous sodium sulfate and filtered, and then the filtrate was concentrated under reduced pressure. The residue was purified by column chromatography (amine silica gel, n-hexane/ethyl acetate=60/40 to 20/80) to obtain N-(2-chloro-2'-(trifluoromethoxy)-[1,1'-biphenyl]-4-yl)piperidine-2-carboxamide (hereinafter referred to as the compound of Reference Example 3) (0.309 g, 0.775 mmol, 80.0%) as a white solid.

$^1$H-NMR (400 MHz, CDCl$_3$) δ: 1.53(ddd, J=36.8, 17.9, 8.8 Hz, 4H), 1.78-1.86(m, 1H), 2.00-2.07(m, 1H), 2.74-2.82 (m, 1H), 3.03-3.10(m, 1H), 3.38(dd, J=9.6, 3.5 Hz, 1H), 7.23(d, J=8.3 Hz, 1H), 7.31-7.37(m, 3H), 7.40-7.45(m, 1H), 7.53(dd, J=8.3, 2.0 Hz, 1H), 7.82(d, J=2.2 Hz, 1H), 9.02(br, 1H).

ESI-MS: m/z=399(M+H)$^+$.

Example 1

Synthesis of 1-acetyl-N-(2-chloro-2'-(trifluoromethoxy)-[1,1'-biphenyl]-4-yl)piperidine-2-carboxamide

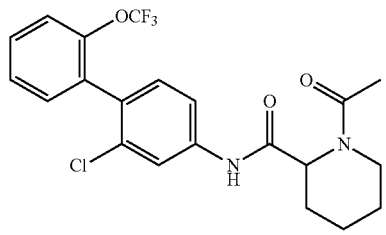

To a dichloromethane (3.0 mL) solution of the compound of Reference Example 3 (0.0700 g, 0.176 mmol), triethylamine (0.0367 mL, 0.263 mmol) and acetic anhydride (0.0182 mL, 0.193 mmol) were added at 0° C. and the temperature was raised to room temperature, followed by stirring for 1 hour. To the reaction solution, distilled water was added, and the solution was extracted with chloroform. The organic layer was washed with distilled water and saturated brine, dried over anhydrous sodium sulfate and filtered, and then the filtrate was concentrated under reduced pressure. The residue was purified by column chromatography (silica gel, chloroform/methanol=95/5) to obtain 1-acetyl-N-(2-chloro-2'-(trifluoromethoxy)-[1,1'-biphenyl]-4-yl)piperidine-2-carboxamide (hereinafter referred to as the compound of Example 1) (0.0730 g, 0.166 mmol, 94.3%) as a white solid.

$^1$H-NMR (400 MHz, CDCl$_3$) δ: 1.46-1.63(m, 1H), 1.67(d, J=7.8 Hz, 1H), 1.89-2.02(m, 2H), 2.22(s, 3H), 2.29(d, J=12.9 Hz, 1H), 3.22(t, J=13.2 Hz, 1H), 3.78(d, J=12.7 Hz, 1H), 5.29(d, J=5.1 Hz, 1H), 7.20(d, J=8.3 Hz, 1H), 7.29-7.37(m, 3H), 7.40-7.44(m, 2H), 7.80(br, 1H), 8.65(br, 1H).

ESI-MS: m/z=441(M+H)$^+$.

Example 2

Synthesis of N-(2-chloro-2'-(trifluoromethoxy)-[1,1'-biphenyl]-4-yl)-1-(2,2,2-trifluoroacetyl)piperidine-2-carboxamide

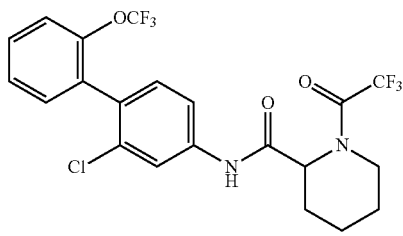 [SMILES: O=C(Nc1ccc(-c2ccccc2OC(F)(F)F)c(Cl)c1)C1CCCCN1C(=O)C(F)(F)F]

According to the same procedure as in Example 1, except that trifluoroacetic anhydride was used in place of acetic anhydride, N-(2-chloro-2'-(trifluoromethoxy)-[1,1'-biphenyl]-4-yl)-1-(2,2,2-trifluoroacetyl)piperidine-2-carboxamide (hereinafter referred to as the compound of Example 2) (0.0500 g, 0.101 mmol, 99.0%) was obtained as a white solid.

$^1$H-NMR (400 MHz, CDCl$_3$) δ: 1.56-1.86(m, 4H), 1.98 (dt, J=11.2, 4.6 Hz, 1H), 2.36(d, J=14.1 Hz, 1H), 3.37(td, J=13.4, 2.6 Hz, 1H), 4.01(d, J=13.9 Hz, 1H), 5.18(d, J=5.4 Hz, 1H), 7.21(d, J=8.3 Hz, 1H), 7.30-7.46(m, 5H), 7.79(br, 1H), 7.89(br, 1H).

ESI-MS: m/z=495(M+H)$^+$.

Example 3

Synthesis of N-(2-chloro-2'-(trifluoromethoxy)-[1,1'-biphenyl]-4-yl)-1-propionylpiperidine-2-carboxamide

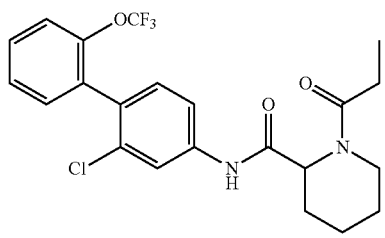

To a dichloromethane (2.0 mL) solution of the compound of Reference Example 3 (0.0300 g, 0.0752 mmol), triethylamine (0.0157 mL, 0.113 mmol) and propionyl chloride (0.00719 mL, 0.0828 mmol) were added at 0° C. and the temperature was raised to room temperature, followed by stirring for 30 minutes. To the reaction solution, methanol was added, and the solution was concentrated under reduced pressure. The residue was purified by column chromatography (silica gel, chloroform/methanol=100/0 to 90/10) to obtain N-(2-chloro-2'-(trifluoromethoxy)-[1,1'-biphenyl]-4-yl)-1-propionylpiperidine-2-carboxamide (hereinafter referred to as the compound of Example 3) (0.0340 g, 0.0747 mmol, 99.4%) as a white solid.

$^1$H-NMR (400 MHz, CDCl$_3$) δ: 1.22(t, J=7.3 Hz, 3H), 1.55(br, 2H), 1.76(br, 2H), 1.97(t, J=13.2 Hz, 1H), 2.30(d, J=12.7 Hz, 1H), 2.48(dq, J=6.6, 2.0 Hz, 2H), 3.12(td, J=13.2, 2.8 Hz, 1H), 3.83(d, J=13.2 Hz, 1H), 5.29(d, J=5.4 Hz, 1H), 7.20(d, J=8.3 Hz, 1H), 7.29-7.36(m, 4H), 7.39-7.45(m, 1H), 7.84(br, 1H), 8.56(br, 1H).

ESI-MS: m/z=455(M+H)$^+$.

Example 4

Synthesis of N-(2-chloro-2'-(trifluoromethoxy)-[1,1'-biphenyl]-4-yl)-1-(2-methoxyacetyl)piperidine-2-carboxamide

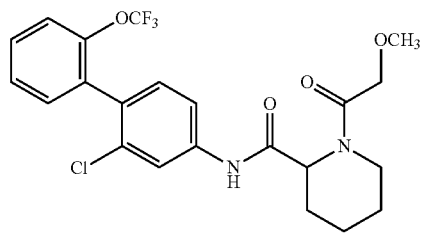 [SMILES: COCC(=O)N1CCCCC1C(=O)Nc1ccc(-c2ccccc2OC(F)(F)F)c(Cl)c1]

To a DMF (0.5 mL) solution of 2-methoxyacetic acid (0.00693 ml, 0.0903 mmol), a DMF (0.5 mL) solution of the compound of Reference Example 3 (0.0300 g, 0.0752 mmol), HATU (0.0343 g, 0.0902 mmol) and diisopropylethylamine (0.0197 mL, 0.113 mmol) were added at room temperature, followed by stirring at the same temperature for 3 hours. To the reaction solution, distilled water was added, and the solution was extracted with a mixed solvent of n-hexane/ethyl acetate=20/80. The organic layer was washed with saturated brine, dried over anhydrous sodium sulfate and filtered, and then the filtrate was concentrated under reduced pressure. The residue was purified by column chromatography (silica gel, n-hexane/ethyl acetate=50/50 to 0/100) to obtain N-(2-chloro-2'-(trifluoromethoxy)-[1,1'-biphenyl]-4-yl)-1-(2-methoxyacetyl)piperidine-2-carboxamide (hereinafter referred to as the compound of Example 4) (0.0266 g, 0.0565 mmol, 74.6%) as a white solid.

$^1$H-NMR (400 MHz, CDCl$_3$) δ: 1.58-2.00(m, 5H), 2.33(d, J=14.4 Hz, 0.8H), 2.48(d, J=12.7 Hz, 0.2H), 2.63(t, J=12.7 Hz, 0.2H), 3.14(t, J=13.0 Hz, 0.8H), 3.48(s, 2.4H), 3.51(s, 0.6H), 3.82(d, J=12.7 Hz, 0.8H), 4.12(d, J=11.7 Hz, 0.2H), 4.18(d, J=13.9 Hz, 0.8H), 4.26(d, J=13.9 Hz, 0.8H), 4.34(d, J=11.7 Hz, 0.2H), 4.52-4.60(m, 0.2H), 4.64-4.68(m, 0.2H), 5.23(d, J=6.1 Hz, 0.8H), 7.20(d, J=8.3 Hz, 1H), 7.28-7.45 (m, 5H), 7.65-7.90(m, 1H), 8.46(br, 0.8H), 8.57(br, 0.2H).

ESI-MS: m/z=471(M+H)$^+$.

Example 5

Synthesis of N-(2-chloro-2'-(trifluoromethoxy)-[1,1'-biphenyl]-4-yl)-1-(2-hydroxyacetyl)piperidine-2-carboxamide

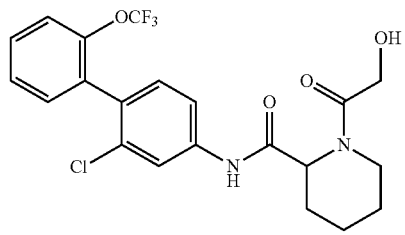 [SMILES: O=C(Nc1ccc(-c2ccccc2OC(F)(F)F)c(Cl)c1)C1CCCCN1C(=O)CO]

According to the same procedure as in Example 4, except that glycolic acid was used in place of 2-methoxyacetic acid, N-(2-chloro-2'-(trifluoromethoxy)-[1,1'-biphenyl]-4-yl)-1-(2-hydroxyacetyl)piperidine-2-carboxamide (hereinafter referred to as the compound of Example 5) (0.0114 g, 0.0250 mmol, 33.2%) was obtained as a white solid.

$^1$H-NMR (400 MHz, CDCl$_3$) δ: 1.48-1.55(m, 1H), 1.63-1.71(m, 1H), 1.75-1.85(m, 2H), 1.91-2.02(m, 1H), 2.32(d, J=13.4 Hz, 1H), 3.17-3.25(m, 1H), 3.43-3.53(m, 2H), 4.28-4.32(m, 2H), 5.26(d, J=5.6 Hz, 1H), 7.22(d, J=8.3 Hz, 1H), 7.30-7.45(m, 5H), 7.77(br, 1H), 8.14(br, 1H).

ESI-MS: m/z=457(M+H)$^+$.

Example 6

Synthesis of N-(2-chloro-2'-(trifluoromethoxy)-[1,1'-biphenyl]-4-yl)-1-(2-(dimethylamino)acetyl)piperidine-2-carboxamide

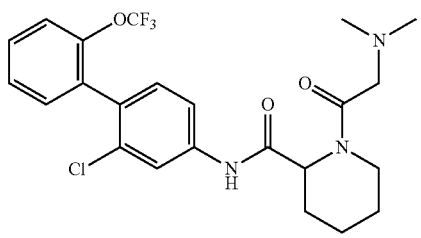 [SMILES: CN(C)CC(=O)N1CCCCC1C(=O)Nc1ccc(-c2ccccc2OC(F)(F)F)c(Cl)c1]

According to the same procedure as in Example 4, except that N,N-dimethylglycine hydrochloride was used in place of 2-methoxyacetic acid, N-(2-chloro-2'-(trifluoromethoxy)-[1,1'-biphenyl]-4-yl)-1-(2-(dimethylamino)acetyl)piperidine-2-carboxamide (hereinafter referred to as the compound of Example 6) (0.0273 g, 0.0564 mmol, 90.0%) was obtained as a white solid.

$^1$H-NMR (400 MHz, CDCl$_3$) δ: 1.40-2.20(m, 6H), 2.34(s, 3H), 2.47-2.50(m, 3.4H), 2.56-2.64(m, 0.4H), 2.92(d, J=12.6 Hz, 0.6H), 3.06-3.14(m, 0.4H), 3.24(s, 0.6H), 3.67(d, J=12.6 Hz, 0.6H), 4.03-4.07(m, 0.4H), 4.54-4.62(m, 1.2H), 5.24-5.27(m, 0.4H), 7.19-7.23(m, 1H), 7.30-7.46(m, 5H), 7.73-7.75(m, 1H), 8.53(br, 0.4H), 10.69(br, 0.6H).

ESI-MS: m/z=484(M+H)$^+$.

Example 7

Synthesis of N-(2-chloro-2'-(trifluoromethoxy)-[1,1'-biphenyl]-4-yl)-1-(2,2-difluoroacetyl)piperidine-2-carboxamide

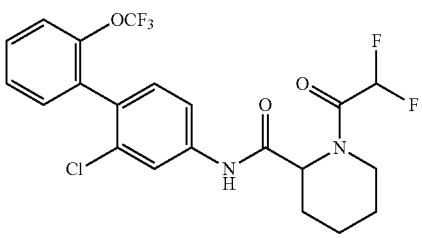 [SMILES: O=C(Nc1ccc(-c2ccccc2OC(F)(F)F)c(Cl)c1)C1CCCCN1C(=O)C(F)F]

According to the same procedure as in Example 4, except that difluoroacetic acid was used in place of 2-methoxyacetic acid, N-(2-chloro-2'-(trifluoromethoxy)-[1,1'-biphenyl]-4-yl)-1-(2,2-difluoroacetyl)piperidine-2-carboxamide (hereinafter referred to as the compound of Example 7) (0.0212 g, 0.0444 mmol, 59.1%) was obtained as a white solid.

$^1$H-NMR (400 MHz, DMSO-D$_6$) δ: 1.40-1.80(m, 5.0H), 2.21-2.24(m, 0.7H), 2.29-2.34(m, 0.3H), 2.65-2.68(m, 0.3H), 3.46-3.55(m, 0.7H), 3.82-3.88(m, 0.7H), 4.28-4.34(m, 0.3H), 4.79-4.81(m, 0.3H), 5.07-5.10(m, 0.7H), 6.73(t, J=52.6 Hz, 0.3H), 6.83(t, J=52.7 Hz, 0.7H), 7.32(d, J=8.3 Hz, 1H), 7.39-7.43(m, 1H), 7.45-7.51(m, 2H), 7.53-7.60(m, 2H), 7.90-7.93(m, 1H), 10.19(br, 0.3H), 10.25(br, 0.7H).

ESI-MS: m/z=477(M+H)$^+$.

Example 8

Synthesis of N-(2-chloro-2'-(trifluoromethoxy)-[1,1'-biphenyl]-4-yl)-1-(2-(trifluoromethoxy)acetyl)piperidine-2-carboxamide

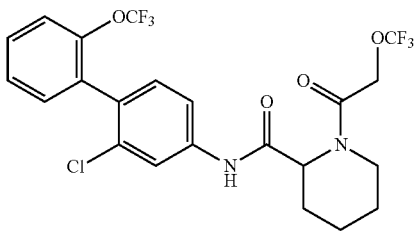 [SMILES: O=C(Nc1ccc(-c2ccccc2OC(F)(F)F)c(Cl)c1)C1CCCCN1C(=O)COC(F)(F)F]

According to the same procedure as in Example 4, except that 2-trifluoromethoxyacetic acid was used in place of 2-methoxyacetic acid, N-(2-chloro-2'-(trifluoromethoxy)-[1,1'-biphenyl]-4-yl)-1-(2-(trifluoromethoxy)acetyl)piperidine-2-carboxamide (hereinafter referred to as the compound of Example 8) (0.00890 g, 0.0170 mmol, 16.9%) was obtained as a white solid.

$^1$H-NMR (400 MHz, CDCl$_3$) δ: 1.55-1.71(m, 2H), 1.76-1.84(m, 2H), 1.94-2.03(m, 1H), 2.32(d, J=14.5 Hz, 1H), 3.29(td, J=13.1, 2.7 Hz, 1H), 3.67(d, J=12.7 Hz, 1H), 4.68-4.76(m, 2H), 5.22(d, J=5.4 Hz, 1H), 7.21-7.45(m, 6H), 7.81(br, 1H), 8.26(s, 1H).

ESI-MS: m/z=523(M−H)$^−$.

Reference Example 4

Synthesis of tert-butyl (2-(2-((2-chloro-2'-(trifluoromethoxy)-[1,1'-biphenyl]-4-yl)carbamoyl)piperidin-1-yl)-2-oxoethyl)carbamate

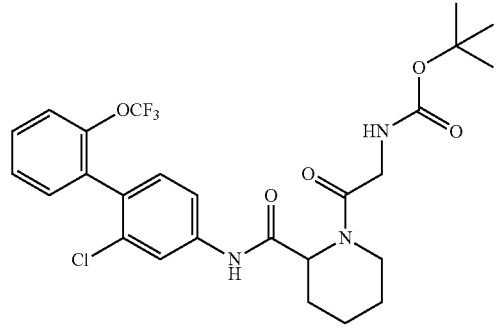 [SMILES: CC(C)(C)OC(=O)NCC(=O)N1CCCCC1C(=O)Nc1ccc(-c2ccccc2OC(F)(F)F)c(Cl)c1]

According to the same procedure as in Example 4, except that 2-((tert-butoxycarbonyl)amino)acetic acid was used in place of 2-methoxyacetic acid, tert-butyl (2-(2-((2-chloro-2'-(trifluoromethoxy)-[1,1'-biphenyl]-4-yl)carbamoyl)piperidin-1-yl)-2-oxoethyl)carbamate (hereinafter referred to as the compound of Reference Example 4) (0.116 g, 0.208 mmol, quantitative) was obtained as a white solid.

$^1$H-NMR (400 MHz, CDCl$_3$) δ: 1.46(s, 9H), 1.45-1.90(m, 5H), 2.38(d, J=13.2 Hz, 1H), 3.21(t, J=12.1 Hz, 1H), 3.75(d, J=13.9 Hz, 1H), 3.95(dd, J=16.7, 5.0 Hz, 1H), 4.09-4.15(m, 1H), 5.32(d, J=4.9 Hz, 1H), 5.42(br, 1H), 7.21(d, J=8.3 Hz, 1H), 7.29-7.36(m, 3H), 7.40-7.45(m, 1H), 7.52(br, 1H), 7.80(br, 1H), 8.31(br, 1H).

ESI-MS: m/z=556(M+H)$^+$.

Reference Example 5

Synthesis of 1-(2-aminoacetyl)-N-(2-chloro-2'-(trifluoromethoxy)-[1,1'-biphenyl]-4-yl)piperidine-2-carboxamide

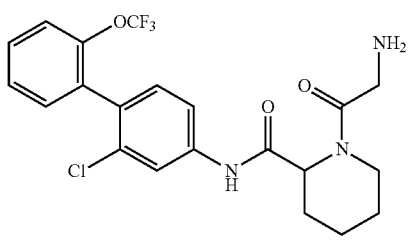 [SMILES: NCC(=O)N1CCCCC1C(=O)Nc1ccc(-c2ccccc2OC(F)(F)F)c(Cl)c1]

To a dichloromethane (1.0 mL) solution of the compound of Reference Example 4 (0.115 g, 0.207 mmol), trifluoroacetic acid (0.112 mL, 1.45 mmol) was added at room temperature, followed by stirring at the same temperature for 15 hours. The reaction solution was concentrated under reduced pressure, neutralized with an aqueous potassium carbonate solution, and then extracted with chloroform. The organic layer was dried over anhydrous sodium sulfate and filtered, and then the filtrate was concentrated under reduced pressure. The residue was purified by column chromatography (amine silica gel, chloroform/methanol=100/0 to 96/4) to obtain 1-(2-aminoacetyl)-N-(2-chloro-2'-(trifluoromethoxy)-[1,1'-biphenyl]-4-yl)piperidine-2-carboxamide (hereinafter referred to as the compound of Reference Example 5) (0.0613 g, 0.134 mmol, 65.0%) as a white solid.

$^1$H-NMR (400 MHz, CDCl$_3$) δ: 1.45-1.63(m, 2H), 1.70-1.81(m, 2H), 1.89-1.99(m, 1H), 2.31(d, J=14.0 Hz, 1H), 3.16(td, J=14.0, 2.3 Hz, 1H), 3.60(d, J=1.0 Hz, 2H), 3.68(d, J=14.0 Hz, 1H), 5.27(d, J=5.4 Hz, 1H), 7.21(d, J=8.3 Hz, 1H), 7.30-7.45(m, 5H), 7.77(br, 1H), 8.39(br, 1H).

ESI-MS: m/z=456(M+H)$^+$.

Reference Example 6

Synthesis of tert-butyl (2-(2-((2-chloro-2'-(trifluoromethoxy)-[1,1'-biphenyl]-4-yl)carbamoyl)piperidin-1-yl)-2-oxoethyl)(methyl)carbamate

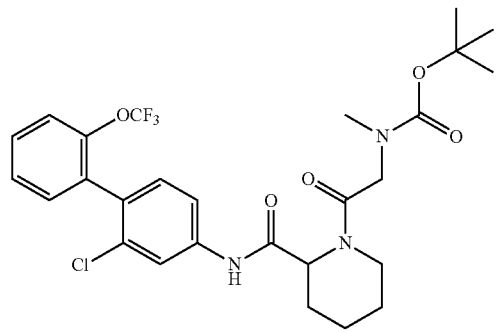 [SMILES: CN(CC(=O)N1CCCCC1C(=O)Nc1ccc(-c2ccccc2OC(F)(F)F)c(Cl)c1)C(=O)OC(C)(C)C]

According to the same procedure as in Example 4, except that N-(tert-butoxycarbonyl)-N-methylglycine was used in place of 2-methoxyacetic acid, tert-butyl (2-(2-((2-chloro-2'-(trifluoromethoxy)-[1,1'-biphenyl]-4-yl)carbamoyl)piperidin-1-yl)-2-oxoethyl)(methyl)carbamate (hereinafter referred to as the compound of Reference Example 6) (0.132 g, 0.232 mmol, 92.6%) was obtained as a white solid.

$^1$H-NMR (400 MHz, CDCl$_3$) δ: 1.57(s, 9H), 1.38-1.80(m, 5H), 2.46-2.53(m, 1H), 3.05(s, 3H), 3.15-3.22(m, 1H), 3.66(d, J=15.7 Hz, 1H), 3.77-3.84(m, 1H), 4.41(d, J=15.7 Hz, 1H), 5.41-5.44(m, 1H), 7.19(d, J=8.3 Hz, 1H), 7.28-7.44(m, 4H), 7.70(br, 1H), 7.88(br, 1H), 8.61(br, 1H).

ESI-MS: m/z=571(M+H)$^+$.

Example 9

Synthesis of 1-(2-acetamideacetyl)-N-(2-chloro-2'-(trifluoromethoxy)-[1,1'-biphenyl]-4-yl)piperidine-2-carboxamide

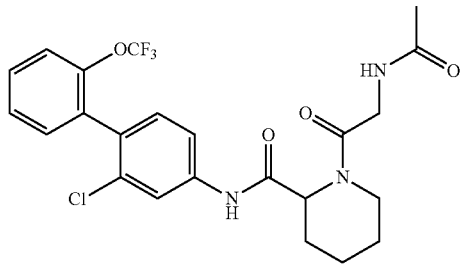

According to the same procedure as in Example 3, except that the compound of Reference Example 5 was used in place of the compound of Reference Example 3 and acetyl chloride was used in place of propionyl chloride, 1-(2-acetamideacetyl)-N-(2-chloro-2'-(trifluoromethoxy)-[1,1'-biphenyl]-4-yl)piperidine-2-carboxamide (hereinafter referred to as the compound of Example 9) (0.0274 g, 0.0550 mmol, 80.9%) was obtained as a white solid.

$^1$H-NMR (400 MHz, CDCl$_3$) δ: 1.50-1.90(m, 5H), 2.09(s, 3H), 2.37(d, J=14.4 Hz, 1H), 3.25(td, J=13.0, 2.4 Hz, 1H), 3.75(d, J=12.4 Hz, 1H), 4.11(dd, J=17.2, 4.0 Hz, 1H), 4.21(dd, J=17.2, 4.0 Hz, 1H), 5.29(d, J=5.1 Hz, 1H), 6.53(br,

1H), 7.21(d, J=8.5 Hz, 1H), 7.29-7.37(m, 3H), 7.40-7.48(m, 2H), 7.80(br, 1H), 8.26(br, 1H).

ESI-MS: m/z=498(M+H)+.

Example 10

Synthesis of N-(2-chloro-2'-(trifluoromethoxy)-[1,1'-biphenyl]-4-yl)-1-(2-(methyl sulfonamide)acetyl)piperidine-2-carboxamide

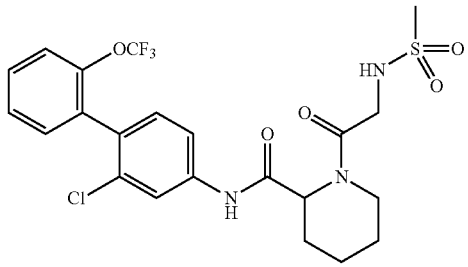 [SMILES: CS(=O)(=O)NCC(=O)N1CCCCC1C(=O)Nc1ccc(-c2ccccc2OC(F)(F)F)c(Cl)c1]

According to the same procedure as in Example 3, except that the compound of Reference Example 5 was used in place of the compound of Reference Example 3 and methanesulfonyl chloride was used in place of propionyl chloride, N-(2-chloro-2'-(trifluoromethoxy)-[1,1'-biphenyl]-4-yl)-1-(2-(methylsulfonamide)acetyl)piperidine-2-carboxamide (hereinafter referred to as the compound of Example 10) (0.0202 g, 0.0378 mmol, 79.2%) was obtained as a white solid.

1H-NMR (400 MHz, CDCl3) δ: 1.52-1.95(m, 5H), 2.32(d, J=14.1 Hz, 1H), 3.02(s, 3H), 3.33(t, J=12.8 Hz, 1H), 3.64(d, J=13.0 Hz, 1H), 4.08(d, J=4.6 Hz, 2H), 5.25(d, J=4.6 Hz, 1H), 5.48(br, 1H), 7.22(d, J=8.3 Hz, 1H), 7.29-7.45(m, 5H), 7.81(br, 1H), 8.09(br, 1H).

ESI-MS: m/z=534(M+H)+.

Example 11

Synthesis of N-(2-chloro-2'-(trifluoromethoxy)-[1,1'-biphenyl]-4-yl)-1-(2-(methylamino)acetyl)piperidine-2-carboxamide

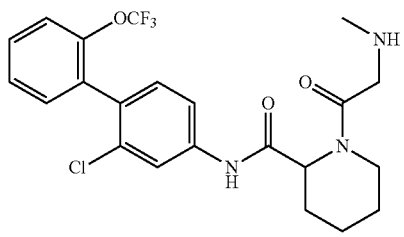

According to the same procedure as in Reference Example 5, except that the compound of Reference Example 6 was used in place of the compound of Reference Example 4, N-(2-chloro-2'-(trifluoromethoxy)-[1,1'-biphenyl]-4-yl)-1-(2-(methylamino)acetyl)piperidine-2-carboxamide (hereinafter referred to as the compound of Example 11) (0.0799 g, 0.170 mmol, 73.4%) was obtained as a white solid.

1H-NMR (400 MHz, CDCl3) δ: 1.26-1.76(m, 5H), 1.90-2.06(m, 1H), 2.28-2.42(m, 1H), 2.50(s, 2.4H), 2.60-2.63(m, 0.8H), 3.15(t, J=12.2 Hz, 0.8H), 3.43(d, J=12.7 Hz, 0.2H), 3.52(s, 1.6H), 3.70-3.76(m, 1H), 4.58-4.63(m, 0.4H), 5.28(d, J=4.9 Hz, 0.8H), 7.19-7.23(m, 1H), 7.30-7.45(m, 5H), 7.75-7.77(m, 1H), 8.44(s, 0.8H), 10.49(s, 0.2H).

ESI-MS: m/z=470(M+H)+.

Example 12

Synthesis of N-(2-chloro-2'-(trifluoromethoxy)-[1,1'-biphenyl]-4-yl)-1-(2-(N-methylacetamide)acetyl)piperidine-2-carboxamide

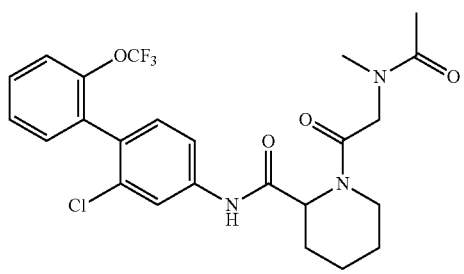 [SMILES: CC(=O)N(C)CC(=O)N1CCCCC1C(=O)Nc1ccc(-c2ccccc2OC(F)(F)F)c(Cl)c1]

According to the same procedure as in Example 3, except that the compound of Example 11 was used in place of the compound of Reference Example 3 and acetyl chloride was used in place of propionyl chloride, N-(2-chloro-2'-(trifluoromethoxy)-[1,1'-biphenyl]-4-yl)-1-(2-(N-methylacetamide)acetyl)piperidine-2-carboxamide (hereinafter referred to as the compound of Example 12) (0.0261 g, 0.0510 mmol, 95.8%) was obtained as a white solid.

1H-NMR (400 MHz, CDCl3) δ: 1.48-1.76(m, 5H), 2.20(s, 3H), 2.50-2.65(m, 1H), 3.24(s, 2.1H), 3.30(s, 0.9H), 3.20-3.31(m, 1H), 3.34(d, J=15.0 Hz, 0.3H), 3.63(d, J=15.0 Hz, 0.7H), 3.83-3.89(m, 0.7H), 4.60(d, J=15.0 Hz, 0.7H), 4.64-4.70(m, 0.6H), 4.78(d, J=15.0 Hz, 0.3H), 5.41(d, J=4.5 Hz, 0.7H), 7.20-7.22(m, 1H), 7.30-7.35(m, 3H), 7.39-7.44(m, 1H), 7.60-7.75(m, 0.7H), 7.77(dd, J=8.4, 2.0 Hz, 0.3H), 7.98-8.07(m, 0.7H), 8.14(d, J=1.8 Hz, 0.3H), 8.64(br, 0.7H), 9.63(br, 0.3H).

ESI-MS: m/z=512(M+H)+.

Example 13

Synthesis of N-(2-chloro-2'-(trifluoromethoxy)-[1,1'-biphenyl]-4-yl)-1-(2-(N-methylmethylsulfonamide)acetyl)piperidine-2-carboxamide

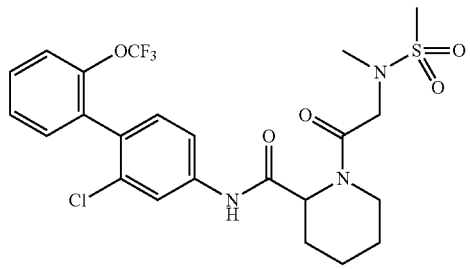

According to the same procedure as in Example 3, except that the compound of Example 11 was used in place of the compound of Reference Example 3 and methanesulfonyl chloride was used in place of propionyl chloride, N-(2-chloro-2'-(trifluoromethoxy)-[1,1'-biphenyl]-4-yl)-1-(2-(N-methylmethylsulfonamide)acetyl)piperidine-2-carboxamide (hereinafter referred to as the compound of Example 13) (0.0264 g, 0.0482 mmol, 90.6%) was obtained as a white solid.

$^1$H-NMR (400 MHz, CDCl$_3$) δ: 1.52-1.89(m, 5H), 2.35-2.38(m, 1H), 3.03-3.07(m, 6H), 3.20-3.31(m, 1H), 3.67-3.76(m, 1H), 4.16-4.27(m, 2H), 5.25-5.26(m, 1H), 7.21-7.23(m, 1H), 7.30-7.45(m, 5H), 7.83(s, 1H), 8.22(br, 1H).
ESI-MS: m/z=548(M+H)$^+$.

Example 14

Synthesis of N-(2-chloro-2'-(trifluoromethoxy)-[1,1'-biphenyl]-4-yl)-1-(ethylsulfonyl)piperidine-2-carboxamide

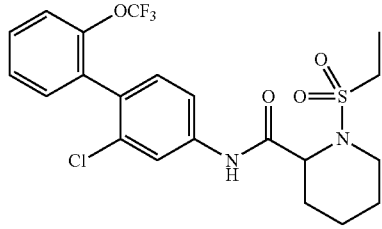

According to the same procedure as in Example 3, except that ethanesulfonyl chloride was used in place of propionyl chloride, N-(2-chloro-2'-(trifluoromethoxy)-[1,1'-biphenyl]-4-yl)-1-(ethylsulfonyl)piperidine-2-carboxamide (hereinafter referred to as the compound of Example 14) (0.0660 g, 0.134 mmol, 99.3%) was obtained as a white solid.

$^1$H-NMR (400 MHz, CDCl$_3$) δ: 1.47(t, J=7.4 Hz, 3H), 1.58-1.68(m, 2H), 1.69-1.84(m, 3H), 2.59(d, J=12.4 Hz, 1H), 3.06-3.21(m, 4H), 3.88(d, J=12.0 Hz, 1H), 4.56(d, J=8.3 Hz, 1H), 7.24(d, J=8.3 Hz, 1H), 7.31-7.38(m, 3H), 7.40-7.50(m, 2H), 7.85(s, 1H), 8.53(br, 1H).
ESI-MS: m/z=491(M+H)$^+$.

Example 15

Synthesis of N-(2-chloro-2'-(trifluoromethoxy)-[1,1'-biphenyl]-4-yl)-1-(methylsulfonyl)piperidine-2-carboxamide

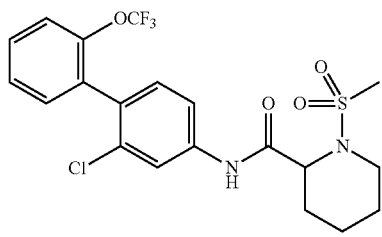 [SMILES: CS(=O)(=O)N1CCCCC1C(=O)Nc1ccc(-c2ccccc2OC(F)(F)F)c(Cl)c1]

According to the same procedure as in Example 3, except that methanesulfonyl chloride was used in place of propionyl chloride, N-(2-chloro-2'-(trifluoromethoxy)-[1,1'-biphenyl]-4-yl)-1-(methylsulfonyl)piperidine-2-carboxamide (hereinafter referred to as the compound of Example 15) (0.0800 g, 0.168 mmol, 66.9%) was obtained as a white solid.

$^1$H-NMR (400 MHz, CDCl$_3$) δ: 1.47-1.61(m, 1H), 1.62-1.81(m, 4H), 2.45(d, J=10.4 Hz, 1H), 3.04(s, 3H), 3.23(td, J=13.3, 2.4 Hz, 1H), 3.93(t, J=7.0 Hz, 1H), 4.64(br, 1H), 7.25(d, J=8.5 Hz, 1H), 7.30-7.38(m, 3H), 7.43(dt, J=10.8, 3.7 Hz, 2H), 7.84(d, J=2.2 Hz, 1H), 8.29(br, 1H).
ESI-MS: m/z=477(M+H)$^+$.

Example 16

Synthesis of N-(2-chloro-2'-(trifluoromethoxy)-[1,1'-biphenyl]-4-yl)-1-formylpiperidine-2-carboxamide

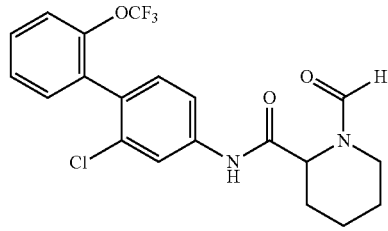 [SMILES: O=CN1CCCCC1C(=O)Nc1ccc(-c2ccccc2OC(F)(F)F)c(Cl)c1]

To a dichloromethane (1.0 mL) solution of the compound of Reference Example 3 (0.0400 g, 0.100 mmol), ethyl formate (0.567 mL, 7.02 mmol) was added at 0° C. and the temperature was raised to 90° C., followed by stirring for 18 hours. The reaction solution was concentrated under reduced pressure and the residue was purified by column chromatography (silica gel, chloroform/methanol=100/0 to 90/10) to obtain N-(2-chloro-2'-(trifluoromethoxy)-[1,1'-biphenyl]-4-yl)-1-formylpiperidine-2-carboxamide (hereinafter referred to as the compound of Example 16) (0.0300 g, 0.0703 mmol, 70.1%) as a white solid.

$^1$H-NMR (400 MHz, CDCl$_3$) δ: 1.42-1.64(m, 2H), 1.82(d, J=10.0 Hz, 2H), 1.95(dt, J=8.8, 4.3 Hz, 1H), 2.35(d, J=13.9 Hz, 1H), 3.29(td, J=13.2, 2.8 Hz, 1H), 3.63(d, J=9.5 Hz, 1H), 5.12(d, J=5.6 Hz, 1H), 7.21(d, J=8.3 Hz, 1H), 7.28-7.45(m, 5H), 7.80(br, 1H), 8.21(d, J=9.2 Hz, 1H), 8.32(br, 1H).
ESI-MS: m/z=427(M+H)$^+$.

Example 17

Synthesis of N$^2$-(2-chloro-2'-(trifluoromethoxy)-[1,1'-biphenyl]-4-yl)piperidine-1,2-dicarboxamide

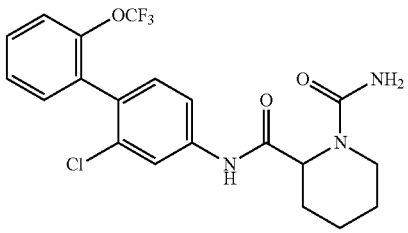

To a dichloromethane (3.0 mL) solution of the compound of Reference Example 3 (0.100 g, 0.251 mmol), trimethylsilyl isocyanate (0.0333 mL, 0.251 mmol) and triethylamine (0.0349 mL, 0.251 mmol) were added at 0° C. and the temperature was raised to room temperature, followed by stirring for 72 hours. To the reaction solution, methanol was added, and the solution was concentrated under reduced pressure. The residue was purified by column chromatography (silica gel, chloroform) to obtain N²-(2-chloro-2'-(trifluoromethoxy)-[1,1'-biphenyl]-4-yl)piperidine-1,2-dicarboxamide (hereinafter referred to as the compound of Example 17) (0.0300 g, 0.0679 mmol, 27.1%) as a white solid.

¹H-NMR (400 MHz, CDCl₃) δ: 1.50-1.68(m, 2H), 1.73 (br, 2H), 1.81-1.92(m, 1H), 2.30(d, J=12.9 Hz, 1H), 3.21(dt, J=12.8, 2.6 Hz, 1H), 3.52(d, J=13.2 Hz, 1H), 4.81(br, 2H), 5.03(d, J=4.6 Hz, 1H), 7.20(d, J=8.3 Hz, 1H), 7.29-7.37(m, 3H), 7.42(dt, J=10.8, 3.8 Hz, 2H), 7.81(br, 1H), 8.95(br, 1H).

ESI-MS: m/z=442(M+H)⁺.

Example 18

Synthesis of N²-(2-chloro-2'-(trifluoromethoxy)-[1,1'-biphenyl]-4-yl)-N¹,N¹-dimethylpiperidine-1,2-dicarboxamide

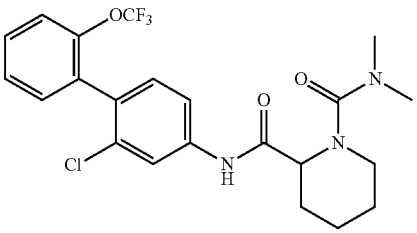 [SMILES: CN(C)C(=O)N1CCCCC1C(=O)Nc1ccc(-c2ccccc2OC(F)(F)F)c(Cl)c1]

According to the same procedure as in Example 3, except that dimethylcarbamoyl chloride was used in place of propionyl chloride, N²-(2-chloro-2'-(trifluoromethoxy)-[1,1'-biphenyl]-4-yl)-N¹,N¹-dimethylpiperidine-1,2-dicarboxamide (hereinafter referred to as the compound of Example 18) (0.0231 g, 0.0492 mmol, 65.4%) was obtained as a white solid.

¹H-NMR (400 MHz, CDCl₃) δ: 1.48-1.78(m, 4H), 1.92-2.05(m, 1H), 2.27-2.35(m, 1H), 2.94(s, 6H), 2.87-2.99(m, 1H), 3.40-3.46(m, 1H), 4.47-4.51(m, 1H), 7.20(d, J=8.6 Hz, 1H), 7.30-8.00(m, 6H), 10.60(br, 1H).

ESI-MS: m/z=470(M+H)⁺.

Example 19

Synthesis of methyl 2-((2-chloro-2'-(trifluoromethoxy)-[1,1'-biphenyl]-4-yl)carbamoyl)piperidine-1-carboxylate

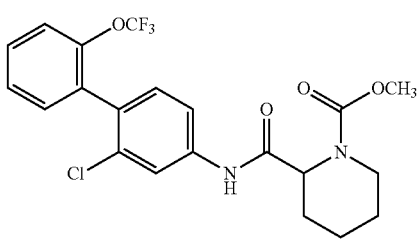 [SMILES: COC(=O)N1CCCCC1C(=O)Nc1ccc(-c2ccccc2OC(F)(F)F)c(Cl)c1]

According to the same procedure as in Example 3, except that methyl chloroformate was used as propionyl chloride, methyl 2-((2-chloro-2'-(trifluoromethoxy)-[1,1'-biphenyl]-4-yl)carbamoyl)piperidine-1-carboxylate (hereinafter referred to as the compound of Example 19) (0.0316 g, 0.0692 mmol, 92.0%) was obtained as a white solid.

¹H-NMR (400 MHz, CDCl₃) δ: 1.46-1.78(m, 5H), 2.30-2.41(m, 1H), 2.92(t, J=12.1 Hz, 1H), 3.81(s, 3H), 4.05-4.20 (br, 1H), 4.93(d, J=4.6 Hz, 1H), 7.23(d, J=8.5 Hz, 1H), 7.31-7.45(m, 5H), 7.74-7.86(m, 1H), 8.21(br, 1H).

ESI-MS: m/z=457(M+H)⁺.

Reference Example 7

Synthesis of tert-butyl (R)-2-((2-chloro-2'-(trifluoromethoxy)-[1,1'-biphenyl]-4-yl)carbamoyl)piperidine-1-carboxylate

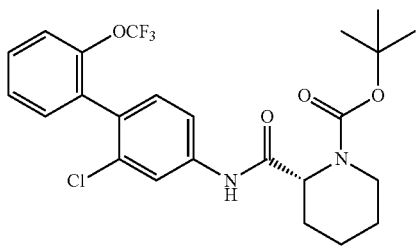 [SMILES: CC(C)(C)OC(=O)N1CCCC[C@@H]1C(=O)Nc1ccc(-c2ccccc2OC(F)(F)F)c(Cl)c1]

To a DMF (18 mL) solution of (R)-(+)-1-(tert-butoxycarbonyl)piperidine-2-carboxylic acid (0.840 g, 3.66 mmol), the compound of Reference Example 1 (1.05 g, 3.66 mmol), HATU (1.53 g, 4.03 mmol), and diisopropylethylamine (0.768 mL, 4.40 mmol) were added at room temperature, followed by stirring at the same temperature for 18 hours. To the reaction solution, distilled water was added, and the solution was extracted with ethyl acetate. The organic layer was washed with saturated brine, dried over anhydrous sodium sulfate and filtered, and then the filtrate was concentrated under reduced pressure. The residue was purified by column chromatography (silica gel, n-hexane/ethyl acetate=80/20) to obtain tert-butyl (R)-2-((2-chloro-2'-(trifluoromethoxy)-[1,1'-biphenyl]-4-yl)carbamoyl)piperidine-1-carboxylate (hereinafter referred to as the compound of Reference Example 7) (1.60 g, 3.20 mmol, 87.3%) as a white solid.

¹H-NMR (400 MHz, CDCl₃) δ: 1.43-1.51(m, 2H), 1.53(s, 9H), 1.60-1.75(m, 3H), 2.35(d, J=12.7 Hz, 1H), 2.80-2.89 (m, 1H), 4.03-4.13(m, 1H), 4.86-4.89(m, 1H), 7.22(d, J=8.3 Hz, 1H), 7.29-7.45(m, 6H), 7.80(br, 1H).

ESI-MS: m/z=499(M+H)⁺.

Reference Example 8

Synthesis of (R)-N-(2-chloro-2'-(trifluoromethoxy)-[1,1'-biphenyl]-4-yl)piperidine-2-carboxamide

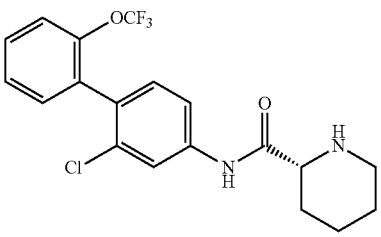 [SMILES: O=C(Nc1ccc(-c2ccccc2OC(F)(F)F)c(Cl)c1)[C@H]1CCCCN1]

To a dichloromethane (30 mL) solution of the compound of Reference Example 7 (1.60 g, 3.21 mmol), trifluoroacetic acid (8.02 mL, 104 mmol) was added at room temperature, followed by stirring at the same temperature for 2 hours. To the reaction solution, distilled water was added, and the solution was extracted with chloroform. The aqueous layer was neutralized by adding an aqueous 1M sodium hydroxide solution and then extracted with chloroform. The organic layer was washed with distilled water and saturated brine, dried over anhydrous sodium sulfate, and filtered, and then the filtrate was concentrated under reduced pressure to obtain (R)-N-(2-chloro-2'-(trifluoromethoxy)-[1,1'-biphenyl]-4-yl)piperidine-2-carboxamide (hereinafter referred to as the compound of Reference Example 8) (1.13 g, 2.84 mmol, 88.6%) as a white solid.

$^1$H-NMR (400 MHz, CDCl$_3$) δ: 1.53(ddd, J=36.8, 17.9, 8.8 Hz, 4H), 1.78-1.86(m, 1H), 2.00-2.07(m, 1H), 2.74-2.82 (m, 1H), 3.03-3.10(m, 1H), 3.38(dd, J=9.6, 3.5 Hz, 1H), 7.23(d, J=8.3 Hz, 1H), 7.31-7.37(m, 3H), 7.40-7.45(m, 1H), 7.53(dd, J=8.3, 2.0 Hz, 1H), 7.82(d, J=2.2 Hz, 1H), 9.02(br, 1H).

ESI-MS: m/z=399(M+H)$^+$.

Example 20

Synthesis of (R)-1-acetyl-N-(2-chloro-2'-(trifluoromethoxy)-[1,1'-biphenyl]-4-yl)piperidine-2-carboxamide

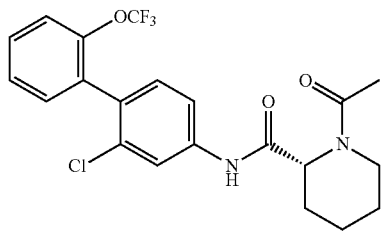

To a dichloromethane (36 mL) solution of the compound of Reference Example 8 (1.43 g, 3.59 mmol), triethylamine (0.750 mL, 5.38 mmol) and acetic anhydride (0.338 mL, 3.59 mmol) were added at 0° C. and the temperature was raised to room temperature, followed by stirring for 30 minutes. To the reaction solution, distilled water was added, and the solution was extracted with chloroform. The organic layer was washed with distilled water and saturated brine, dried over anhydrous sodium sulfate and filtered, and then the filtrate was concentrated under reduced pressure. The residue was purified by column chromatography (silica gel, chloroform/methanol=95/5) to obtain (R)-1-acetyl-N-(2-chloro-2'-(trifluoromethoxy)-[1,1'-biphenyl]-4-yl)piperidine-2-carboxamide (hereinafter referred to as the compound of Example 20) (1.02 g, 2.32 mmol, 64.6%) as a white solid. As a result of analysis using a chiral column, the retention time of the thus obtained compound of Example 20 was 32.8 minutes, and the optical purity at that time was 99.0% ee. The analysis conditions using the chiral column are as follows.

Measurement equipment; High-performance liquid chromatograph LC-2010CHT, manufactured by Shimadzu Corporation
Column; CHIRALCEL OD-RH 0.46 cmφ×15 cm, particle size of 5 μm, manufactured by Daicel Chemical Industries Ltd.
Column temperature; 40° C.
Mobile phase; (Solution A) aqueous 20 mM potassium dihydrogen phosphate solution, (Solution B) acetonitrile
Composition of mobile phase; Solution A: Solution B=60:40 to 50:50 (0 to 40 minutes, linear gradient)
Solution A: Solution B=50:50 to 60:40 (40 to 41 minutes, linear gradient)
Solution A: Solution B=60:40 (41 to 50 minutes)
Flow rate; 0.5 mL/minute
Detection; UV (210 nm)

$^1$H-NMR (400 MHz, CDCl$_3$) δ: 1.46-1.63(m, 1H), 1.67(d, J=7.8 Hz, 1H), 1.89-2.02(m, 2H), 2.22(s, 3H), 2.29(d, J=12.9 Hz, 1H), 3.22(t, J=13.2 Hz, 1H), 3.78(d, J=12.7 Hz, 1H), 5.29(d, J=5.1 Hz, 1H), 7.20(d, J=8.3 Hz, 1H), 7.29-7.37(m, 3H), 7.40-7.44(m, 2H), 7.80(br, 1H), 8.65(br, 1H).

ESI-MS: m/z=441(M+H)$^+$.

Example 21

Synthesis of (R)-N-(2-chloro-2'-(trifluoromethoxy)-[1,1'-biphenyl]-4-yl)-1-(methylsulfonyl)piperidine-2-carboxamide

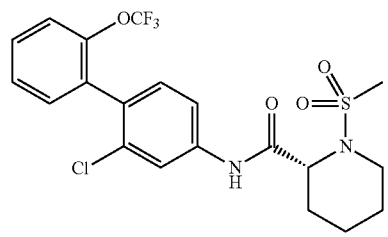 [SMILES: CS(=O)(=O)N1CCCC[C@@H]1C(=O)Nc1ccc(-c2ccccc2OC(F)(F)F)c(Cl)c1]

According to the same procedure as in Example 3, except that the compound of Reference Example 8 was used in place of the compound of Reference Example 3 and methanesulfonyl chloride was used in place of propionyl chloride, (R)-N-(2-chloro-2'-(trifluoromethoxy)-[1,1'-biphenyl]-4-yl)-1-(methylsulfonyl)piperidine-2-carboxamide (hereinafter referred to as the compound of Example 21) (0.0600 g, 0.126 mmol, 99.0%) was obtained as a white solid.

$^1$H-NMR (400 MHz, CDCl$_3$) δ: 1.47-1.61(m, 1H), 1.62-1.81(m, 4H), 2.45(d, J=10.4 Hz, 1H), 3.04(s, 3H), 3.23(td, J=13.3, 2.4 Hz, 1H), 3.93(t, J=7.0 Hz, 1H), 4.64(br, 1H), 7.25(d, J=8.5 Hz, 1H), 7.30-7.38(m, 3H), 7.43(dt, J=10.8, 3.7 Hz, 2H), 7.84(d, J=2.2 Hz, 1H), 8.29(br, 1H).

ESI-MS: m/z=477(M+H)$^+$.

Example 22

Synthesis of (R)-N$^2$-(2-chloro-2'-(trifluoromethoxy)-[1,1'-biphenyl]-4-yl)piperidine-1,2-dicarboxamide

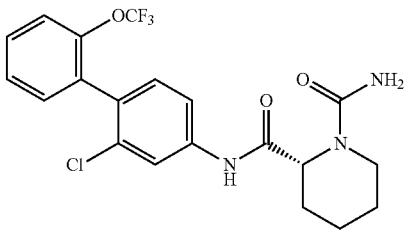 [SMILES: NC(=O)N1CCCC[C@@H]1C(=O)Nc1ccc(-c2ccccc2OC(F)(F)F)c(Cl)c1]

To a dichloromethane (30 mL) solution of the compound of Reference Example 8 (3.00 g, 7.52 mmol), trimethylsilyl isocyanate (2.00 mL, 15.04 mmol) and triethylamine (1.05 mL, 7.57 mmol) were added at 0° C. and the temperature was raised to room temperature, followed by stirring for 18 hours. To the reaction solution, methanol was added, and the solution was concentrated under reduced pressure. The residue was purified by column chromatography (silica gel, chloroform) to obtain (R)-$N^2$-(2-chloro-2'-(trifluoromethoxy)-[1,1'-biphenyl]-4-yl)piperidine-1,2-dicarboxamide (hereinafter referred to as the compound of Example 22) (2.50 g, 5.66 mmol, 75.2%) as a white solid.

$^1$H-NMR (400 MHz, CDCl$_3$) δ: 1.50-1.68(m, 2H), 1.73 (br, 2H), 1.81-1.92(m, 1H), 2.30(d, J=12.9 Hz, 1H), 3.21(dt, J=12.8, 2.6 Hz, 1H), 3.52(d, J=13.2 Hz, 1H), 4.81(br, 2H), 5.03(d, J=4.6 Hz, 1H), 7.20(d, J=8.3 Hz, 1H), 7.29-7.37(m, 3H), 7.42(dt, J=10.8, 3.8 Hz, 2H), 7.81(br, 1H), 8.95(br, 1H).

ESI-MS: m/z=442(M+H)$^+$.

Example 23

Synthesis of (R)-N-(2-chloro-2'-(trifluoromethoxy)-[1,1'-biphenyl]-4-yl)-1-(2,2,2-trifluoroacetyl)piperidine-2-carboxamide

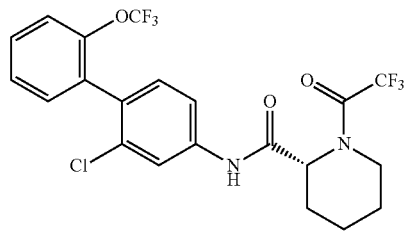

To a dichloromethane (75 mL) solution of the compound of Reference Example 8 (3.00 g, 7.52 mmol), triethylamine (1.57 mL, 11.28 mmol) and trifluoroacetic anhydride (1.17 mL, 8.27 mmol) were added at 0° C. and the temperature was raised to room temperature, followed by stirring for 30 minutes. To the reaction solution, distilled water was added, and the solution was extracted with chloroform. The organic layer was washed with distilled water and saturated brine, dried over anhydrous sodium sulfate and filtered, and then the filtrate was concentrated under reduced pressure. The residue was purified by column chromatography (silica gel, n-hexane/ethyl acetate=20/80) to obtain (R)-N-(2-chloro-2'-(trifluoromethoxy)-[1,1'-biphenyl]-4-yl)-1-(2,2,2-trifluoroacetyl)piperidine-2-carboxamide (hereinafter referred to as the compound of Example 23) (2.50 g, 5.05 mmol, 67.2%) as a white solid. As a result of analysis using a chiral column, the retention time of the thus obtained compound of Example 23 was 33.6 minutes, and the optical purity at that time was 95.0% ee. The analysis conditions using the chiral column are as follows.

Measurement equipment; High-performance liquid chromatograph LC-2010CHT, manufactured by Shimadzu Corporation
Column; CHIRALCEL OD-RH 0.46 cmφ×15 cm, particle size of 5 μm, manufactured by Daicel Chemical Industries Ltd.
Column temperature; 40° C.
Mobile phase; (Solution A) 20 mM aqueous potassium dihydrogen phosphate solution, (Solution B) acetonitrile
Composition of mobile phase; Solution A: Solution B=60:40 to 50:50 (0 to 40 minutes, linear gradient)
Solution A: Solution B=50:50 to 60:40 (40 to 41 minutes, linear gradient)
Solution A: Solution B=60:40 (41 to 50 minutes)
Flow rate; 0.5 mL/minute
Detection; UV (210 nm)

$^1$H-NMR (400 MHz, CDCl$_3$) δ: 1.56-1.86(m, 4H), 1.98 (dt, J=11.2, 4.6 Hz, 1H), 2.36(d, J=14.1 Hz, 1H), 3.37(td, J=13.4, 2.6 Hz, 1H), 4.01(d, J=13.9 Hz, 1H), 5.18(d, J=5.4 Hz, 1H), 7.21(d, J=8.3 Hz, 1H), 7.30-7.46(m, 5H), 7.79(br, 1H), 7.89(br, 1H).

ESI-MS: m/z=495(M+H)$^+$.

Reference Example 9

Synthesis of (1R,5S)-2-((R)-1-phenylethyl)-6-oxa-2-azabicyclo[3.2.1]octan-7-one

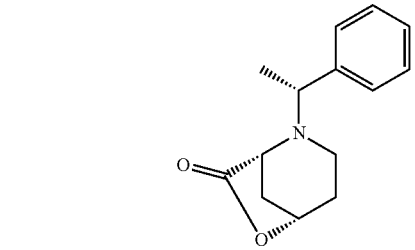 [SMILES: C[C@H](c1ccccc1)N1CC[C@H]2C[C@@H]1C(=O)O2]

To a DMF (30 mL) solution of (R)-α-methylbenzylamine (3.77 mL, 29.6 mmol), potassium carbonate (4.09 g, 29.6 mmol) and 4-bromo-1-butene (3.01 mL, 29.6 mmol) were added at room temperature, followed by stirring at the same temperature for 24 hours. To the reaction solution, distilled water was added, and the solution was extracted with diethyl ether. The organic layer was washed with saturated brine, dried over anhydrous sodium sulfate and filtered, and then the filtrate was concentrated under reduced pressure. To a tetrahydrofuran (12 mL) solution of the residue, glyoxylic acid (4.09 mL, 36.8 mmol) was added at 0° C. and the temperature was raised to 60° C., followed by stirring for 9 hours. To the reaction solution, distilled water and an aqueous 1M sodium hydroxide solution was added, and the solution was extracted with ethyl acetate. The organic layer was washed with an aqueous saturated sodium hydrogen carbonate solution, distilled water, and saturated brine, dried over anhydrous sodium sulfate and filtered, and then the filtrate was concentrated under reduced pressure. The residue was purified by column chromatography (silica gel, n-hexane/ethyl acetate=91/9 to 85/15) to obtain (1R,5S)-2-((R)-1-phenylethyl)-6-oxa-2-azabicyclo[3.2.1]octan-7-one (hereinafter referred to as the compound of Reference Example 9) (1.73 g, 7.48 mmol, 25.3%) as a pale yellow oily product.

$^1$H-NMR (400 MHz, CDCl$_3$) δ: 1.33(d, J=6.6 Hz, 3H), 1.82(d, J=11.7 Hz, 1H), 1.87-1.95(m, 1H), 2.03-2.12(m, 2H), 2.47(td, J=11.8, 5.1 Hz, 1H), 3.19(d, J=5.1 Hz, 1H), 3.35(dd, J=12.0, 6.6 Hz, 1H), 3.70(q, J=6.6 Hz, 1H), 4.78(t, J=5.1 Hz, 1H), 7.23-7.27(m, 1H), 7.31-7.35(m, 2H), 7.39-7.41(m, 2H).

ESI-MS: m/z=232(M+H)$^+$.

Reference Example 10

Synthesis of (1R,5S)-2-(tert-butoxycarbonyl)-6-oxa-2-azabicyclo[3.2.1]-octan-7-one

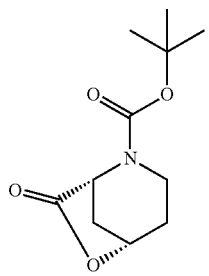 [SMILES: CC(C)(C)OC(=O)N1CC[C@H]2C[C@@H]1C(=O)O2]

To an ethyl acetate (25 mL) solution of the compound of Reference Example 9 (1.73 g, 7.48 mmol), 20% by weight palladium hydroxide-carbon (containing 50% by weight of water, 0.210 g) and di-tert-butyl dicarbonate (1.80 g, 8.23 mmol) were added at room temperature, followed by stirring in a hydrogen atmosphere at the same temperature for 36 hours. The reaction solution was filtered through Celite and then the filtrate was concentrated under reduced pressure. The residue was suspended in diethyl ether/n-hexane=1/9 (v/v) and the obtained solid was collected by filtration and dried to obtain (1R,5S)-2-(tert-butoxycarbonyl)-6-oxa-2-azabicyclo[3.2.1]-octan-7-one (hereinafter referred to as the compound of Reference Example 10) (1.63 g, 7.17 mmol, 95.9%) as a white solid.

$^1$H-NMR (400 MHz, CDCl$_3$) δ: 1.48(s, 9H), 1.84-1.93(m, 1H), 1.95(d, J=12.0 Hz, 1H), 2.03-2.06(m, 1H), 2.29-2.32 (m, 1H), 3.18-3.21(m, 1H), 4.06(m, 1H), 4.70-4.85(m, 1H), 4.97(t, J=5.1 Hz, 1H).

ESI-MS: m/z=228(M+H)$^+$.

Reference Example 11

Synthesis of tert-butyl (2R,4S)-2-((2-chloro-2'-(trifluoromethoxy)-[1,1'-biphenyl]-4-yl)carbamoyl)-4-hydroxypiperidine-1-carboxylate

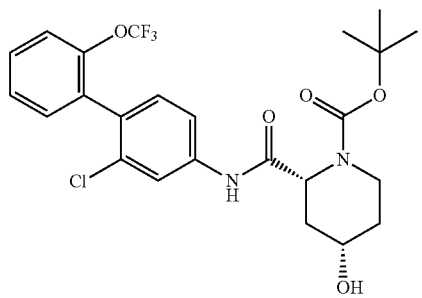 [SMILES: CC(C)(C)OC(=O)N1CC[C@H](O)C[C@@H]1C(=O)Nc1ccc(-c2ccccc2OC(F)(F)F)c(Cl)c1]

To a toluene (2.3 mL) solution of the compound of Reference Example 10 (0.320 g, 1.41 mmol), a trimethyl-aluminum-toluene solution (1.4M, 1.31 mL, 1.83 mmol) was added at 0° C. and the temperature was raised to room temperature, followed by stirring for 30 minutes. A toluene (2.3 mL) solution of the compound of Reference Example 1 (0.486 g, 1.690 mmol) was added and the temperature was raised to 50° C., followed by stirring for 4 hours. To the reaction solution, 1M hydrochloric acid was added, and the solution was extracted with ethyl acetate. The organic layer was washed with distilled water and saturated brine, dried over anhydrous sodium sulfate and filtered, and then the filtrate was concentrated under reduced pressure. The residue was purified by column chromatography (silica gel, n-hexane/ethyl acetate=80/20 to 50/50) to obtain tert-butyl (2R,4S)-2-((2-chloro-2'-(trifluoromethoxy)-[1,1'-biphenyl]-4-yl)carbamoyl)-4-hydroxypiperidine-1-carboxylate (hereinafter referred to as the compound of Reference Example 11) (0.654 g, 1.27 mmol, 90.2%) as a white solid.

$^1$H-NMR (400 MHz, CDCl$_3$) δ: 1.54(s, 9H), 1.66-1.69(m, 1H), 1.78-1.82(m, 1H), 1.93-2.00(m, 1H), 2.40(d, J=13.4 Hz, 1H), 3.25(td, J=13.2, 2.4 Hz, 1H), 3.86-3.88(m, 1H), 4.12-4.14(m, 1H), 4.98-5.00(m, 1H), 5.20(br, 1H), 7.24(d, J=8.3 Hz, 1H), 7.30-7.46(m, 5H), 7.75-7.78(m, 1H), 9.08(br, 1H).

ESI-MS: m/z=515(M+H)$^+$.

Reference Example 12

Synthesis of (2R,4S)—N-(2-chloro-2'-(trifluoromethoxy)-[1,1'-biphenyl]-4-yl)-4-hydroxypiperidine-2-carboxamide hydrochloride

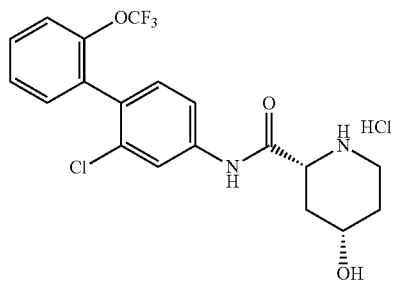 [SMILES: O=C(Nc1ccc(-c2ccccc2OC(F)(F)F)c(Cl)c1)[C@H]1C[C@@H](O)CCN1 ; Cl]

To an ethyl acetate (0.5 mL) solution of the compound of Reference Example 11 (0.0500 g, 0.0973 mmol), a hydrogen chloride-ethyl acetate solution (4.0M, 0.486 mL, 1.94 mmol) was added at 0° C. and the temperature was raised to room temperature, followed by stirring for 3 hours. The reaction solution was filtered and the obtained solid collected by filtration was washed with ethyl acetate and then dried to obtain (2R,4S)—N-(2-chloro-2'-(trifluoromethoxy)-[1,1'-biphenyl]-4-yl)-4-hydroxypiperidine-2-carboxamide hydrochloride (hereinafter referred to as the compound of Reference Example 12) (0.0409 g, 0.0908 mmol, 93.3%) as a white solid.

$^1$H-NMR (DMSO-D$_6$) δ: 1.46-1.62(m, 2H), 1.91-1.94(m, 1H), 2.42-2.45(m, 1H), 3.01(t, J=12.2 Hz, 1H), 3.28-3.32(m, 1H), 3.69-3.78(m, 1H), 4.00(d, J=12.0 Hz, 1H), 5.28(d, J=4.9 Hz, 1H), 7.38(d, J=8.3 Hz, 1H), 7.42(dd, J=7.8, 1.7 Hz, 1H), 7.48-7.52(m, 2H), 7.56-7.64(m, 2H), 7.94(s, 1H), 8.93(br, 1H), 11.00(s, 1H).

ESI-MS: m/z=415(M+H)$^+$.

Reference Example 13

Synthesis of tert-butyl (2R,4R)-2-((2-chloro-2'-(trifluoromethoxy)-[1,1'-biphenyl]-4-yl)carbamoyl)-4-fluoropiperidine-1-carboxylate

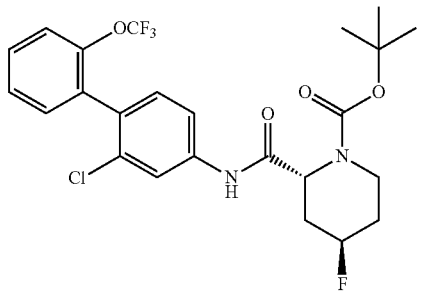 [SMILES: CC(C)(C)OC(=O)N1CC[C@@H](F)C[C@@H]1C(=O)Nc1ccc(-c2ccccc2OC(F)(F)F)c(Cl)c1]

To a dichloromethane (1.9 mL) solution of the compound of Reference Example 11 (0.100 g, 0.194 mmol), (diethylamino)sulfur trifluoride (0.0380 mL, 0.291 mmol) was added at −78° C. and the temperature was raised to room temperature, followed by stirring for 24 hours. To the reaction solution, an aqueous saturated sodium hydrogen carbonate solution was added, and the solution was extracted with chloroform. The organic layer was washed with saturated brine, dried over anhydrous sodium sulfate and filtered, and then the filtrate was concentrated under reduced pressure. The residue was purified by column chromatography (silica gel, n-hexane/ethyl acetate=90/10 to 80/20) to obtain tert-butyl (2R,4R)-2-((2-chloro-2'-(trifluoromethoxy)-[1,1'-biphenyl]-4-yl)carbamoyl)-4-fluoropiperidine-1-carboxylate (hereinafter referred to as the compound of Reference Example 13) (0.0272 g, 0.0527 mmol, 27.2%) as a white solid.

$^1$H-NMR (400 MHz, CDCl$_3$) δ: 1.48-1.56(m, 1H), 1.54(s, 9H), 1.59-1.86(m, 2H), 2.07-2.19(m, 1H), 2.65-2.71(m, 1H), 2.93(t, J=12.8 Hz, 1H), 4.10-4.13(m, 1H), 5.04-5.06(m, 1H), 7.22(d, J=8.3 Hz, 1H), 7.29-7.36(m, 4H), 7.41-7.45(m, 1H), 7.76(br, 1H).

ESI-MS: m/z=517(M+H)$^+$.

Reference Example 14

Synthesis of (2R,4R)-N-(2-chloro-2'-(trifluoromethoxy)-[1,1'-biphenyl]-4-yl)-4-fluoropiperidine-2-carboxamide hydrochloride

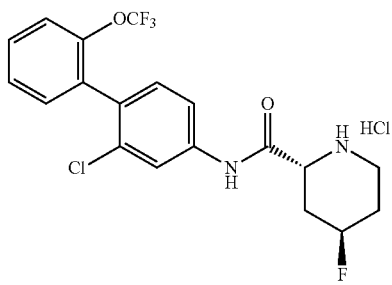 [SMILES: O=C(Nc1ccc(-c2ccccc2OC(F)(F)F)c(Cl)c1)[C@H]1C[C@H](F)CCN1 ; Cl]

According to the same procedure as in Example 12, except that the compound of Reference Example 13 was used in place of the compound of Reference Example 11, (2R,4R)—N-(2-chloro-2'-(trifluoromethoxy)-[1,1'-biphenyl]-4-yl)-4-fluoropiperidine-2-carboxamide hydrochloride (hereinafter referred to as the compound of Reference Example 14) (0.0186 g, 0.0410 mmol, 84.9%) was obtained as a white solid.

$^1$H-NMR (DMSO-D$_6$) δ: 1.89-2.06(m, 2H), 2.24-2.33(m, 1H), 3.12-3.27(m, 2H), 4.18(d, J=12.4 Hz, 1H), 5.16(d, J=47.1 Hz, 1H), 7.38(d, J=8.5 Hz, 1H), 7.42(dd, J=7.9, 1.8 Hz, 1H), 7.48-7.52(m, 2H), 7.56-7.61(m, 2H), 7.95(br, 1H), 9.12(br, 1H), 10.97(s, 1H).

ESI-MS: m/z=417(M+H)$^+$.

Reference Example 15

Synthesis of tert-butyl (2R,4R)-2-((2-chloro-2'-(trifluoromethoxy)-[1,1'-biphenyl]-4-yl)carbamoyl)-4-(formyloxy)piperidine-1-carboxylate

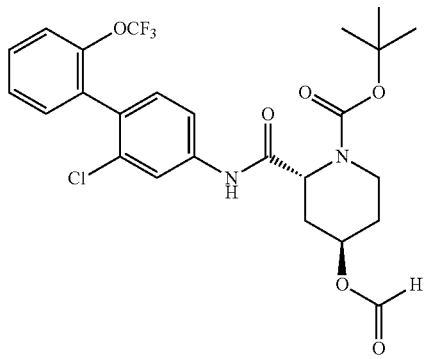 [SMILES: CC(C)(C)OC(=O)N1CC[C@@H](OC=O)C[C@@H]1C(=O)Nc1ccc(-c2ccccc2OC(F)(F)F)c(Cl)c1]

To a tetrahydrofuran (1.0 mL) solution of triphenylphosphine (0.153 g, 0.583 mmol), diisopropyl azodicarboxylate (0.113 mL, 0.583 mmol) was added at 0° C. and, after stirring at the same temperature for 1 hour, formic acid (0.0220 mL, 0.583 mmol) was added and the mixture was stirred at the same temperature for 30 minutes. A tetrahydrofuran (1.00 mL) solution of the compound of Reference Example 11 (0.200 g, 0.388 mmol) was added dropwise and the temperature was raised to room temperature, followed by stirring for 12 hours. The reaction solution was concentrated under reduced pressure and the residue was purified by column chromatography (silica gel, n-hexane/ethyl acetate=85/15 to 70/30) to obtain tert-butyl (2R,4R)-2-((2-chloro-2'-(trifluoromethoxy)-[1,1'-biphenyl]-4-yl)carbamoyl)-4-(formyloxy)piperidine-1-carboxylate (hereinafter referred to as the compound of Reference Example 15) (0.0939 g, 0.173 mmol, 44.5%) as a white solid.

$^1$H-NMR (400 MHz, CDCl$_3$) δ: 1.28-1.37(m, 2H), 1.54(s, 9H), 1.67-1.74(m, 1H), 2.07-2.12(m, 1H), 2.61-2.63(m, 1H), 2.96-3.02(m, 1H), 4.12-4.14(m, 1H), 5.06(br, 1H), 5.43(br, 1H), 7.22(d, J=8.3 Hz, 1H), 7.32-7.37(m, 3H), 7.41-7.45(m, 2H), 7.80(br, 1H), 8.06(s, 1H).

ESI-MS: m/z=543(M+H)$^+$.

Reference Example 16

Synthesis of tert-butyl (2R,4R)-2-((2-chloro-2'-(trifluoromethoxy)-[1,1'-biphenyl]-4-yl)carbamoyl)-4-hydroxypiperidine-1-carboxylate

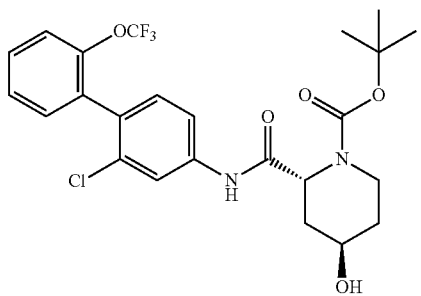

To a methanol (1.1 mL) solution of the compound of Reference Example 15 (0.0900 g, 0.166 mmol), a sodium methoxide-methanol solution (4.0M, 0.0207 mL, 0.0828 mmol) was added at 0° C., followed by stirring at the same temperature for 15 minutes. To the reaction solution, 1M hydrochloric acid was added, and the solution was extracted with ethyl acetate. The organic layer was washed with saturated brine, dried over anhydrous sodium sulfate and filtered, and then the filtrate was concentrated under reduced pressure. The residue was purified by column chromatography (silica gel, n-hexane/ethyl acetate=80/20 to 50/50) to obtain tert-butyl (2R,4R)-2-((2-chloro-2'-(trifluoromethoxy)-[1,1'-biphenyl]-4-yl)carbamoyl)-4-hydroxypiperidine-1-carboxylate (hereinafter referred to as the compound of Reference Example 16) (0.0844 g, 0.164 mmol, 99.3%) as a white solid.

$^1$H-NMR (400 MHz, CDCl$_3$) δ: 1.46-1.54(m, 2H), 1.54(s, 9H), 1.68-1.71(m, 1H), 1.94-1.97(m, 1H), 2.54-2.56(m, 1H), 2.86-2.93(m, 1H), 4.13-4.22(m, 2H), 5.04(br, 1H), 7.22(d, J=8.3 Hz, 1H), 7.30-7.45(m, 5H), 7.78(br, 1H), 8.52(s, 1H).

ESI-MS: m/z=515(M+H)$^+$.

Reference Example 17

Synthesis of tert-butyl (R)-2-((2-chloro-2'-(trifluoromethoxy)-[1,1'-biphenyl]-4-yl)carbamoyl)-4-oxopiperidine-1-carboxylate

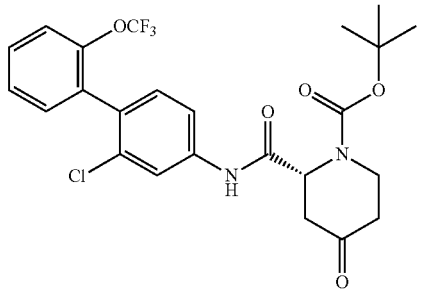 [SMILES: CC(C)(C)OC(=O)N1CCC(=O)C[C@@H]1C(=O)Nc1ccc(-c2ccccc2OC(F)(F)F)c(Cl)c1]

To a dichloromethane (2.0 mL) solution of the compound of Reference Example 11 (0.210 g, 0.408 mmol), Dess-Martin periodinane (0.190 g, 0.449 mmol) was added at 0° C. and the temperature was raised to room temperature, followed by stirring for 3 hours. To the reaction solution, an aqueous sodium thiosulfate solution was added, and the solution was extracted with ethyl acetate. The organic layer was washed with distilled water and saturated brine, dried over anhydrous sodium sulfate and filtered, and then the filtrate was concentrated under reduced pressure. The residue was purified by column chromatography (silica gel, n-hexane/ethyl acetate =90/10 to 60/40) to obtain tert-butyl (R)-2-((2-chloro-2'-(trifluoromethoxy)-[1,1'-biphenyl]-4-yl)carbamoyl)-4-oxopiperidine-1-carboxylate (hereinafter referred to as the compound of Reference Example 17) (0.190 g, 0.370 mmol, 90.9%) as a white solid.

$^1$H-NMR (400 MHz, CDCl$_3$) δ: 1.56(s, 9H), 2.46-2.53(m, 1H), 2.61-2.73(m, 2H), 3.00(dd, J=16.5, 3.3 Hz, 1H), 3.66-3.73(m, 1H), 3.82(br, 1H), 5.05(s, 1H), 7.22(d, J=8.3 Hz, 1H), 7.29-7.36(m, 3H), 7.41-7.45(m, 2H), 7.78(br, 1H), 9.14(br, 1H).

ESI-MS: m/z=513(M+H)$^+$.

Reference Example 18

Synthesis of tert-butyl (R)-2-((2-chloro-2'-(trifluoromethoxy)-[1,1'-biphenyl]-4-yl)carbamoyl)-4,4-difluoropiperidine-1-carboxylate

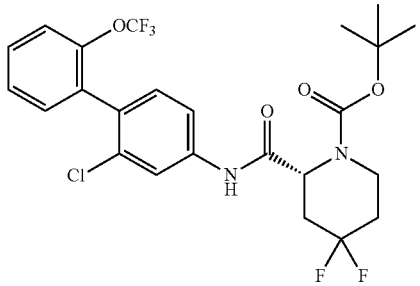 [SMILES: CC(C)(C)OC(=O)N1CCC(F)(F)C[C@@H]1C(=O)Nc1ccc(-c2ccccc2OC(F)(F)F)c(Cl)c1]

To a dichloromethane (1.9 mL) solution of the compound of Reference Example 17 (0.190 g, 0.370 mmol), (diethylamino)sulfur trifluoride (0.108 mL, 0.815 mmol) was added at 0° C. and the temperature was raised to room temperature, followed by stirring for 24 hours. To the reaction solution, an aqueous saturated sodium hydrogen carbonate solution was added, and the solution was extracted with chloroform. The organic layer was washed with saturated brine, dried over anhydrous sodium sulfate and filtered, and then the filtrate was concentrated under reduced pressure. The residue was purified by column chromatography (silica gel, n-hexane/ethyl acetate=85/15 to 70/30) to obtain tert-butyl (R)-2-((2-chloro-2'-(trifluoromethoxy)-[1,1'-biphenyl]-4-yl)carbamoyl)-4,4-difluoropiperidine-1-carboxylate (hereinafter referred to as the compound of Reference Example 18) (0.0393 g, 0.0735 mmol, 19.8%) as a white solid.

$^1$H-NMR (400 MHz, CDCl$_3$) δ: 1.54(s, 9H), 1.86-2.15(m, 3H), 2.99-3.07(m, 1H), 3.21(td, J=13.3, 2.7 Hz, 1H), 4.22-4.25(m, 1H), 5.07(br, 1H), 7.24(d, J=8.5 Hz, 1H), 7.30-7.37(m, 3H), 7.41-7.46(m, 2H), 7.76(s, 1H), 7.97(br, 1H).

ESI-MS: m/z=535(M+H)$^+$.

Example 24

Synthesis of (2R,4S)-1-acetyl-N-(2-chloro-2'-(trifluoromethoxy)-[1,1'-biphenyl]-4-yl)-4-hydroxypiperidine-2-carboxamide

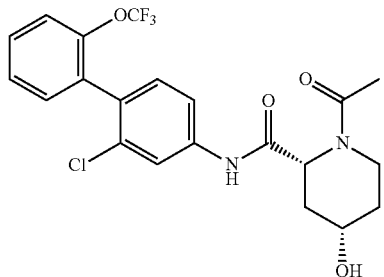 [SMILES: CC(=O)N1CC[C@H](O)C[C@@H]1C(=O)Nc1ccc(-c2ccccc2OC(F)(F)F)c(Cl)c1]

According to the same procedure as in Example 3, except that the compound of Reference Example 12 was used in place of the compound of Reference Example 3 and acetyl chloride was used in place of propionyl chloride, (2R,4S)-1-acetyl-N-(2-chloro-2'-(trifluoromethoxy)-[1,1'-biphenyl]-4-yl)-4-hydroxypiperidine-2-carboxamide (hereinafter referred to as the compound of Example 24) (0.0166 g, 0.0363 mmol, 91.1%) was obtained as a white solid.

$^1$H-NMR (400 MHz, CDCl$_3$) δ: 1.68-1.76(m, 1H), 1.87-1.98(m, 2H), 2.24(s, 3H), 2.39(d, J=14.6 Hz, 1H), 3.50-3.57(m, 1H), 3.61-3.66(m, 1H), 4.14-4.17(m, 1H), 5.42(d, J=6.8 Hz, 1H), 5.52(d, J=6.8 Hz, 1H), 7.23(d, J=8.5 Hz, 1H), 7.31-7.37(m, 3H), 7.41-7.46(m, 2H), 7.77(br, 1H), 9.15(s, 1H).

ESI-MS: m/z=457(M+H)$^+$.

Example 25

Synthesis of (2R,4R)-1-acetyl-N-(2-chloro-2'-(trifluoromethoxy)-[1,1'-biphenyl]-4-yl)-4-fluoropiperidine-2-carboxamide

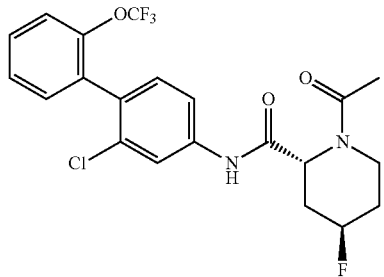 [SMILES: CC(=O)N1CC[C@@H](F)C[C@@H]1C(=O)Nc1ccc(-c2ccccc2OC(F)(F)F)c(Cl)c1]

According to the same procedure as in Example 3, except that the compound of Reference Example 14 was used in place of the compound of Reference Example 3 and acetyl chloride was used in place of propionyl chloride, (2R,4R)-1-acetyl-N-(2-chloro-2'-(trifluoromethoxy)-[1,1'-biphenyl]-4-yl)-4-fluoropiperidine-2-carboxamide (hereinafter referred to as the compound of Example 25) (0.0108 g, 0.0235 mmol, 62.8%) was obtained as a white solid.

$^1$H-NMR (400 MHz, CDCl$_3$) δ: 1.69-1.85(m, 2H), 2.22-2.25(m, 1H), 2.25(s, 3H), 2.62-2.69(m, 1H), 3.21-3.28(m, 1H), 3.85(dd, J=13.4, 2.9 Hz, 1H), 5.24-5.43(m, 1H), 5.43(d, J=5.4 Hz, 1H), 7.21(d, J=8.3 Hz, 1H), 7.30-7.36(m, 3H), 7.41-7.45(m, 2H), 7.70-7.82(m, 1H), 8.72(s, 1H).

ESI-MS: m/z=459(M+H)$^+$.

Example 26

Synthesis of (2R,4S)—N-(2-chloro-2'-(trifluoromethoxy)-[1,1'-biphenyl]-4-yl)-4-hydroxy-1-(methylsulfonyl)piperidine-2-carboxamide

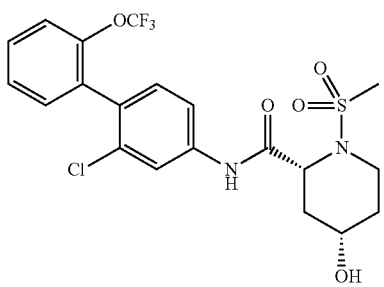 [SMILES: CS(=O)(=O)N1CC[C@H](O)C[C@@H]1C(=O)Nc1ccc(-c2ccccc2OC(F)(F)F)c(Cl)c1]

According to the same procedure as in Example 3, except that the compound of Reference Example 12 was used in place of the compound of Reference Example 3 and methanesulfonyl chloride was used in place of propionyl chloride, (2R,4S)—N-(2-chloro-2'-(trifluoromethoxy)-[1,1'-biphenyl]-4-yl)-4-hydroxy-1-(methylsulfonyl)piperidine-2-carboxamide (hereinafter referred to as the compound of Example 26) (0.00841 g, 0.0171 mmol, 42.7%) was obtained as a white solid.

$^1$H-NMR (400 MHz, CDCl$_3$) δ: 1.68-1.76(m, 1H), 1.85-1.88(m, 1H), 1.99(ddd, J=14.9, 6.9, 3.1 Hz, 1H), 2.61(d, J=14.9 Hz, 1H), 3.03(s, 3H), 3.55-3.62(m, 1H), 3.72(d, J=4.6 Hz, 1H), 3.75-3.79(m, 1H), 4.22-4.24(m, 1H), 4.66(d, J=6.6 Hz, 1H), 7.25-7.27(m, 1H), 7.31-7.37(m, 3H), 7.42-7.46(m, 2H), 7.81(d, J=2.0 Hz, 1H), 8.58(s, 1H).

ESI-MS: m/z=493(M+H)$^+$.

Example 27

Synthesis of (2R,4R)-1-acetyl-N-(2-chloro-2'-(trifluoromethoxy)-[1,1'-biphenyl]-4-yl)-4-hydroxypiperidine-2-carboxamide

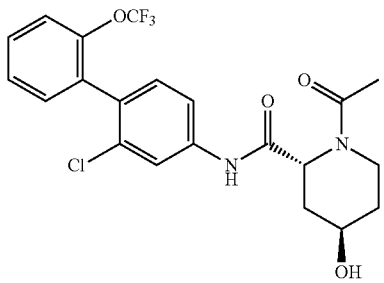

To an ethyl acetate (0.4 mL) solution of the compound of Reference Example 16 (0.0200 g, 0.0388 mmol), a hydrogen chloride-ethyl acetate solution (4.0M, 0.194 mL, 1.94 mmol) was added at 0° C. and the temperature was raised to room temperature, followed by stirring for 3 hours. The reaction solution was concentrated under reduced pressure and the residue was dissolved in dichloromethane (0.8 mL) and then triethylamine (0.00135 mL, 0.0970 mmol) and acetyl chloride (0.00359 mL, 0.0504 mmol) were added at 0° C., followed by stirring at the same temperature for 1 hour. To the reaction solution, methanol was added, and the solution was concentrated under reduced pressure. The residue was purified by column chromatography (silica gel, ethyl acetate/methanol=100/0 to 97/3) to obtain (2R,4R)-1-acetyl-N-(2-chloro-2'-(trifluoromethoxy)-[1,1'-biphenyl]-4-yl)-4-hydroxypiperidine-2-carboxamide (hereinafter referred to as the compound of Example 27) (0.0106 g, 0.0232 mmol, 59.7%) as a white solid.

$^1$H-NMR (400 MHz, CDCl$_3$) δ: 1.47-1.57(m, 2H), 1.81(d, J=3.6 Hz, 1H), 2.04-2.09(m, 1H), 2.25(s, 3H), 2.50(ddt, J=13.1, 5.0, 1.8 Hz, 1H), 3.22(td, J=13.4, 2.6 Hz, 1H), 3.85(d, J=13.4 Hz, 1H), 4.40-4.48(m, 1H), 5.43(d, J=5.9 Hz, 1H), 7.21(d, J=8.2 Hz, 1H), 7.30-7.37(m, 3H), 7.41-7.45(m, 2H), 7.69-7.83(m, 1H), 8.65(s, 1H).

ESI-MS: m/z=457(M+H)$^+$.

Example 28

Synthesis of (R)-N-(2-chloro-2'-(trifluoromethoxy)-[1,1'-biphenyl]-4-yl)-4,4-difluoro-1-(methylsulfonyl)piperidine-2-carboxamide

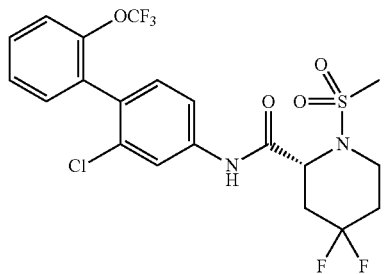 [SMILES: CS(=O)(=O)N1CCC(F)(F)C[C@@H]1C(=O)Nc1ccc(-c2ccccc2OC(F)(F)F)c(Cl)c1]

According to the same procedure as in Example 27, except that the compound of Reference Example 18 was used in place of the compound of Reference Example 16 and methanesulfonyl chloride was used in place of acetyl chloride, (R)-N-(2-chloro-2'-(trifluoromethoxy)-[1,1'-biphenyl]-4-yl)-4,4-difluoro-1-(methylsulfonyl)piperidine-2-carboxamide (hereinafter referred to as the compound of Example 28) (0.0127 g, 0.0248 mmol, 77.0%) was obtained as a white solid.

$^1$H-NMR (400 MHz, CDCl$_3$) δ: 1.95-2.12(m, 1H), 2.15-2.32(m, 2H), 2.95-3.02(m, 1H), 3.10(s, 3H), 3.60(td, J=13.5, 3.0 Hz, 1H), 4.02-4.08(m, 1H), 4.89(d, J=7.2 Hz, 1H), 7.26(d, J=8.2 Hz, 1H), 7.30-7.37(m, 3H), 7.42-7.46(m, 2H), 7.76(s, 1H), 7.93(s, 1H).

ESI-MS: m/z=513(M+H)$^+$.

Reference Example 19

Synthesis of tert-butyl 2-(N-methylmethylsulfonamide)acetate

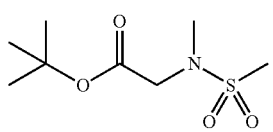

To a dichloromethane (2.0 mL) solution of tert-butyl 2-(methylamino)acetate hydrochloride (0.100 g, 0.550 mmol), triethylamine (0.192 mL, 1.385 mmol) and methanesulfonyl chloride (0.0515 mL, 0.661 mmol) were added at 0° C. and the temperature was raised to room temperature, followed by stirring for 3 hours. To the reaction solution, an aqueous saturated ammonium chloride solution was added, and the solution was extracted with chloroform. The organic layer was dried over anhydrous sodium sulfate and filtered, and then the filtrate was concentrated under reduced pressure. The residue was purified by column chromatography (silica gel, n-hexane/ethyl acetate=90/10 to 70/30) to obtain tert-butyl 2-(N-methylmethylsulfonamide)acetate (hereinafter referred to as the compound of Reference Example 19) (0.117 g, 0.524 mmol, 95.2%) as a colorless oily product.

$^1$H-NMR (400 MHz, CDCl$_3$) δ: 1.48(s, 9H), 2.98(s, 3H), 3.00(s, 3H), 3.98(s, 2H).

Reference Example 20

Synthesis of 2-(N-Methylmethylsulfonamide)Acetic Acid

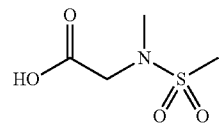

To an acetonitrile (1.5 mL) solution of the compound of Reference Example 19 (0.117 g, 0.524 mmol), a hydrogen chloride-ethyl acetate solution (4.0M, 1.31 mL, 5.24 mmol) was added at 0° C. and the temperature was raised to room temperature, followed by stirring for 16 hours. The reaction solution was concentrated under reduced pressure to obtain crude 2-(N-methylmethylsulfonamide)acetic acid (hereinafter referred to as the compound of Reference Example 20) (0.0855 g) as a colorless oily product. The compound of Reference Example 20 was directly used for the subsequent reaction.

$^1$H-NMR (400 MHz, CDCl$_3$) δ: 2.99(s, 3H), 3.01(s, 3H), 4.14(s, 2H).

ESI-MS: m/z=168(M+H)$^+$.

Example 29

Synthesis of (R)-N-(2-chloro-2'-(trifluoromethoxy)-[1,1'-biphenyl]-4-yl)-1-(2-(N-methylmethylsulfonamide)acetyl)piperidine-2-carboxamide

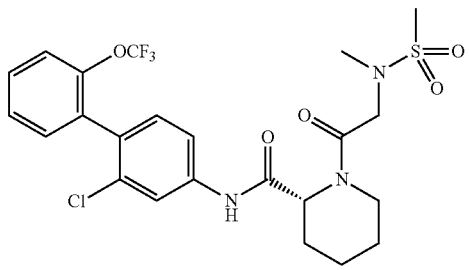 [SMILES: CN(CC(=O)N1CCCC[C@@H]1C(=O)Nc1ccc(-c2ccccc2OC(F)(F)F)c(Cl)c1)S(C)(=O)=O]

To a DMF (2.0 mL) solution of the compound of Reference Example 20 (0.0850 g, 0.508 mmol), a DMF (1.0 mL)

solution of the compound of Reference Example 8 (0.184 g, 0.462 mmol), HATU (0.193 g, 0.508 mmol), and diisopropylethylamine (0.121 mL, 0.693 mmol) were added at room temperature, followed by stirring at the same temperature for 18 hours. To the reaction solution, distilled water was added, and the solution was extracted with a mixed solvent of n-hexane/ethyl acetate=20/80 (v/v). The organic layer was washed with saturated brine, dried over anhydrous sodium sulfate and filtered, and then the filtrate was concentrated under reduced pressure. The residue was purified by column chromatography (silica gel, n-hexane/ethyl acetate=50/50 to 30/70) to obtain (R)-N-(2-chloro-2'-(trifluoromethoxy)-[1,1'-biphenyl]-4-yl)-1-(2-(N-methylmethylsulfonamide) acetyl)piperidine-2-carboxamide (hereinafter referred to as the compound of Example 29) (0.209 g, 0.380 mmol, 82.0%) as a white solid. As a result of analysis using a chiral column, the retention time of the thus obtained compound of Example 29 was 34.5 minutes, and the optical purity at that time was 98.2% ee. The analysis conditions using the chiral column are as follows.

Measurement equipment; High-performance liquid chromatograph LC-2010CHT, manufactured by Shimadzu Corporation
Column; CHIRALCEL OD-RH 0.46 cmφ×15 cm, particle size of 5 μm, manufactured by Daicel Chemical Industries Ltd.
Column temperature; 40° C.
Mobile phase; (Solution A) 20 mM aqueous potassium dihydrogen phosphate solution, (Solution B) acetonitrile
Composition of mobile phase; Solution A: Solution B=60:40 to 50:50 (0 to 40 minutes, linear gradient)
Solution A: Solution B=50:50 to 60:40 (40 to 41 minutes, linear gradient)
Solution A: Solution B=60:40 (41 to 50 minutes)
Flow rate; 0.5 mL/minute
Detection; UV (210 nm)

$^1$H-NMR (400 MHz, CDCl$_3$) δ: 1.52-1.89(m, 5H), 2.35-2.38(m, 1H), 3.03-3.07(m, 6H), 3.20-3.31(m, 1H), 3.67-3.76 (m, 1H), 4.16-4.27(m, 2H), 5.25-5.26(m, 1H), 7.21-7.23(m, 1H), 7.30-7.45(m, 5H), 7.83(s, 1H), 8.22(br, 1H).
ESI-MS: m/z=548(M+H)$^+$.

Reference Example 21

Synthesis of tert-butyl (3-(2-((2-chloro-2'-(trifluoromethoxy)-[1,1'-biphenyl]-4-yl)carbamoyl)piperidin-1-yl)-3-oxopropyl)carbamate

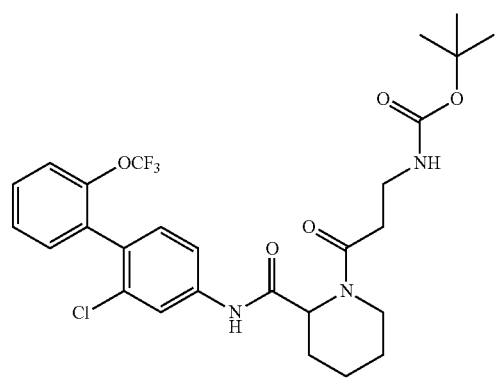

According to the same procedure as in Example 4, except that 3-((tert-butoxycarbonyl)amino)propanoic acid was used in place of 2-methoxyacetic acid, tert-butyl (3-(2-((2-chloro-2'-(trifluoromethoxy)-[1,1'-biphenyl]-4-yl)carbamoyl)piperidin-1-yl)-3-oxopropyl)carbamate (hereinafter referred to as the compound of Reference Example 21) (0.288 g, 0.505 mmol, quantitative) was obtained as a white solid.

$^1$H-NMR (400 MHz, CDCl$_3$) δ: 1.39(s, 9H), 1.50-1.90 (5H, m), 2.35(d, J=13.7 Hz, 1H), 2.55-2.75(m, 2H), 3.20(t, J=12.8 Hz, 1H), 3.41-3.49(m, 1H), 3.50-3.60(m, 1H), 3.80 (d, J=13.7 Hz, 1H) 5.17(br, 1H), 5.33(d, J=4.9 Hz, 1H), 7.20(d, J=8.3 Hz, 1H), 7.29-7.60(m, 5H), 7.70-7.89(m, 1H), 8.65(br, 1H).
ESI-MS: m/z=570(M+H)$^+$.

Example 30

Synthesis of 1-(3-aminopropanoyl)-N-(2-chloro-2'-(trifluoromethoxy)-[1,1'-biphenyl]-4-yl)piperidine-2-carboxamide

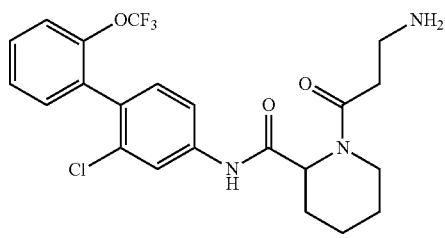 [SMILES: NCCC(=O)N1CCCCC1C(=O)Nc1ccc(-c2ccccc2OC(F)(F)F)c(Cl)c1]

According to the same procedure as in Reference Example 5, except that the compound of Reference Example 21 was used in place of the compound of Reference Example 4, 1-(3-aminopropanoyl)-N-(2-chloro-2'-(trifluoromethoxy)-[1,1'-biphenyl]-4-yl)piperidine-2-carboxamide (hereinafter referred to as the compound of Example 30) (0.155 g, 0.329 mmol, 65.6%) was obtained as a white solid.

$^1$H-NMR (400 MHz, CDCl$_3$) δ: 1.46-1.82(m, 5H), 2.43(d, J=13.1 Hz, 1H) 2.56(dt, J=15.3, 6.2 Hz, 1H), 2.71-2.79(m, 1H), 3.09-3.21(m, 3H), 3.88(d, J=13.1 Hz, 1H), 5.43(d, J=5.0 Hz, 1H), 7.19(d, J=8.2 Hz, 1H), 7.29-7.36(m, 3H), 7.40-7.85(m, 3H), 8.96(br, 1H).
ESI-MS: m/z=470(M+H)$^+$.

Example 31

Synthesis of 1-(3-acetamidepropanoyl)-N-(2-chloro-2'-(trifluoromethoxy)-[1,1'-biphenyl]-4-yl)piperidine-2-carboxamide

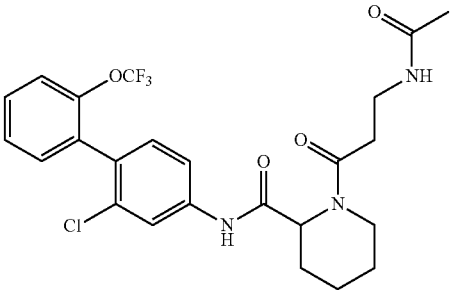 [SMILES: CC(=O)NCCC(=O)N1CCCCC1C(=O)Nc1ccc(-c2ccccc2OC(F)(F)F)c(Cl)c1]

According to the same procedure as in Example 3, except that the compound of Example 30 was used in place of the compound of Reference Example 3 and acetyl chloride was used in place of propionyl chloride, 1-(3-acetamidepropanoyl)-N-(2-chloro-2'-(trifluoromethoxy)-[1,1'-biphenyl]-4-yl)piperidine-2-carboxamide (hereinafter referred to as the compound of Example 31) (0.0218 g, 0.0420 mmol, 99.1%) was obtained as a white solid.

$^1$H-NMR (400 MHz, CDCl$_3$) δ: 1.46-1.94(m, 5H), 1.98(s, 3H), 2.34(d, J=13.3 Hz, 1H), 2.60-2.73(m, 2H), 3.20(td, J=13.3, 2.4 Hz, 1H), 3.52-3.70(m, 2H), 3.79(d, J=13.3 Hz, 1H), 5.30(d, J=4.5 Hz, 1H), 6.23(br, 1H), 7.21(d, J=8.2 Hz, 1H), 7.30-7.90(m, 6H), 8.51(br, 1H).

ESI-MS: m/z=512(M+H)$^+$.

Example 32

Synthesis of N-(2-chloro-2'-(trifluoromethoxy)-[1,1'-biphenyl]-4-yl)-1-(3-(methyl sulfonamide)propanoyl)piperidine-2-carboxamide

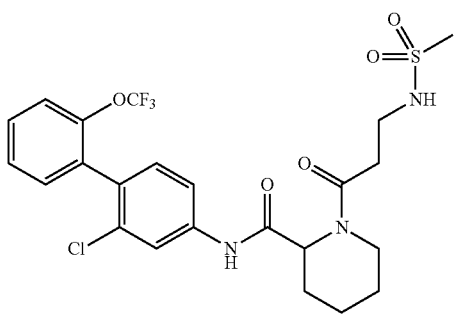 [SMILES: CS(=O)(=O)NCCC(=O)N1CCCCC1C(=O)Nc1ccc(-c2ccccc2OC(F)(F)F)c(Cl)c1]

According to the same procedure as in Example 3, except that the compound of Example 30 was used in place of the compound of Reference Example 3 and methanesulfonyl chloride was used in place of propionyl chloride, N-(2-chloro-2'-(trifluoromethoxy)-[1,1'-biphenyl]-4-yl)-1-(3-(methyl sulfonamide)propanoyl)piperidine-2-carboxamide (hereinafter referred to as the compound of Example 32) (0.0224 g, 0.0409 mmol, 96.1%) was obtained as a white solid.

$^1$H-NMR (400 MHz, CDCl$_3$) δ: 1.50-1.90(m, 5H), 2.33(d, J=13.5 Hz, 1H), 2.75-2.80(m, 2H) 3.00(s, 3H), 3.22(t, J=13.5 Hz, 1H), 3.45-3.51(m, 2H), 3.77(d, J=13.5 Hz, 1H), 5.26-5.30(m, 2H), 7.22(d, J=8.3 Hz, 1H), 7.30-7.44(m, 5H), 7.80(br, 1H), 8.22(br, 1H).

ESI-MS: m/z=548(M+H)$^+$.

Example 33

Synthesis of N-(2-chloro-2'-(trifluoromethoxy)-[1,1'-biphenyl]-4-yl)-1-(3-(dimethylamino)propanoyl)piperidine-2-carboxamide

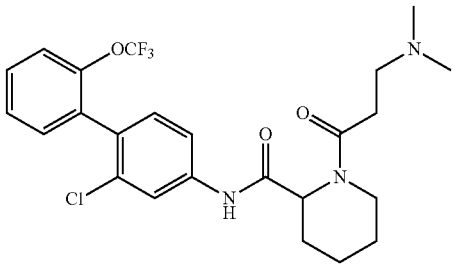

According to the same procedure as in Example 4, except that 3-(dimethylamino)propanoic acid hydrochloride was used as 2-methoxyacetic acid, N-(2-chloro-2'-(trifluoromethoxy)-[1,1'-biphenyl]-4-yl)-1-(3-(dimethylamino)propanoyl)piperidine-2-carboxamide (hereinafter referred to as the compound of Example 33) (0.0274 g, 0.0550 mmol, 73.2%) was obtained as a white solid.

$^1$H-NMR (400 MHz, CDCl$_3$) δ: 1.49-1.83(m, 5H), 2.27(s, 6H), 2.38-2.45(m, 1H), 2.56-2.61(m, 1H), 2.66-2.80(m, 3H), 3.12-3.20(m, 1H), 3.85-3.93(m, 1H), 5.42(d, J=5.4 Hz, 1H), 7.21(d, J=8.3 Hz, 1H), 7.27-7.45(m, 6H), 8.73(br, 1H).

ESI-MS: m/z=498(M+H)$^+$.

Reference Example 22

Synthesis of tert-butyl (3-(2-((2-chloro-2'-(trifluoromethoxy)-[1,1'-biphenyl]-4-yl)carbamoyl)piperidin-1-yl)-3-oxopropyl)(methyl)carbamate

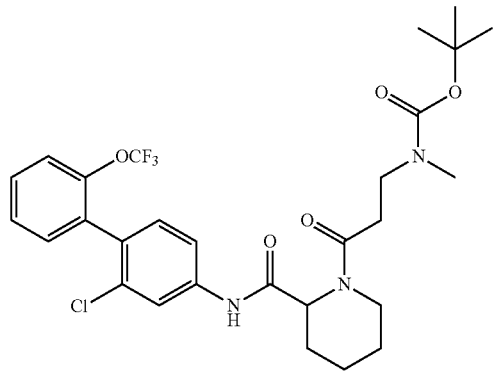

According to the same procedure as in Example 4, except that 3-((tert-butoxycarbonyl)(methyl)amino)propanoic acid was used in place of 2-methoxyacetic acid, tert-butyl (3-(2-((2-chloro-2'-(trifluoromethoxy)-[1,1'-biphenyl]-4-yl)carbamoyl)piperidin-1-yl)-3-oxopropyl)(methyl)carbamate (hereinafter referred to as the compound of Reference Example 22) (0.130 g, 0.223 mmol, 89.0%) was obtained as a white solid.

$^1$H-NMR (400 MHz, CDCl$_3$) δ: 1.35(s, 9H), 1.30-1.77(m, 5H), 2.37-2.80(m, 3H), 2.93(s, 3H), 3.18-3.30(m, 2H) 3.84 (d, J=13.7 Hz, 1H), 3.95-4.03(m, 1H), 5.38-5.42(m, 1H), 7.20(d, J=8.3 Hz, 1H), 7.31-7.46(m, 4H), 7.66-7.72(m, 1H), 7.90-7.92(m, 1H), 9.10(br, 1H).

ESI-MS: m/z=584(M+H)⁺.

Example 34

Synthesis of N-(2-chloro-2'-(trifluoromethoxy)-[1,1'-biphenyl]-4-yl)-1-(3-(methylamino)propanoyl)piperidine-2-carboxamide

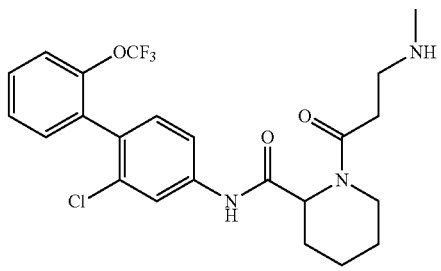

According to the same procedure as in Reference Example 5, except that the compound of Reference Example 22 was used in place of the compound of Reference Example 4, N-(2-chloro-2'-(trifluoromethoxy)-[1,1'-biphenyl]-4-yl)-1-(3-(methylamino)propanoyl)piperidine-2-carboxamide (hereinafter referred to as the compound of Example 34) (0.804 g, 0.166 mmol, 74.6%) was obtained as a white solid.

¹H-NMR (400 MHz, CDCl₃) δ: 1.46-1.83(m, 5H), 2.47(s, 3H), 2.40-2.48(m, 1H), 2.75-2.83(m, 1H), 2.94-2.99(m, 2H), 3.16(td, J=13.1, 2.6 Hz, 1H), 3.88(d, J=13.1 Hz, 1H), 5.41(d, J=5.4 Hz, 1H), 7.21(d, J=8.3 Hz, 1H), 7.30-7.81(m, 6H), 8.80(br, 1H).

ESI-MS: m/z=484(M+H)⁺.

Example 35

Synthesis of N-(2-chloro-2'-(trifluoromethoxy)-[1,1'-biphenyl]-4-yl)-1-(3-(N-methylacetamide)propanoyl)piperidine-2-carboxamide

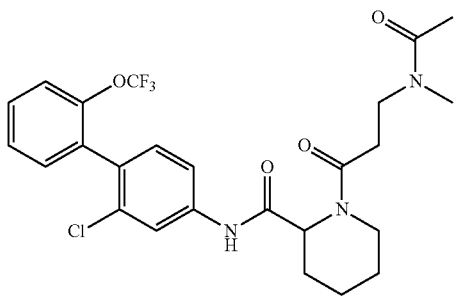 [SMILES: CC(=O)N(C)CCC(=O)N1CCCCC1C(=O)Nc1ccc(-c2ccccc2OC(F)(F)F)c(Cl)c1]

According to the same procedure as in Example 3, except that the compound of Example 34 was used in place of the compound of Reference Example 3 and acetyl chloride was used in place of propionyl chloride, N-(2-chloro-2'-(trifluoromethoxy)-[1,1'-biphenyl]-4-yl)-1-(3-(N-methylacetamide)propanoyl)piperidine-2-carboxamide (hereinafter referred to as the compound of Example 35) (0.0316 g, 0.0601 mmol, 74.5%) was obtained as a white solid.

¹H-NMR (400 MHz, CDCl₃) δ: 1.48-1.77(m, 5H), 2.09(s, 3H), 2.45(d, J=13.7 Hz, 1H), 2.59-2.79(m, 2H), 3.11(s, 3H), 3.20-3.29(m, 2H), 3.84(d, J=13.7 Hz, 1H), 4.21-4.28(m, 1H), 5.35(d, J=5.1 Hz, 1H), 7.20(d, J=8.3 Hz, 1H), 7.31-7.36(m, 3H), 7.38-7.44(m, 1H), 7.70-7.80(m, 1H), 7.97-8.06(m, 1H), 9.09(br, 1H).

ESI-MS: m/z=526(M+H)⁺.

Example 36

Synthesis of N-(2-chloro-2'-(trifluoromethoxy)-[1,1'-biphenyl]-4-yl)-1-(3-(N-methylmethylsulfonamide)propanoyl)piperidine-2-carboxamide

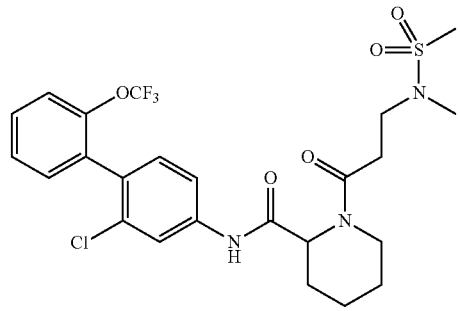 [SMILES: CN(CCC(=O)N1CCCCC1C(=O)Nc1ccc(-c2ccccc2OC(F)(F)F)c(Cl)c1)S(C)(=O)=O]

According to the same procedure as in Example 3, except that the compound of Example 34 was used in place of the compound of Reference Example 3 and methanesulfonyl chloride was used in place of propionyl chloride, N-(2-chloro-2'-(trifluoromethoxy)-[1,1'-biphenyl]-4-yl)-1-(3-(N-methylmethyl sulfonamide)propanoyl)piperidine-2-carboxamide (hereinafter referred to as the compound of Example 36) (0.0380 g, 0.0676 mmol, 86.2%) was obtained as a white solid.

¹H-NMR (400 MHz, CDCl₃) δ: 1.50-1.98(m, 5H), 2.35(d, J=13.5 Hz, 1H), 2.76(dt, J=15.9, 7.0 Hz, 1H), 2.86(s, 3H), 2.83-2.89(m, 1H), 2.95(s, 3H), 3.20(td, J=13.5, 2.7 Hz, 1H), 3.50-3.57(m, 2H), 3.85(d, J=13.5 Hz, 1H), 5.31(d, J=5.0 Hz, 1H), 7.21(d, J=8.2 Hz, 1H), 7.30-7.36(m, 3H), 7.40-7.52(m, 2H), 7.80-7.83(m, 1H), 8.42(br, 1H).

ESI-MS: m/z=584(M+H)⁺.

Reference Example 23

Synthesis of N-(2-chloro-2'-(trifluoromethoxy)-[1,1'-biphenyl]-4-yl)-1-(2-(ethylamino)acetyl)piperidine-2-carboxamide

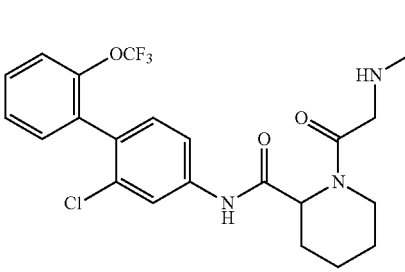

To a dichloromethane (1.0 mL) solution of the compound of Reference Example 5 (0.0400 g, 0.0877 mmol), a dichloromethane (0.0600 mL) solution of acetaldehyde (0.00464 g, 0.105 mmol), acetic acid (0.000502 mL, 0.00877 mmol), and sodium triacetoxyborohydride (0.0279 m g, 0.132 mmol) were added at 0° C. and the temperature was raised to room temperature, followed by stirring for 2.5 hours. To the reaction solution, an aqueous saturated sodium hydrogen carbonate solution was added, and the solution was extracted with chloroform. The organic layer was washed with saturated brine, dried over anhydrous sodium sulfate and filtered, and then the filtrate was concentrated under reduced pressure. The residue was purified by column chromatography (amine silica gel, n-hexane/ethyl acetate=40/60 to 0/100) to obtain N-(2-chloro-2'-(trifluoromethoxy)-[1,1'-biphenyl]-4-yl)-1-(2-(ethylamino)acetyl)piperidine-2-carboxamide (hereinafter referred to as the compound of Reference Example 23) (0.0193 g, 0.00399 mmol, 45.5%) as a white solid.

$^1$H-NMR (400 MHz, CDCl$_3$) δ: 1.17(t, J=7.1 Hz, 3H), 1.38-1.80(m, 5H), 1.90-2.00(m, 1H), 2.30-2.45(m, 1H), 2.55-2.90(m, 2H), 3.16(t, J=13.3 Hz, 1H), 3.56(s, 2H), 3.70-3.76(m, 1H), 5.29(d, J=4.9 Hz, 1H), 7.20-7.45(m, 6H), 7.70-7.90(m, 1H), 8.46(s, 1H).

ESI-MS: m/z=484(M+H)$^+$.

Example 37

Synthesis of N-(2-chloro-2'-(trifluoromethoxy)-[1,1'-biphenyl]-4-yl)-1-(2-(N-ethylmethylsulfonamide)acetyl)piperidine-2-carboxamide

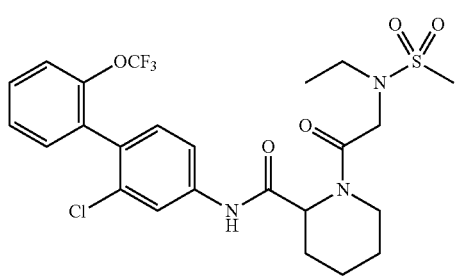 [SMILES: CCN(CC(=O)N1CCCCC1C(=O)Nc1ccc(-c2ccccc2OC(F)(F)F)c(Cl)c1)S(C)(=O)=O]

According to the same procedure as in Example 3, except that the compound of Reference Example 23 was used in place of the compound of Reference Example 3 and methanesulfonyl chloride was used in place of propionyl chloride, N-(2-chloro-2'-(trifluoromethoxy)-[1,1'-biphenyl]-4-yl)-1-(2-(N-ethylmethylsulfonamide)acetyl)piperidine-2-carboxamide (hereinafter referred to as the compound of Example 37) (0.0175 g, 0.0311 mmol, 78.1%) was obtained as a white solid.

$^1$H-NMR (400 MHz, CDCl$_3$) δ: 1.25(t, J=7.1 Hz, 3H), 1.50-1.90(m, 5H), 2.38(d, J=13.0 Hz, 1H), 3.07(s, 3H), 3.25(t, J=13.0 Hz, 1H), 3.43(q, J=7.1 Hz, 2H), 3.76(d, J=13.0 Hz, 1H), 4.14(d, J=17.0 Hz, 1H), 4.30(d, J=17.0 Hz, 1H), 5.27(d, J=4.6 Hz, 1H), 7.21(d, J=8.3 Hz, 1H), 7.29-7.36(m, 3H), 7.40-7.45(m, 2H), 7.83-7.85(m, 1H), 8.23(br, 1H).

ESI-MS: m/z=584(M+Na)$^+$.

Reference Example 24

Synthesis of tert-butyl (R)-(3-(2-((2-chloro-2'-(trifluoromethoxy)-[1,1'-biphenyl]-4-yl)carbamoyl)piperidin-1-yl)-3-oxopropyl)carbamate

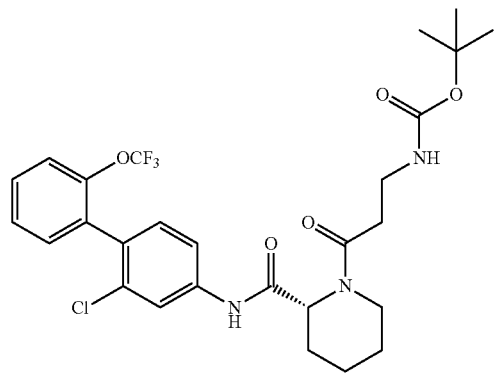 [SMILES: CC(C)(C)OC(=O)NCCC(=O)N1CCCC[C@@H]1C(=O)Nc1ccc(-c2ccccc2OC(F)(F)F)c(Cl)c1]

According to the same procedure as in Example 4, except that 3-((tert-butoxycarbonyl)amino)propanoic acid was used in place of 2-methoxyacetic acid and the compound of Reference Example 8 was used in place of the compound of Reference Example 3, tert-butyl (R)-(3-(2-((2-chloro-2'-(trifluoromethoxy)-[1,1'-biphenyl]-4-yl)carbamoyl)piperidin-1-yl)-3-oxopropyl)carbamate (hereinafter referred to as the compound of Reference Example 24) (0.104 g, 0.182 mmol, 96.7%) was obtained as a white solid.

$^1$H-NMR (400 MHz, CDCl$_3$) δ: 1.39(s, 9H), 1.50-1.90 (5H, m), 2.35(d, J=13.7 Hz, 1H), 2.55-2.75(m, 2H), 3.20(t, J=12.8 Hz, 1H), 3.41-3.49(m, 1H), 3.50-3.60(m, 1H), 3.80 (d, J=13.7 Hz, 1H), 5.17(br, 1H), 5.33(d, J=4.9 Hz, 1H), 7.20(d, J=8.3 Hz, 1H), 7.29-7.60(m, 5H), 7.70-7.89(m, 1H), 8.65(br, 1H).

ESI-MS: m/z=570(M+H)$^+$.

Example 38

Synthesis of (R)-1-(3-aminopropanoyl)-N-(2-chloro-2'-(trifluoromethoxy)-[1,1'-biphenyl]-4-yl)piperidine-2-carboxamide

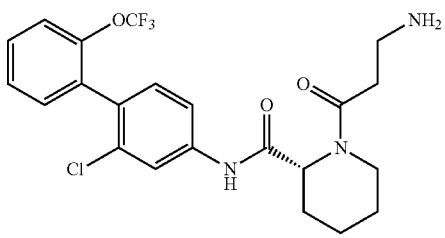 [SMILES: NCCC(=O)N1CCCC[C@@H]1C(=O)Nc1ccc(-c2ccccc2OC(F)(F)F)c(Cl)c1]

According to the same procedure as in Reference Example 5, except that the compound of Reference Example 24 was used in place of the compound of Reference Example 4, (R)-1-(3-aminopropanoyl)-N-(2-chloro-2'-(trifluoromethoxy)-[1,1'-biphenyl]-4-yl)piperidine-2-carboxamide (hereinafter referred to as the compound of Example 38) (0.497 g, 0.106 mmol, 58.5%) was obtained as a white solid.

$^1$H-NMR (400 MHz, CDCl$_3$) δ: 1.46-1.82(m, 5H), 2.43(d, J=13.1 Hz, 1H) 2.56(dt, J=15.3, 6.2 Hz, 1H), 2.71-2.79(m, 1H), 3.09-3.21(m, 3H), 3.88(d, J=13.1 Hz, 1H), 5.43(d, J=5.0 Hz, 1H), 7.19(d, J=8.2 Hz, 1H), 7.29-7.36(m, 3H), 7.40-7.85(m, 3H), 8.96(br, 1H).

ESI-MS: m/z=470(M+H)$^+$.

Example 39

Synthesis of N-(2-chloro-2'-(trifluoromethoxy)-[1,1'-biphenyl]-4-yl)-1-(3-(methylthio)propanoyl)piperidine-2-carboxamide

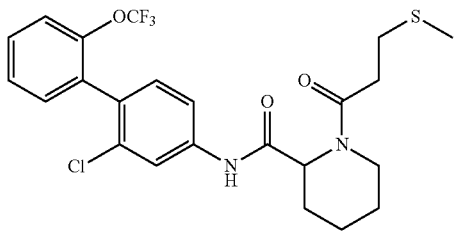 [SMILES: CSCCC(=O)N1CCCCC1C(=O)Nc1ccc(-c2ccccc2OC(F)(F)F)c(Cl)c1]

According to the same procedure as in Example 4, except that 3-(methylthio)propanoic acid was used in place of 2-methoxyacetic acid, N-(2-chloro-2'-(trifluoromethoxy)-[1,1'-biphenyl]-4-yl)-1-(3-(methylthio)propanoyl)piperidine-2-carboxamide (hereinafter referred to as the compound of Example 39) (0.0489 g, 0.0976 mmol, 97.4%) was obtained as a white solid.

$^1$H-NMR (400 MHz, CDCl$_3$) δ: 1.51-1.90(m, 5H), 2.18(s, 3H), 2.36(d, J=13.9 Hz, 1H), 2.68-2.77(m, 1H), 2.80-2.99 (m, 3H), 3.17(td, J=13.2, 2.6 Hz, 1H), 3.86(d, J=12.4 Hz, 1H), 5.37(d, J=4.9 Hz, 1H), 7.20(d, J=8.3 Hz, 1H), 7.30-7.52(m, 5H), 7.66-7.90(m, 1H), 8.49(br, 1H).

ESI-MS: m/z=501(M+H)$^+$.

Example 40

Synthesis of N-(2-chloro-2'-(trifluoromethoxy)-[1,1'-biphenyl]-4-yl)-1-(3-(methylsulfonyl)propanoyl)piperidine-2-carboxamide

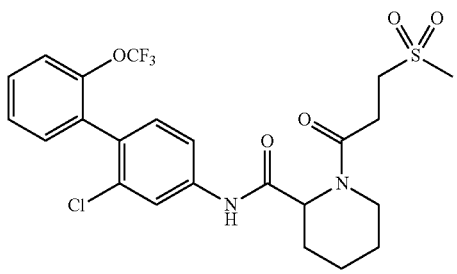 [SMILES: CS(=O)(=O)CCC(=O)N1CCCCC1C(=O)Nc1ccc(-c2ccccc2OC(F)(F)F)c(Cl)c1]

To a dichloromethane (1.0 mL) solution of the compound of Example 39 (0.0480 g, 0.0958 mmol), 3-chloroperbenzoic acid (0.0496 g, 0.287 mmol) was added at 0° C. and the temperature was raised to room temperature, followed by stirring for 17 hours. To the reaction solution, an aqueous saturated sodium thiosulfate solution and saturated sodium hydrogen carbonate were added, and the solution was extracted with chloroform. The organic layer was washed with saturated brine, dried over anhydrous sodium sulfate and filtered, and then the filtrate was concentrated under reduced pressure. The residue was purified by column chromatography (silica gel, n-hexane/ethyl acetate=50/50 to 25/75) to obtain N-(2-chloro-2'-(trifluoromethoxy)-[1,1'-biphenyl]-4-yl)-1-(3-(methylsulfonyl)propanoyl)piperidine-2-carboxamide (hereinafter referred to as the compound of Example 40) (0.0412 g, 0.0773 mmol, 80.6%) as a white solid.

$^1$H-NMR (400 MHz, CDCl$_3$) δ: 1.50-1.82(m, 5H), 2.45-2.48(m, 1H), 2.79(td, J=11.0, 5.9 Hz, 1H), 3.06(s, 3H), 3.18-3.27(m, 2H), 3.40(dt, J=13.8, 5.5 Hz, 1H), 3.77-3.79 (m, 1H), 3.93-3.96(m, 1H), 5.41(d, J=5.4 Hz, 1H), 7.20(d, J=8.5 Hz, 1H), 7.30-7.36(m, 3H), 7.40-7.44(m, 1H), 7.51-7.53(m, 1H), 7.86-7.89(m, 1H), 8.28(br, 1H).

ESI-MS: m/z=533(M+H)$^+$.

Reference Example 25

Synthesis of tert-butyl (R)-(3-(2-((2-chloro-2'-(trifluoromethoxy)-[1,1'-biphenyl]-4-yl)carbamoyl)piperidin-1-yl)-3-oxopropyl)(methyl)carbamate

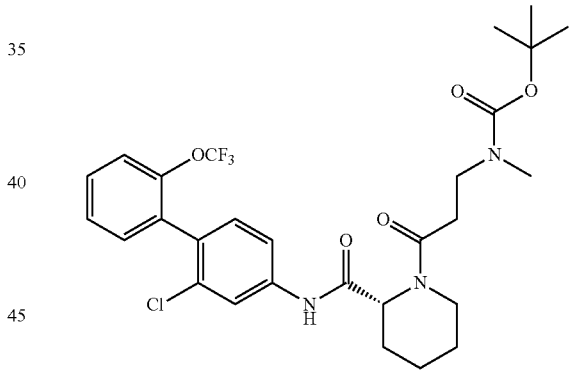

According to the same procedure as in Example 4, except that 3-((tert-butoxycarbonyl)(methyl)amino)propanoic acid was used in place of 2-methoxyacetic acid and the compound of Reference Example 8 was used in place of the compound of Reference Example 3, tert-butyl (R)-(3-(2-((2-chloro-2'-(trifluoromethoxy)-[1,1'-biphenyl]-4-yl)carbamoyl)piperidin-1-yl)-3-oxopropyl)(methyl)carbamate (hereinafter referred to as the compound of Reference Example 25) (0.117 g, 0.201 mmol, 91.5%) was obtained as a white solid.

$^1$H-NMR (400 MHz, CDCl$_3$) δ: 1.35(s, 9H), 1.30-1.77(m 5H), 2.37-2.80(m, 3H), 2.93(s, 3H), 3.18-3.30(m, 2H), 3.84 (d, J=13.7 Hz, 1H), 3.95-4.03(m, 1H), 5.38-5.42(m, 1H), 7.20(d, J=8.3 Hz, 1H), 7.31-7.46(m, 4H), 7.66-7.72(m, 1H), 7.90-7.92(m, 1H), 9.10(br, 1H).

ESI-MS: m/z=584(M+H)$^+$.

Example 41

Synthesis of (R)-N-(2-chloro-2'-(trifluoromethoxy)-[1,1'-biphenyl]-4-yl)-1-(3-(methylamino)propanoyl)piperidine-2-carboxamide

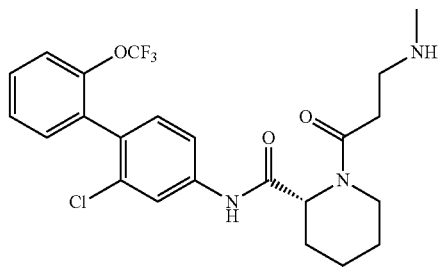 [SMILES: CNCCC(=O)N1CCCC[C@@H]1C(=O)Nc1ccc(-c2ccccc2OC(F)(F)F)c(Cl)c1]

According to the same procedure as in Reference Example 5, except that the compound of Reference Example 25 was used in place of the compound of Reference Example 4, (R)-N-(2-chloro-2'-(trifluoromethoxy)-[1,1'-biphenyl]-4-yl)-1-(3-(methylamino)propanoyl)piperidine-2-carboxamide (hereinafter referred to as the compound of Example 41) (0.748 g, 0.155 mmol, 77.1%) was obtained as a white solid.

$^1$H-NMR (400 MHz, CDCl$_3$) δ: 1.46-1.83(m, 5H), 2.47(s, 3H), 2.40-2.48(m, 1H), 2.75-2.83(m, 1H), 2.94-2.99(m, 2H), 3.16(td, J=13.1, 2.6 Hz, 1H), 3.88(d, J=13.1 Hz, 1H), 5.41(d, J=5.4 Hz, 1H), 7.21(d, J=8.3 Hz, 1H), 7.30-7.81(m, 6H), 8.80(br, 1H).

ESI-MS: m/z=484(M+H)$^+$.

Example 42

Synthesis of N-(2-chloro-2'-(trifluoromethoxy)-[1,1'-biphenyl]-4-yl)-1-(3-hydroxypropanoyl)piperidine-2-carboxamide

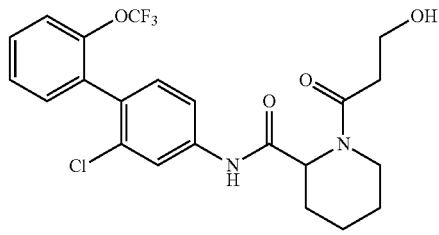 [SMILES: O=C(Nc1ccc(-c2ccccc2OC(F)(F)F)c(Cl)c1)C1CCCCN1C(=O)CCO]

According to the same procedure as in Example 4, except that 3-hydroxypropanoic acid was used in place of 2-methoxyacetic acid, N-(2-chloro-2'-(trifluoromethoxy)-[1,1'-biphenyl]-4-yl)-1-(3-hydroxypropanoyl)piperidine-2-carboxamide (hereinafter referred to as the compound of Example 42) (0.212 g, 0.450 mmol, 59.9%) was obtained as a white solid.

$^1$H-NMR (400 MHz, CDCl$_3$) δ: 1.50-1.92(m, 4H), 2.35(d, J=14.1 Hz, 1H), 2.64-2.80(m, 2H), 3.06(t, J=6.3 Hz, 1H), 3.19(td, J=13.2, 2.4 Hz, 1H), 3.83(d, J=14.1 Hz, 1H), 3.98(q, J=5.4 Hz, 2H), 5.34(d, J=5.4 Hz, 1H), 7.21(d, J=8.0 Hz, 1H), 7.30-7.44(m, 6H), 7.70-7.90(brm, 1H), 8.39(br, 1H).

ESI-MS: m/z=471(M+H)$^+$.

Example 43

Synthesis of methyl 3-(2-((2-chloro-2'-(trifluoromethoxy)-[1,1'-biphenyl]-4-yl)carbamoyl)piperidin-1-yl)-3-oxopropanoate

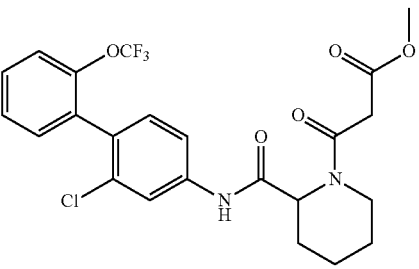 [SMILES: COC(=O)CC(=O)N1CCCCC1C(=O)Nc1ccc(-c2ccccc2OC(F)(F)F)c(Cl)c1]

According to the same procedure as in Example 3, except that methyl 3-chloro-3-oxopropanoate was used in place of propionyl chloride, methyl 3-(2-((2-chloro-2'-(trifluoromethoxy)-[1,1'-biphenyl]-4-yl)carbamoyl)piperidin-1-yl)-3-oxopropanoate (hereinafter referred to as the compound of Example 43) (0.0500 g, 0.100 mmol, 80.0%) was obtained as a white solid.

$^1$H-NMR (400 MHz, CDCl$_3$) δ: 1.50-1.80(m, 5H), 2.57-2.62(m, 1H), 3.16-3.25(m, 1H), 3.57(d, J=17.2 Hz, 1H), 3.59-3.65(m, 1H), 3.84(s, 3H), 3.85(d, J=17.2 Hz, 2H), 5.49(s, 1H), 7.22(d, J=8.2 Hz, 1H), 7.30-7.37(m, 3H), 7.40-7.44(m, 1H), 7.92-7.95(m, 1H), 8.87(br, 1H).

ESI-MS: m/z=499(M+H)$^+$.

Example 44

Synthesis of methyl 4-(2-((2-chloro-2'-(trifluoromethoxy)-[1,1'-biphenyl]-4-yl)carbamoyl)piperidin-1-yl)-4-oxobutanoate

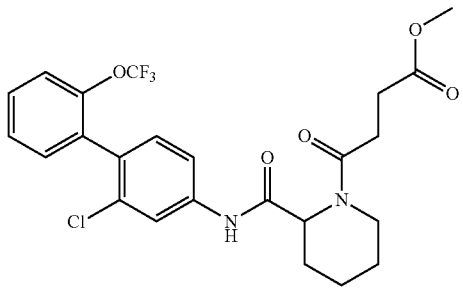 [SMILES: COC(=O)CCC(=O)N1CCCCC1C(=O)Nc1ccc(-c2ccccc2OC(F)(F)F)c(Cl)c1]

According to the same procedure as in Example 3, except that methyl 4-chloro-4-oxobutanoate was used in place of propionyl chloride, methyl 4-(2-((2-chloro-2'-(trifluoromethoxy)-[1,1'-biphenyl]-4-yl)carbamoyl)piperidin-1-yl)-4-oxobutanoate (hereinafter referred to as the compound of Example 44) (0.0390 g, 0.0760 mmol, quantitative) was obtained as a white solid.

$^1$H-NMR (400 MHz, CDCl$_3$) δ: 1.52-1.60(m, 5H), 2.42-2.60(m, 2H), 2.62-2.70(m, 1H), 2.88-2.96(m, 1H), 2.99-3.08(m, 1H), 3.22(d, J=14.6 Hz, 1H), 3.74(s, 3H), 3.97(d, J=14.6 Hz, 1H), 5.46(d, J=5.4 Hz, 1H), 7.21(d, J=8.3 Hz, 1H), 7.28-7.44(m, 6H), 8.49(br, 1H)

ESI-MS: m/z=513(M+H)$^+$.

Example 45

Synthesis of N-(2-chloro-2'-(trifluoromethoxy)-[1,1'-biphenyl]-4-yl)-1-(3-methoxypropanoyl)piperidine-2-carboxamide

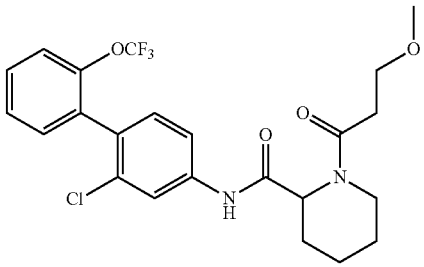 [SMILES: COCCC(=O)N1CCCCC1C(=O)Nc1ccc(-c2ccccc2OC(F)(F)F)c(Cl)c1]

According to the same procedure as in Reference Example 2, except that 1-(3-methoxypropanoyl)piperidine-2-carboxylic acid was used in place of 1-(tert-butoxycarbonyl)piperidine-2-carboxylic acid, N-(2-chloro-2'-(trifluoromethoxy)-[1,1'-biphenyl]-4-yl)-1-(3-methoxypropanoyl)piperidine-2-carboxamide (hereinafter referred to as the compound of Example 45) (0.0467 g, 0.0963 mmol, 50.6%) was obtained as a white solid.

$^1$H-NMR (400 MHz, CDCl$_3$) δ: 1.46-1.87(m, 5H), 2.39(d, J=13.9 Hz, 1H), 2.64(dt, J=15.0, 5.7 Hz, 1H), 2.85-2.92(m, 1H), 3.14(td, J=13.1, 2.3 Hz, 1H), 3.38(s, 3H), 3.67-3.78(m, 1H), 3.81-3.86(m, 1H), 3.92(d, J=13.9 Hz, 1H), 5.40(d, J=4.9 Hz, 1H), 7.21(d, J=8.3 Hz, 1H), 7.29-7.80(m, 6H), 8.46(s, 1H).

ESI-MS: m/z=483(M−H)$^−$.

Example 46

Synthesis of N-(2-chloro-2'-(trifluoromethoxy)-[1,1'-biphenyl]-4-yl)-1-(1-methyl-1H-pyrazole-4-carbonyl)piperidine-2-carboxamide

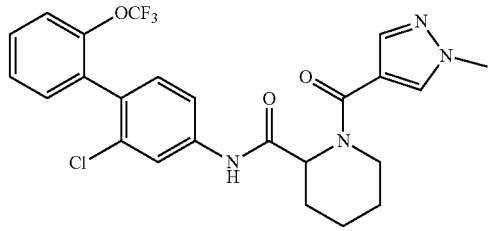 [SMILES: Cn1cc(C(=O)N2CCCCC2C(=O)Nc2ccc(-c3ccccc3OC(F)(F)F)c(Cl)c2)cn1]

According to the same procedure as in Example 4, except that 1-methyl-1H-pyrazole-4-carboxylic acid was used in place of 2-methoxyacetic acid, N-(2-chloro-2'-(trifluoromethoxy)-[1,1'-biphenyl]-4-yl)-1-(1-methyl-1H-pyrazole-4-carbonyl)piperidine-2-carboxamide (hereinafter referred to as the compound of Example 46) (0.0314 g, 0.0619 mmol, 82.4%) was obtained as a white solid.

$^1$H-NMR (400 MHz, CDCl$_3$) δ: 1.62-1.71(m, 2H), 1.78-1.87(m, 2H), 1.99-2.11(m, 1H), 2.37(d, J=12.9 Hz, 1H), 3.08-3.21(m, 1H), 3.96(s, 3H), 4.13-4.23(m, 1H), 5.18-5.20(m, 1H), 7.22(d, J=8.3 Hz, 1H), 7.27-7.90(m, 6H), 7.70(s, 1H), 7.81(s, 1H), 9.18(br, 1H).

ESI-MS: m/z=507(M+H)$^+$.

Example 47

Synthesis of N-(2-chloro-2'-(trifluoromethoxy)-[1,1'-biphenyl]-4-yl)-1-(1-methyl-1H-imidazole-4-carbonyl)piperidine-2-carboxamide

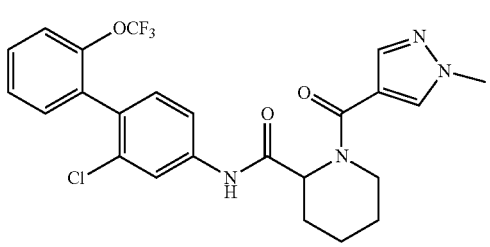 [SMILES: Cn1cc(C(=O)N2CCCCC2C(=O)Nc2ccc(-c3ccccc3OC(F)(F)F)c(Cl)c2)cn1]

According to the same procedure as in Example 4, except that 1-methyl-1H-imidazole-4-carboxylic acid was used in place of 2-methoxyacetic acid, N-(2-chloro-2'-(trifluoromethoxy)-[1,1'-biphenyl]-4-yl)-1-(1-methyl-1H-imidazole-4-carbonyl)piperidine-2-carboxamide (hereinafter referred to as the compound of Example 47) (0.0369 g, 0.0728 mmol, 96.9%) was obtained as a white solid.

$^1$H-NMR (400 MHz, CDCl$_3$) δ: 1.45-1.83(m, 4H), 2.15-2.32(m, 2H), 2.75-2.87(m, 1H), 3.79(s, 3H), 4.55-4.65(m, 1H), 5.31-5.37(m, 1H), 7.21(d, J=8.3 Hz, 1H), 7.31-7.63(m, 7H), 7.75-7.90(m, 1H), 11.47(br, 1H).

ESI-MS: m/z=507(M+H)$^+$.

Example 48

Synthesis of N-(2-chloro-2'-(trifluoromethoxy)-[1,1'-biphenyl]-4-yl)-1-(1H-pyrazole-4-carbonyl)piperidine-2-carboxamide

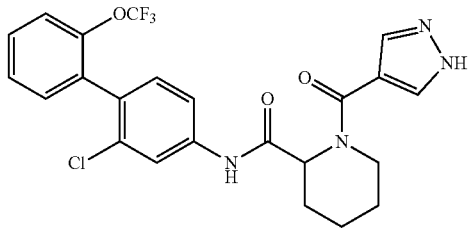 [SMILES: O=C(Nc1ccc(-c2ccccc2OC(F)(F)F)c(Cl)c1)C1CCCCN1C(=O)c1cn[nH]c1]

According to the same procedure as in Example 4, except that 1H-pyrazole-4-carboxylic acid was used in place of 2-methoxyacetic acid, N-(2-chloro-2'-(trifluoromethoxy)-[1,1'-biphenyl]-4-yl)-1-(1H-pyrazole-4-carbonyl)piperidine-2-carboxamide (hereinafter referred to as the compound of Example 48) (0.0163 g, 0.0331 mmol, 44.0%) was obtained as a white solid.

$^1$H-NMR (400 MHz, CDCl$_3$) δ: 1.45-1.90(m, 4H), 1.95-2.17(m, 1H), 2.33-2.43(m, 1H), 3.15-3.26(m, 1H), 4.09-4.21(m, 1H), 5.20-5.27(m, 1H), 7.22(d, J=8.5 Hz, 1H), 7.28-7.52(m, 5H), 7.70-8.00(m, 3H), 9.16(br, 1H), 10.79(br, 1H).

ESI-MS: m/z=493(M+H)$^+$.

Reference Example 26

Synthesis of methyl 1-(2-(N-methylmethylsulfonamide)acetyl)piperidine-2-carboxylate

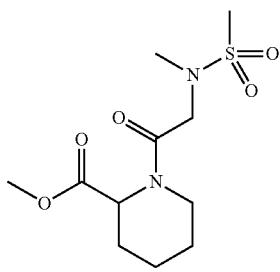 [SMILES: COC(=O)C1CCCCN1C(=O)CN(C)S(C)(=O)=O]

According to the same procedure as in Example 4, except that the compound of Reference Example 20 was used in place of 2-methoxyacetic acid and methyl piperidine-2-carboxylate hydrochloride was used in place of the compound of Reference Example 3, 1-(2-(N-methylmethylsulfonamide)acetyl)piperidine-2-carboxylic acidmethyl (hereinafter referred to as the compound of Reference Example 26) (0.934 g, 3.19 mmol, 82.0) was obtained as a white solid.

$^1$H-NMR (400 MHz, CDCl$_3$) δ: 1.24-1.76(m, 5H), 2.25-2.32(m, 1H), 2.99(s, 3H), 3.00(s, 3H), 3.25(td, J=13.0, 3.2 Hz, 1H), 3.58-3.64(m, 1H), 3.75(d, J=4.6 Hz, 3H), 4.11(d, J=17.1 Hz, 1H), 4.30(d, J=17.1 Hz, 1H), 5.25(d, J=5.6 Hz, 1H).

ESI-MS: m/z=293(M+H)$^+$.

Reference Example 27

Synthesis of 1-(2-(N-methylmethylsulfonamide)acetyl)piperidine-2-carboxylic Acid

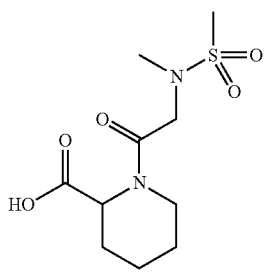 [SMILES: CN(CC(=O)N1CCCCC1C(=O)O)S(C)(=O)=O]

To a methanol (10.0 mL) solution of the compound of Reference Example 26 (0.933 g, 3.19 mmol), an aqueous 1M sodium hydroxide solution (3.83 mL, 3.83 mmol) was added at 0° C. and the temperature was raised to room temperature, followed by stirring for 17 hours. To the reaction solution, 1M hydrochloric acid was added, and the solution was extracted with chloroform. The organic layer was washed with saturated brine, dried over anhydrous sodium sulfate and filtered, and then the filtrate was concentrated under reduced pressure to obtain crude 1-(2-(N-methylmethylsulfonamide)acetyl)piperidine-2-carboxylic acid (hereinafter referred to as the compound of Reference Example 27) (0.812 g) as a white solid. The compound of Reference Example 27 was directly used for the subsequent reaction.

(400 MHz, CDCl$_3$) δ: 1.18-1.75(m, 5H), 2.30(d, J=13.1 Hz, 1H), 2.98(s, 3H), 2.99(s, 3H), 3.24(t, J=12.0 Hz, 1H), 3.63(d, J=13.1 Hz, 1H), 4.13(d, J=17.2 Hz, 1H), 4.27(d, J=17.2 Hz, 1H), 5.24(d, J=4.1 Hz, 1H).

ESI-MS: m/z=279(M+H)$^+$.

Reference Example 28

Synthesis of N-(4-bromo-3-chlorophenyl)-1-(2-(N-methylmethylsulfonamide)acetyl)piperidine-2-carboxamide

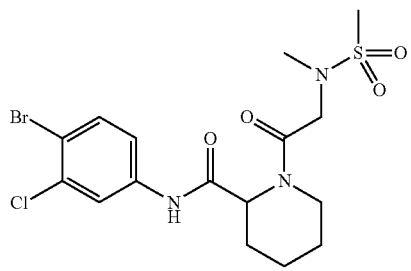 [SMILES: CN(CC(=O)N1CCCCC1C(=O)Nc1ccc(Br)c(Cl)c1)S(C)(=O)=O]

According to the same procedure as in Reference Example 2, except that the compound of Reference Example 27 was used in place of 1-(tert-butoxycarbonyl)piperidine-2-carboxylic acid and 4-bromo-3-chloroaniline was used in place of the compound of Reference Example 1, N-(4-bromo-3-chlorophenyl)-1-(2-(N-methylmethylsulfonamide)acetyl)piperidine-2-carboxamide (hereinafter referred to as the compound of Reference Example 28) (0.296 g, 0.634 mmol, 58.8%) was obtained as a white solid.

$^1$H-NMR (400 MHz, CDCl$_3$) δ: 1.49-1.85(m, 5H), 2.34(d, J=12.8 Hz, 1H), 3.03(s, 3H), 3.03(s, 3H), J=12.8 Hz, 1H), 3.71(d, J=12.8 Hz, 1H), 4.12(d, J=16.7 Hz, 1H), 4.23(d, J=16.7 Hz, 1H), 5.22(d, J=4.9 Hz, 1H), 7.20-7.24(m, 1H), 7.50(dd, J=8.5, 2.0 Hz, 1H), 7.84(t, J=2.3 Hz, 1H), 8.20(br, 1H).

ESI-MS: m/z=467(M+H)$^+$.

Example 49

Synthesis of N-(2-chloro-2'-isopropoxy-[1,1'-biphenyl]-4-yl)-1-(2-(N-methylmethylsulfonamide)acetyl)piperidine-2-carboxamide

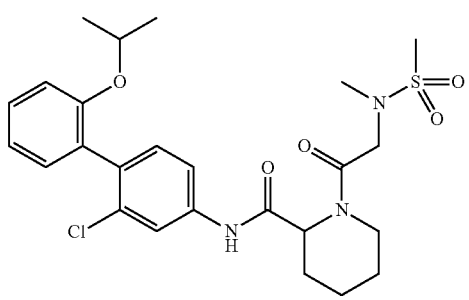 [SMILES: CC(C)Oc1ccccc1-c1ccc(NC(=O)C2CCCCN2C(=O)CN(C)S(C)(=O)=O)cc1Cl]

According to the same procedure as in Reference Example 1, except that 2-isopropoxyphenylboronic acid was used in place of 2-trifluoromethoxyphenylboronic acid and the compound of Reference Example 28 was used in place of 4-bromo-3-chloroaniline, N-(2-chloro-2'-isopropoxy-[1,1'-biphenyl]-4-yl)-1-(2-(N-methylmethylsulfonamide)acetyl)piperidine-2-carboxamide (hereinafter referred to as the compound of Example 49) (0.0253 g, 0.0485 mmol, 75.3%) was obtained as a white solid.

$^1$H-NMR (400 MHz, CDCl$_3$) δ: 1.20(d, J=6.0 Hz, 6H), 1.50-1.88(m, 5H), 2.31-2.39(m, 1H), 3.05(s, 3H), 3.05(s, 3H), 3.21-3.28(m, 1H), 3.69-3.74(m, 1H), 4.19(d, J=16.8 Hz, 1H), 4.25(d, J=16.8 Hz, 1H), 4.41(t, J=6.0 Hz, 1H), 5.23-5.26(m, 1H), 6.95-7.00(m, 2H), 7.17(dd, J=7.4, 2.0 Hz, 1H), 7.22-7.37(m, 3H), 7.76(d, J=2.0 Hz, 1H), 8.11(s, 1H).
ESI-MS: m/z=523(M+H)$^+$.

Example 50

Synthesis of N-(2-chloro-2'-(trifluoromethoxy)-[1,1'-biphenyl]-4-yl)-1-(2-(1-methyl-1H-imidazol-2-yl)acetyl)piperidine-2-carboxamide

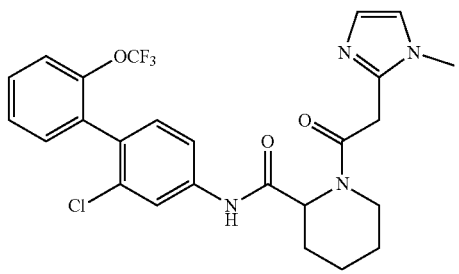 [SMILES: Cn1ccnc1CC(=O)N1CCCCC1C(=O)Nc1ccc(-c2ccccc2OC(F)(F)F)c(Cl)c1]

According to the same procedure as in Example 4, except that 2-(1-methyl-1H-imidazol-2-yl)acetic acid was used in place of 2-methoxyacetic acid, N-(2-chloro-2'-(trifluoromethoxy)-[1,1'-biphenyl]-4-yl)-1-(2-(1-methyl-1H-imidazol-2-yl)acetyl)piperidine-2-carboxamide (hereinafter referred to as the compound of Example 50) (0.0341 g, 0.0654 mmol, 87.0%) was obtained as a white solid.

$^1$H-NMR (400 MHz, CDCl$_3$) δ: 1.49-1.80(m, 5H), 2.67-2.74(m, 1H), 3.20-3.27(m, 1H), 3.54-3.62(m, 1H), 3.63(s, 3H), 3.73(d, J=15.9 Hz, 1H), 4.05(d, J=15.9 Hz, 1H), 5.59-5.63(m, 1H), 6.89-6.98(m, 2H), 7.20-7.29(m, 1H), 7.32-7.37(m, 3H), 7.39-7.45(m, 1H), 7.71-7.99(m, 2H), 10.64(br, 1H).
ESI-MS: m/z=521(M+H)$^+$.

Reference Example 29

Synthesis of N-(4-bromo-3-fluorophenyl)-1-(2-(N-methylmethylsulfonamide)acetyl)piperidine-2-carboxamide

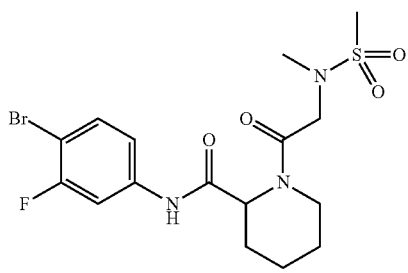 [SMILES: CN(CC(=O)N1CCCCC1C(=O)Nc1ccc(Br)c(F)c1)S(C)(=O)=O]

According to the same procedure as in Reference Example 2, except that the compound of Reference Example 27 was used in place of 1-(tert-butoxycarbonyl)piperidine-2-carboxylic acid and 4-bromo-3-fluoroaniline was used in place of the compound of Reference Example 1, N-(4-bromo-3-fluorophenyl)-1-(2-(N-methylmethylsulfonamide)acetyl)piperidine-2-carboxamide (hereinafter referred to as the compound of Reference Example 29) (0.0253 g, 0.0562 mmol, 52.1%) was obtained as a white solid.

$^1$H-NMR (400 MHz, CDCl$_3$) δ: 1.48-1.83(m, 5H), 2.31-2.39(m, 1H), 3.03(s, 3H), 3.03(s, 3H), 3.16-3.23(m, 1H), 3.68-3.75(m, 1H), 4.10(d, J=16.6 Hz, 1H), 4.24(d, J=16.6 Hz, 1H), 5.21-5.24(m, 1H), 7.06(dd, J=9.0, 2.0 Hz, 1H), 7.43(t, J=8.2 Hz, 1H), 7.63(dd, J=10.5, 2.4 Hz, 1H), 8.24(br, 1H).
ESI-MS: m/z=451(M+H)$^+$.

Example 51

Synthesis of N-(2-fluoro-2'-(trifluoromethoxy)-[1,1'-biphenyl]-4-yl)-1-(2-(N-methylmethylsulfonamide)acetyl)piperidine-2-carboxamide

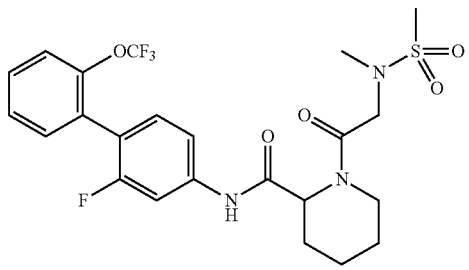 [SMILES: CN(CC(=O)N1CCCCC1C(=O)Nc1ccc(-c2ccccc2OC(F)(F)F)c(F)c1)S(C)(=O)=O]

According to the same procedure as in Reference Example 1, except that the compound of Reference Example 29 was used as 4-bromo-3-chloroaniline, N-(2-fluoro-2'-(trifluoromethoxy)-[1,1'-biphenyl]-4-yl)-1-(2-(N-methylmethylsulfonamide)acetyl)piperidine-2-carboxamide (hereinafter referred to as the compound of Example 51) (0.0132 g, 0.0248 mmol, 44.7%) was obtained as a white solid.

$^1$H-NMR (400 MHz, CDCl$_3$) δ: 1.45-1.90(m, 5H), 2.33-2.41(m, 1H), 3.05(s, 6H), 3.20-3.29(m, 1H), 3.69-3.76(m, 1H), 4.17(d, J=16.8 Hz, 1H), 4.25(d, J=16.8 Hz, 1H), 5.23-5.27(m, 1H), 7.20-7.44(m, 6H), 7.62(dd, J=11.7, 2.0 Hz, 1H), 8.24(br, 1H).

Example 52

Synthesis of 1-(2-(1H-imidazol-1-yl)acetyl)-N-(2-chloro-2'-(trifluoromethoxy)-[1,1'-biphenyl]-4-yl)piperidine-2-carboxamide

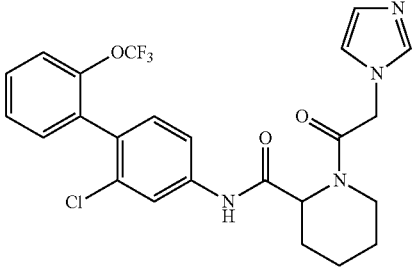 [SMILES: O=C(Nc1ccc(-c2ccccc2OC(F)(F)F)c(Cl)c1)C1CCCCN1C(=O)Cn1ccnc1]

According to the same procedure as in Example 4, except that 1-imidazoleacetic acid was used in place of 2-methoxyacetic acid, 1-(2-(1H-imidazol-1-yl)acetyl)-N-(2-chloro-2'-(trifluoromethoxy)-[1,1'-biphenyl]-4-yl)piperidine-2-carboxamide (hereinafter referred to as the compound of Example 52) (0.0189 g, 0.0373 mmol, 49.6%) was obtained as a white solid.

¹H-NMR (400 MHz, CDCl₃) δ: 1.44-2.05(m, 5H), 2.23-2.31(m, 1H), 3.37-3.47(m, 1H), 3.67-3.74(m, 1H), 4.86(d, J=16.6 Hz, 1H), 4.91(d, J=16.6 Hz, 1H), 5.16-5.22(m, 1H), 6.97(s, 1H), 7.13(s, 1H), 7.20(d, J=8.3 Hz, 1H), 7.29-7.37 (m, 4H), 7.40-7.45(m, 1H), 7.53(s, 1H), 7.70-7.87(m, 1H), 8.41(br, 1H).

ESI-MS: m/z=507(M+H)⁺.

Example 53

Synthesis of 1-(2-(1H-tetrazol-1-yl)acetyl)-N-(2-chloro-2'-(trifluoromethoxy)-[1,1'-biphenyl]-4-yl)piperidine-2-carboxamide

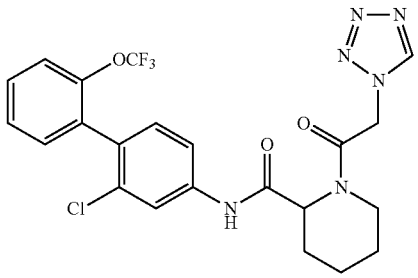

According to the same procedure as in Example 4, except that 1H-tetrazole-1-acetic acid was used in place of 2-methoxyacetic acid, 1-(2-(1H-tetrazol-1-yl)acetyl)-N-(2-chloro-2'-(trifluoromethoxy)-[1,1'-biphenyl]-4-yl)piperidine-2-carboxamide (hereinafter referred to as the compound of Example 53) (0.0244 g, 0.0479 mmol, 38.2%) was obtained as a white solid.

¹H-NMR (400 MHz, CDCl₃) δ: 1.59-2.02(m, 5H), 2.29-2.32(m, 1H), 3.49-3.57(m, 1H), 3.73-3.77(m, 1H), 5.18-5.19 (m, 1H), 5.40(d, J=16.8 Hz, 1H), 5.48(d, J=16.8 Hz, 1H), 7.21-7.46(m, 6H), 7.81(br, 1H), 8.02(s, 1H), 8.86(s, 1H).

ESI-MS: m/z=509(M+H)⁺.

Example 54

Synthesis of 1-(2-(furan-2-yl)acetyl)-N-(2-chloro-2'-(trifluoromethoxy)-[1,1'-biphenyl]-4-yl)piperidine-2-carboxamide

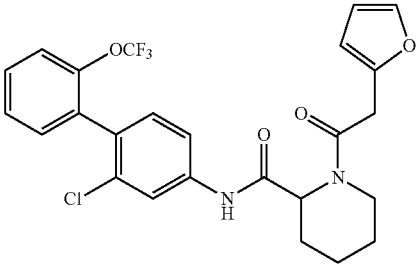 [SMILES: O=C(Nc1ccc(-c2ccccc2OC(F)(F)F)c(Cl)c1)C1CCCCN1C(=O)Cc1ccco1]

According to the same procedure as in Example 4, except that 2-furaneacetic acid was used in place of 2-methoxyacetic acid, 1-(2-(furan-2-yl)acetyl)-N-(2-chloro-2'-(trifluoromethoxy)-[1,1'-biphenyl]-4-yl)piperidine-2-carboxamide (hereinafter referred to as the compound of Example 54) (0.0605 g, 0.119 mmol, 95.2%) was obtained as a white amorphus.

¹H-NMR (400 MHz, CDCl₃) δ: 1.41-1.95(m, 5H), 2.33-2.38(m, 1H), 3.08-3.16(m, 1H), 3.85-3.97(m, 3H), 5.34-5.36 (m, 1H), 6.22-6.23(m, 1H), 6.35-6.37(m, 1H), 7.19-7.44(m, 8H), 8.33(br, 1H).

ESI-MS: m/z=505(M−H)⁻.

Example 55

Synthesis of 1-(2-(3,5-dimethyl-1H-pyrazol-1-yl)acetyl)-N-(2-chloro-2'-(trifluoromethoxy)-[1,1'-biphenyl]-4-yl)piperidine-2-carboxamide

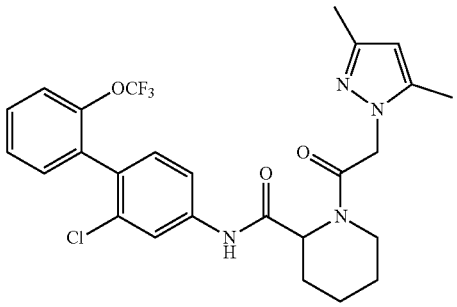 [SMILES: Cc1cc(C)n(CC(=O)N2CCCCC2C(=O)Nc2ccc(-c3ccccc3OC(F)(F)F)c(Cl)c2)n1]

According to the same procedure as in Example 4, except that 3,5-dimethyl-1H-pyrazole-1-acetic acid was used in place of 2-methoxyacetic acid, 1-(2-(3,5-dimethyl-1H-pyrazol-1-yl)acetyl)-N-(2-chloro-2'-(trifluoromethoxy)-[1,1'-biphenyl]-4-yl)piperidine-2-carboxamide (hereinafter referred to as the compound of Example 55) (0.0579 g, 0.108 mmol, 86.3%) was obtained as a white amorphus.

¹H-NMR (400 MHz, CDCl₃) δ: 1.46-1.66(m, 2H), 1.74-1.79(m, 3H), 2.08(s, 3H), 2.27(s, 3H), 2.47-2.50(m, 1H), 3.11-3.19(m, 1H), 3.69-3.74(m, 1H), 4.83(d, J=15.2 Hz, 1H), 4.96(d, J=15.2 Hz, 1H), 5.35-5.36(m, 1H), 5.89(s, 1H), 7.21-7.45(m, 7H), 8.86(br, 1H).

ESI-MS: m/z=535(M+H)⁺.

Example 56

Synthesis of 1-(2-(3-methylisoxazol-5-yl)acetyl)-N-(2-chloro-2'-(trifluoromethoxy)-[1,1'-biphenyl]-4-yl)piperidine-2-carboxamide

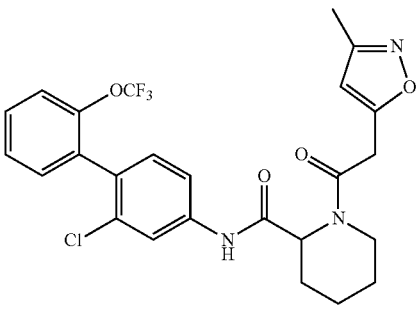 [SMILES: Cc1cc(CC(=O)N2CCCCC2C(=O)Nc2ccc(-c3ccccc3OC(F)(F)F)c(Cl)c2)on1]

According to the same procedure as in Example 4, except that 3-methyl-5-isoxazoleacetic acid was used in place of 2-methoxyacetic acid, 1-(2-(3-methylisoxazol-5-yl)acetyl)-N-(2-chloro-2'-(trifluoromethoxy)-[1,1'-biphenyl]-4-yl)piperidine-2-carboxamide (hereinafter referred to as the compound of Example 56) (0.0652 g, 0.125 mmol, 99.6%) was obtained as a white amorphus.

¹H-NMR (400 MHz, CDCl₃) δ: 1.47-1.96(m, 5H), 2.29(s, 3H), 2.33-2.39(m, 1H), 3.21-3.28(m, 1H), 3.82-3.87(m, 1H), 3.95(d, J=16.1 Hz, 1H), 4.01(d, J=16.1 Hz, 1H), 5.32-5.33 (m, 1H), 6.08(s, 1H), 7.21-7.45(m, 7H), 8.27(br, 1H).
ESI-MS: m/z=520(M−H)⁻.

Example 57

Synthesis of (R)-1-(2-(1H-tetrazol-1-yl)acetyl)-N-(2-chloro-2'-(trifluoromethoxy)-[1,1'-biphenyl]-4-yl)piperidine-2-carboxamide

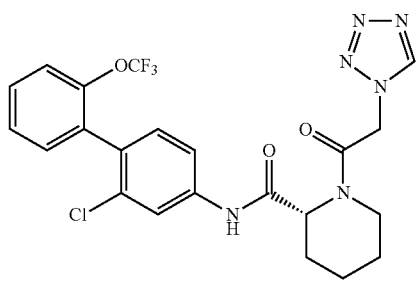

To a DMF (30 mL) solution of 1H-tetrazole-1-acetic acid (1.67 g, 13.04 mmol), a DMF (10 mL) solution of the compound of Reference Example 8 (4.00 g, 10.03 mmol), HATU (4.96 g, 13.04 mmol), and diisopropylethylamine (2.63 mL, 15.04 mmol) were added at room temperature, followed by stirring at the same temperature for 17 hours. To the reaction solution, distilled water was added, and the solution was extracted with toluene. The organic layer was concentrated under reduced pressure and the residue was purified by column chromatography (amine silica gel, n-hexane/ethyl acetate=40/60 to 0/100) to obtain (R)-1-(2-(1H-tetrazol-1-yl)acetyl)-N-(2-chloro-2'-(trifluoromethoxy)-[1,1'-biphenyl]-4-yl)piperidine-2-carboxamide (hereinafter referred to as the compound of Example 57) (3.87 g, 7.60 mmol, 75.9%) as a white amorphus. As a result of analysis using a chiral column, the retention time of the thus obtained compound of Example 57 was 55.3 minutes, and the optical purity at that time was 99.4% ee. The analysis conditions using the chiral column are as follows.

Measurement equipment; High-performance liquid chromatograph LC-2010CHT, manufactured by Shimadzu Corporation
Column; CHIRALCEL OD-RH 0.46 cmφ×15 cm, particle size of 5 μm, manufactured by Daicel Chemical Industries Ltd.
Column temperature; 40° C.
Mobile phase; (Solution A) Distilled water, (Solution B) acetonitrile
Composition of mobile phase; Solution A: Solution B=60:40 (0 to 75 minutes)
Flow rate; 0.5 mL/minute
Detection; UV (210 nm)

¹H-NMR (400 MHz, CDCl₃) δ: 1.62-2.00(m, 5H), 2.27-2.31(m, 1H), 3.52-3.58(m, 1H), 3.73-3.76(m, 1H), 5.18-5.19 (m, 1H), 5.40(d, J=16.5 Hz, 1H), 5.48(d, J=16.5 Hz, 1H), 7.21-7.45(m, 6H), 7.81(br, 1H), 8.15(s, 1H), 8.86(s, 1H).
ESI-MS: m/z=509(M+H)⁺.

Example 58

Synthesis of (R)-1-(3-(1H-tetrazol-1-yl)propanoyl)-N-(2-chloro-2'-(trifluoromethoxy)-[1,1'-biphenyl]-4-yl)piperidine-2-carboxamide

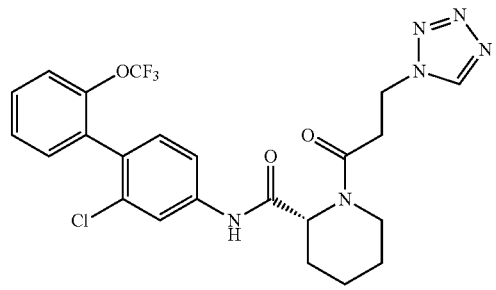 [SMILES: O=C(Nc1ccc(-c2ccccc2OC(F)(F)F)c(Cl)c1)[C@H]1CCCCN1C(=O)CCn1cnnn1]

According to the same procedure as in Example 4, except that 3-(tetrazol-1-yl)propionic acid was used in place of 2-methoxyacetic acid and the compound of Reference Example 8 was used in place of the compound of Reference Example 3, (R)-1-(3-(1H-tetrazol-1-yl)propanoyl)-N-(2-chloro-2'-(trifluoromethoxy)-[1,1'-biphenyl]-4-yl)piperidine-2-carboxamide (hereinafter referred to as the compound of Example 58) (0.117 g, 0.224 mmol, 89.1%) was obtained as a white amorphus.

¹H-NMR (400 MHz, CDCl₃) δ: 1.43-1.97(m, 5H), 2.25-2.29(m, 1H), 3.04-3.19(m, 2H), 3.25(td, J=13.0, 2.7 Hz, 1H), 3.70-3.74(m, 1H), 4.79-4.92(m, 2H), 5.18-5.19(m, 1H), 7.22-7.44(m, 6H), 7.79(br, 1H), 8.13(br, 1H), 8.84(s, 1H).
ESI-MS: m/z=521(M−H)⁻.

Example 59

Synthesis of (R)-1-(3-(1H-imidazol-1-yl)propanoyl)-N-(2-chloro-2'-(trifluoromethoxy)-[1,1'-biphenyl]-4-yl)piperidine-2-carboxamide

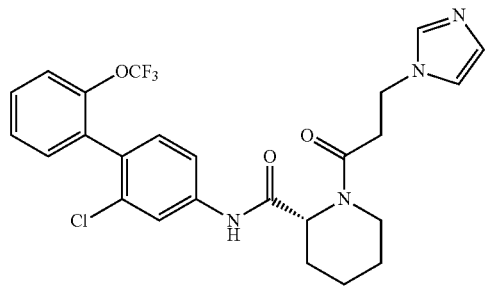 [SMILES: O=C(Nc1ccc(-c2ccccc2OC(F)(F)F)c(Cl)c1)[C@H]1CCCCN1C(=O)CCn1ccnc1]

According to the same procedure as in Example 4, except that 3-(imidazol-1-yl)propionic acid was used in place of 2-methoxyacetic acid and the compound of Reference Example 8 was used in place of the compound of Reference Example 3, (R)-1-(3-(1H-imidazol-1-yl)propanoyl)-N-(2-chloro-2'-(trifluoromethoxy)-[1,1'-biphenyl]-4-yl)piperidine-2-carboxamide (hereinafter referred to as the compound of Example 59) (0.0796 g, 0.153 mmol, 60.9%) was obtained as a white amorphus.

$^1$H-NMR (400 MHz, CDCl$_3$) δ: 1.37-1.99(m, 5H), 2.26-2.29(m, 1H), 2.87-2.91(m, 2H), 3.17(td, J=13.3, 2.7 Hz, 1H), 3.67-3.71(m, 1H), 4.34-4.47(m, 2H), 5.24-5.25(m, 1H), 6.99(s, 1H), 7.06(s, 1H), 7.21-7.45(m, 6H), 7.58(br, 1H), 7.71-7.82(m, 1H), 8.33(br, 1H).

ESI-MS: m/z=521(M+H)$^+$.

Example 60

Synthesis of (R)-1-(3-(3-methyl-1H-pyrazol-1-yl)propanoyl)-N-(2-chloro-2'-(trifluoromethoxy)-[1,1'-biphenyl]-4-yl)piperidine-2-carboxamide

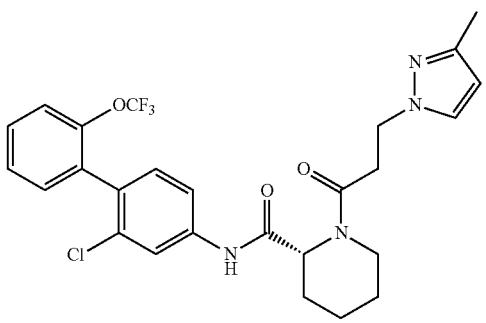 [SMILES: Cc1ccn(CCC(=O)N2CCCC[C@@H]2C(=O)Nc2ccc(-c3ccccc3OC(F)(F)F)c(Cl)c2)n1]

According to the same procedure as in Example 4, except that 3-(3-methyl-pyrazol-1-yl)propionic acid was used in place of 2-methoxyacetic acid and the compound of Reference Example 8 was used in place of the compound of Reference Example 3, (R)-1-(3-(3-methyl-1H-pyrazol-1-yl)propanoyl)-N-(2-chloro-2'-(trifluoromethoxy)-[1,1'-biphenyl]-4-yl)piperidine-2-carboxamide (hereinafter referred to as the compound of Example 60) (0.135 g, 0.252 mmol, quantitative) was obtained as a white amorphus.

$^1$H-NMR (400 MHz, CDCl$_3$) δ: 1.37-1.89(m, 5H), 2.12(s, 3H), 2.35-2.38(m, 1H), 2.85-3.12(m, 3H), 3.67-3.70(m, 1H), 4.38-4.44(m, 1H), 4.51-4.58(m, 1H), 5.30-5.32(m, 1H), 5.96-5.97(m, 1H), 7.19-7.45(m, 8H), 8.59(br, 1H).

ESI-MS: m/z=535(M+H)$^+$.

Example 61

Synthesis of (R)-1-(2-(1H-pyrazol-1-yl)acetyl)-N-(2-chloro-2'-(trifluoromethoxy)-[1,1'-biphenyl]-4-yl)piperidine-2-carboxamide

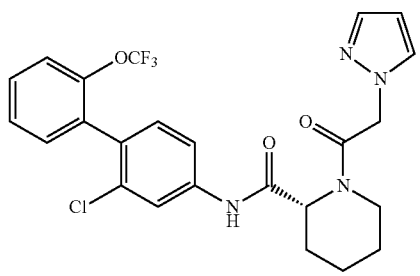 [SMILES: O=C(Nc1ccc(-c2ccccc2OC(F)(F)F)c(Cl)c1)[C@H]1CCCCN1C(=O)Cn1cccn1]

According to the same procedure as in Example 4, except that 2-(1H-pyrazol-1-yl)acetic acid was used in place of 2-methoxyacetic acid and the compound of Reference Example 8 was used in place of the compound of Reference Example 3, (R)-1-(2-(1H-pyrazol-1-yl)acetyl)-N-(2-chloro-2'-(trifluoromethoxy)-[1,1'-biphenyl]-4-yl)piperidine-2-carboxamide (hereinafter referred to as the compound of Example 61) (0.0623 g, 0.123 mmol, 98.0%) was obtained as a white solid.

$^1$H-NMR (400 MHz, CDCl$_3$) δ: 1.46-1.74(m, 5H), 2.52-2.55(m, 1H), 3.04-3.12(m, 1H), 3.65-3.69(m, 1H), 5.01(d, J=14.5 Hz, 1H), 5.22(d, J=14.5 Hz, 1H), 5.43-5.44(m, 1H), 6.39(dd, J=2.3, 2.0 Hz, 1H), 7.24(d, J=8.2 Hz, 1H), 7.32-7.37(m, 3H), 7.41-7.45(m, 1H), 7.52-7.61(m, 1H), 7.53(d, J=2.3 Hz, 1H), 7.58(d, J=2.0 Hz, 1H), 7.80-7.87(brm, 1H), 9.02(s, 1H).

ESI-MS: m/z=507(M+H)$^+$.

Example 62

Synthesis of (R)-1-(2-(4H-1,2,4-triazol-4-yl)acetyl)-N-(2-chloro-2'-(trifluoromethoxy)-[1,1'-biphenyl]-4-yl)piperidine-2-carboxamide

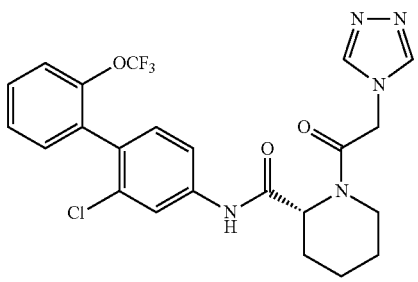

According to the same procedure as in Example 4, except that 2-(4H-1,2,4-triazol-4-yl)acetic acid was used in place of 2-methoxyacetic acid and the compound of Reference Example 8 was used in place of the compound of Reference Example 3, (R)-1-(2-(4H-1,2,4-triazol-4-yl)acetyl)-N-(2-chloro-2'-(trifluoromethoxy)-[1,1'-biphenyl]-4-yl)piperidine-2-carboxamide (hereinafter referred to as the compound of Example 62) (0.0575 g, 0.113 mmol, 90.3%) was obtained as a white solid.

$^1$H-NMR (400 MHz, CDCl$_3$) δ: 1.55-1.90(m, 5H), 2.29-2.32(m, 1H), 3.57-3.71(m, 2H), 4.93(d, J=16.8 Hz, 1H), 5.02(d, J=16.8 Hz, 1H), 5.22-5.23(m, 1H), 7.19(d, J=8.2 Hz, 1H), 7.28-7.37(m, 4H), 7.40-7.45(m, 1H), 7.81(s, 1H), 8.21 (s, 2H), 8.84(s, 1H).

ESI-MS: m/z=508(M+H)$^+$.

Example 63

Synthesis of (R)-1-(2-(1H-1,2,4-triazol-1-yl)acetyl)-N-(2-chloro-2'-(trifluoromethoxy)-[1,1'-biphenyl]-4-yl)piperidine-2-carboxamide

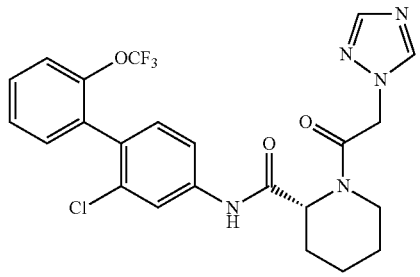 [SMILES: O=C(Nc1ccc(-c2ccccc2OC(F)(F)F)c(Cl)c1)[C@H]1CCCCN1C(=O)Cn1cncn1]

According to the same procedure as in Example 4, except that sodium 2-(1H-1,2,4-triazol-1-yl)acetate was used in place of 2-methoxyacetic acid and the compound of Reference Example 8 was used in place of the compound of Reference Example 3, (R)-1-(2-(1H-1,2,4-triazol-1-yl)acetyl)-N-(2-chloro-2'-(trifluoromethoxy)-[1,1'-biphenyl]-4-yl)piperidine-2-carboxamide (hereinafter referred to as the compound of Example 63) (0.0587 g, 0.116 mmol, 92.2%) was obtained as a white solid.

$^1$H-NMR (400 MHz, CDCl$_3$) δ: 1.54-1.70(m, 2H), 1.77-1.90(m, 3H), 2.38-2.41(m, 1H), 3.31-3.39(m, 1H), 3.74-3.78(m, 1H), 5.13(d, J=15.4 Hz, 1H), 5.22(d, J=15.4 Hz, 1H), 5.29(d, J=5.0 Hz, 1H), 7.23(d, J=8.2 Hz, 1H), 7.30-7.37(m, 4H), 7.41-7.45(m, 1H), 7.79(brs, 1H), 8.02(s, 1H), 8.26(s, 1H), 8.39(s, 1H).
ESI-MS: m/z=508(M+H)$^+$.

Example 64

Synthesis of (R)-1-(2-(1H-1,2,3-triazol-1-yl)acetyl)-N-(2-chloro-2'-(trifluoromethoxy)-[1,1'-biphenyl]-4-yl)piperidine-2-carboxamide

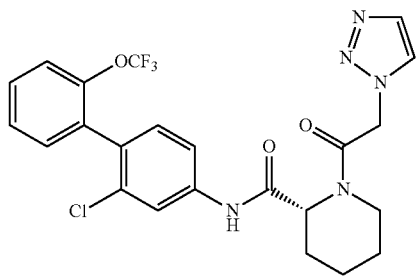

According to the same procedure as in Example 4, except that 2-(1H-1,2,3-triazol-1-yl)acetic acid was used in place of 2-methoxyacetic acid and the compound of Reference Example 8 was used in place of the compound of Reference Example 3, (R)-1-(2-(1H-1,2,3-triazol-1-yl)acetyl)-N-(2-chloro-2'-(trifluoromethoxy)-[1,1'-biphenyl]-4-yl)piperidine-2-carboxamide (hereinafter referred to as the compound of Example 64) (0.0619 g, 0.122 mmol, 97.2%) was obtained as a white solid.

$^1$H-NMR (400 MHz, CDCl$_3$) δ: 1.51-1.70(m, 2H), 1.76-1.88(m, 3H), 2.39-2.42(m, 1H), 3.32-3.39(m, 1H), 3.74-3.78(m, 1H), 5.30-5.31(m, 1H), 5.34(d, J=15.4 Hz, 1H), 5.41(d, J=15.4 Hz, 1H), 7.23(d, J=8.6 Hz, 1H), 7.30-7.37(m, 3H), 7.41-7.45(m, 1H), 7.52(brs, 1H), 7.76(d, J=0.9 Hz, 1H), 7.82(d, J=0.9 Hz, 1H), 7.91(brs, 1H), 8.43(s, 1H).
ESI-MS: m/z=508(M+H)$^+$.

Example 65

Synthesis of (R)-1-(2-(1H-imidazol-1-yl)acetyl)-N-(2-chloro-2'-(trifluoromethoxy)-[1,1'-biphenyl]-4-yl)piperidine-2-carboxamide

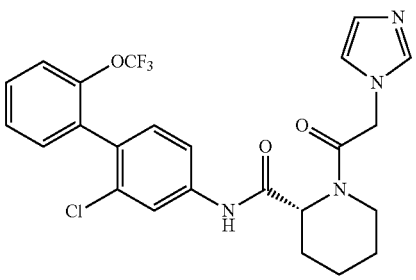 [SMILES: O=C(Nc1ccc(-c2ccccc2OC(F)(F)F)c(Cl)c1)[C@H]1CCCCN1C(=O)Cn1ccnc1]

According to the same procedure as in Example 4, except that 1-imidazoleacetic acid was used in place of 2-methoxyacetic acid and the compound of Reference Example 8 was used in place of the compound of Reference Example 3, (R)-1-(2-(1H-imidazol-1-yl)acetyl)-N-(2-chloro-2'-(trifluoromethoxy)-[1,1'-biphenyl]-4-yl)piperidine-2-carboxamide (hereinafter referred to as the compound of Example 65) (0.635 g, 1.25 mmol, 63.5%) was obtained as a white amorphus.

$^1$H-NMR (400 MHz, CDCl$_3$) δ: 1.44-2.05(m, 5H), 2.23-2.31(m, 1H), 3.37-3.47(m, 1H), 3.67-3.74(m, 1H), 4.86(d, J=16.6 Hz, 1H), 4.91(d, J=16.6 Hz, 1H), 5.16-5.22(m, 1H), 6.97(s, 1H), 7.13(s, 1H), 7.20(d, J=8.3 Hz, 1H), 7.29-7.37(m, 4H), 7.40-7.45(m, 1H), 7.53(s, 1H), 7.70-7.87(m, 1H), 8.41(brs, 1H).
ESI-MS: m/z=507(M+H)$^+$.

Example 66

Synthesis of (R)-1-(2-(2H-1,2,3-triazol-2-yl)acetyl)-N-(2-chloro-2'-(trifluoromethoxy)-[1,1'-biphenyl]-4-yl)piperidine-2-carboxamide

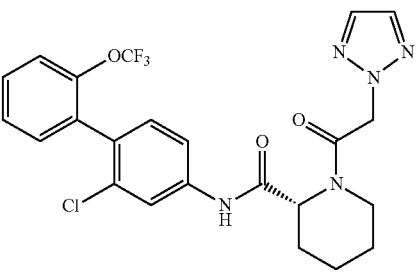 [SMILES: O=C(Nc1ccc(-c2ccccc2OC(F)(F)F)c(Cl)c1)[C@H]1CCCCN1C(=O)Cn1nccn1]

According to the same procedure as in Example 4, except that 2-(2H-1,2,3-triazol-2-yl)acetic acid was used in place of 2-methoxyacetic acid and the compound of Reference Example 8 was used in place of the compound of Reference Example 3, (R)-1-(2-(2H-1,2,3-triazol-2-yl)acetyl)-N-(2-chloro-2'-(trifluoromethoxy)-[1,1'-biphenyl]-4-yl)piperidine-2-carboxamide (hereinafter referred to as the compound of Example 66) (0.0321 g, 0.0632 mmol, 50.4%) was obtained as a white amorphus.

¹H-NMR (400 MHz, CDCl₃) δ: 1.47-1.65(m, 2H), 1.68-1.77(m, 3H), 2.49-2.52(m, 1H), 2.98-3.06(m, 1H), 3.55-3.58 (m, 1H), 5.33(d, J=15.0 Hz, 1H), 5.42(d, J=5.0 Hz, 1H), 5.57(d, J=15.0 Hz, 1H), 7.24(d, J=8.2 Hz, 1H), 7.32-7.37(m, 3H), 7.41-7.46(m, 1H), 7.42-7.88(brm, 2H), 7.73(s, 2H), 8.63(s, 1H).

ESI-MS: m/z=530(M+Na)⁺.

Reference Example 30

Synthesis of ethyl 2-(5-methyl-1,3,4-oxadiazol-2-yl)acetate

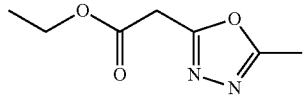

To a dichloroethane (6.4 mL) solution of ethyl 2-(1H-tetrazol-5-yl)acetate (0.500 g, 3.20 mmol), acetic anhydride (0.393 mL, 4.16 mmol) was added at room temperature and the temperature was raised to 100° C., followed by stirring for 11 hours. To the reaction solution, an aqueous 1M sodium hydroxide solution was added, and the solution was extracted with ethyl acetate. The organic layer was washed with an aqueous 1M sodium hydroxide solution and saturated brine, dried over anhydrous sodium sulfate and filtered, and then the filtrate was concentrated under reduced pressure. The residue was purified by column chromatography (silica gel, n-hexane/ethyl acetate=70/30 to 40/60) to obtain ethyl 2-(5-methyl-1,3,4-oxadiazol-2-yl)acetate (hereinafter referred to as the compound of Reference Example 30) (0.0908 g, 0.534 mmol, 16.7%) as a colorless oily product.

¹H-NMR (400 MHz, CDCl₃) δ: 1.29(t, J=7.2 Hz, 3H), 2.55(s, 3H), 3.92(s, 2H), 4.23(q, J=7.2 Hz, 2H).

ESI-MS: m/z=171(M+H)⁺.

Reference Example 31

Synthesis of sodium 2-(5-methyl-1,3,4-oxadiazol-2-yl)acetate

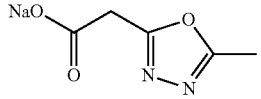

To a tetrahydrofuran (1.0 mL) solution of the compound of Reference Example 30 (0.0900 g, 0.529 mmol), an aqueous 1M sodium hydroxide solution (1.06 mL, 1.06 mmol) and ethanol (1.0 mL) were added at room temperature, followed by stirring at the same temperature for 2 hours. The reaction solution was concentrated under reduced pressure to obtain crude sodium 2-(5-methyl-1,3,4-oxadiazol-2-yl)acetate (hereinafter referred to as the compound of Reference Example 31) (0.0835 g) as a white solid. The compound of Reference Example 31 was directly used for the subsequent reaction.

¹H-NMR (400 MHz, DMSO-D₆) δ: 2.41(s, 3H), 3.38(s, 2H).

ESI-MS: m/z=143(M+H)⁺.

Example 67

Synthesis of (R)-N-(2-chloro-2'-(trifluoromethoxy)-[1,1'-biphenyl]-4-yl)-1-(2-(5-methyl-1,3,4-oxadiazol-2-yl)acetyl)piperidine-2-carboxamide

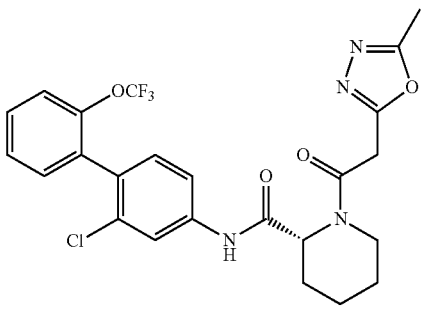 [SMILES: Cc1nnc(CC(=O)N2CCCC[C@@H]2C(=O)Nc2ccc(-c3ccccc3OC(F)(F)F)c(Cl)c2)o1]

According to the same procedure as in Example 4, except that the compound of Reference Example 31 was used in place of 2-methoxyacetic acid and the compound of Reference Example 8 was used in place of the compound of Reference Example 3, (R)-N-(2-chloro-2'-(trifluoromethoxy)-[1,1'-biphenyl]-4-yl)-1-(2-(5-methyl-1,3,4-oxadiazol-2-yl)acetyl)piperidine-2-carboxamide (hereinafter referred to as the compound of Example 67) (0.0524 g, 0.0910 mmol, 90.8%) was obtained as a white amorphus.

¹H-NMR (400 MHz, CDCl₃) δ: 1.50-1.66(m, 3H), 1.74-1.77(m, 2H), 2.57(s, 3H), 2.62-2.65(m, 1H), 3.27-3.34(m, 1H), 3.61-3.64(m, 1H), 3.94(d, J=17.4 Hz, 1H), 4.21(d, J=17.4 Hz, 1H), 5.54-5.55(m, 1H), 7.25-7.27(m, 1H), 7.33-7.36(m, 3H), 7.40-7.44(m, 1H), 7.77(brs, 1H), 8.18(brs, 1H), 9.38(s, 1H).

ESI-MS: m/z=545(M+Na)⁺.

Example 68

Synthesis of (R)-N-(2-chloro-2'-(trifluoromethoxy)-[1,1'-biphenyl]-4-yl)-1-(3-(dimethylamino)propanoyl)piperidine-2-carboxamide

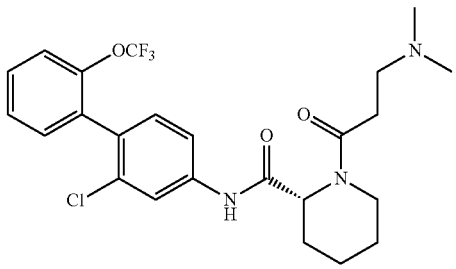

According to the same procedure as in Example 4, except that 3-(dimethylamino)propanoic acid hydrochloride was used in place of 2-methoxyacetic acid and the compound of Reference Example 8 was used in place of the compound of Reference Example 3, (R)-N-(2-chloro-2'-(trifluoromethoxy)-[1,1'-biphenyl]-4-yl)-1-(3-(dimethylamino)propanoyl)piperidine-2-carboxamide (hereinafter referred to as the compound of Example 68) (0.0826 g, 0.166 mmol, 66.2%) was obtained as a white amorphus.

$^1$H-NMR (400 MHz, CDCl$_3$) δ: 1.46-1.83(m, 5H), 2.26(s, 0.6H), 2.28(s, 5.4H), 2.40-2.44(m, 1H), 2.55-2.62(m, 1H), 2.65-2.81(m, 3H), 2.99-3.05(m, 0.1H), 3.13-3.20(m, 0.9H), 3.88-3.91(m, 0.9H), 4.69(d, J=5.0 Hz, 0.1H), 4.73-4.76(m, 0.1H), 5.43(d, J=5.0 Hz, 0.9H), 7.21(d, J=8.6 Hz, 1H), 7.31-7.86(m, 6H), 8.76(br, 0.9H), 9.33(br, 0.1H).
ESI-MS: m/z=498(M+H)$^+$.

Example 69

Synthesis of methyl (R)-5-(2-((2-chloro-2'-(trifluoromethoxy)-[1,1'-biphenyl]-4-yl)carbamoyl)piperidin-1-yl)-5-oxopentanoate

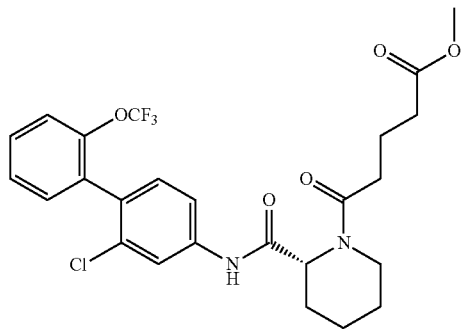 [SMILES: COC(=O)CCCC(=O)N1CCCC[C@@H]1C(=O)Nc1ccc(-c2ccccc2OC(F)(F)F)c(Cl)c1]

According to the same procedure as in Example 3, except that methyl 4-(chloroformyl)butyrate was used in place of propionyl chloride and the compound of Reference Example 8 was used in place of the compound of Reference Example 3, methyl (R)-5-(2-((2-chloro-2'-(trifluoromethoxy)-[1,1'-biphenyl]-4-yl)carbamoyl)piperidin-1-yl)-5-oxopentanoate (hereinafter referred to as the compound of Example 69) (0.130 g, 0.247 mmol, 98.4%) was obtained as a white amorphus.

$^1$H-NMR (400 MHz, CDCl$_3$) δ: 1.44-1.79(m, 4H), 1.84-1.95(m, 1H), 1.96-2.13(m, 2H), 2.35(d, J=13.7 Hz, 1H), 2.40-2.62(m, 4H), 2.63-2.70(m, 0.1H), 3.14-3.21(m, 0.9H), 3.68(s, 2.7H), 3.69(s, 0.3H), 3.84-3.88(m, 0.9H), 4.66-4.69(m, 0.2H), 5.34(d, J=5.0 Hz, 0.9H), 7.20(d, J=8.2 Hz, 1H), 7.29-7.94(m, 6H), 8.68(s, 0.9H), 8.90(s, 0.1H).

Example 70

Synthesis of (R)-5-(2-((2-chloro-2'-(trifluoromethoxy)-[1,1'-biphenyl]-4-yl)carbamoyl)piperidin-1-yl)-5-oxopentanoic Acid

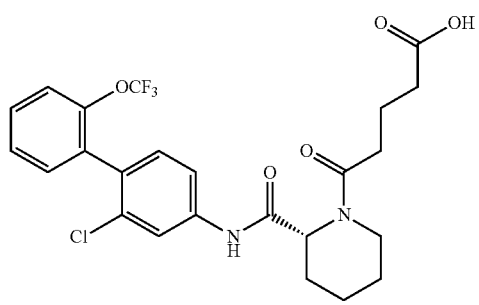 [SMILES: O=C(O)CCCC(=O)N1CCCC[C@@H]1C(=O)Nc1ccc(-c2ccccc2OC(F)(F)F)c(Cl)c1]

To a methanol (2.5 mL) solution of the compound of Example 69 (0.130 g, 0.247 mmol), an aqueous 1M sodium hydroxide solution (2.47 mL, 2.47 mmol) and tetrahydrofuran (2.5 mL) were added at 0° C. and the temperature was raised to room temperature, followed by stirring for 5 hours. To the reaction solution, 1M hydrochloric acid was added, and the solution was extracted with chloroform. The organic layer was washed with saturated brine, dried over anhydrous sodium sulfate and filtered, and then the filtrate was concentrated under reduced pressure. The residue was purified by column chromatography (silica gel, chloroform/methanol=98/2 to 90/10) to obtain (R)-5-(2-((2-chloro-2'-(trifluoromethoxy)-[1,1'-biphenyl]-4-yl)carbamoyl)piperidin-1-yl)-5-oxopentanoic acid (hereinafter referred to as the compound of Example 70) (0.0592 g, 0.115 mmol, 46.7%) as a white amorphus.

$^1$H-NMR (400 MHz, CDCl$_3$) δ: 1.49-1.79(m, 4H), 1.84-1.94(m, 1H), 2.00-2.10(m, 2H), 2.32(d, J=13.6 Hz, 1H), 2.44-2.63(m, 4H), 3.20(td, J=13.3, 2.6 Hz, 1H), 3.81-3.87(m, 1H), 5.30(d, J=4.5 Hz, 1H), 7.20(d, J=8.6 Hz, 1H), 7.29-7.36(m, 3H), 7.40-7.45(m, 2H), 7.75-7.88(m, 1H), 8.62(s, 1H).
ESI-MS: m/z=535(M+Na)$^+$.

Example 71

Inhibitory Effect on RORγ-Coactivator Binding

The inhibitory effect of the cyclic amine derivative (I) or a pharmacologically acceptable salt thereof on the binding between a ligand-binding domain of RORγ (hereinafter referred to as RORγ-LBD) and a coactivator was evaluated using Invitrogen's LanthaScreen™ TR-FRET Retinoid-Related Orphan Receptor (ROR) gamma Coactivator Assay kit utilizing time-resolved fluorescence energy transfer (TR-FRET).

The test compound was dissolved in DMSO and diluted with TR-FRET Coregulator Buffer D (Invitrogen) containing 5 mmol/L of DTT to have a final DMSO concentration of 1% before use. To each well of a 384-well black plate (Corning Inc.), 4 nmol/L of GST-fused RORγ-LBD (Invitrogen) diluted with the buffer mentioned above and the test compound were added. A well without addition of the test compound and without addition of GST-fused RORγ-LBD (background) and a well without addition of the test compound and with addition of GST-fused RORγ-LBD (control)

were prepared. Next, 150 nmol/L of fluorescein-labeled TRAP220/DRIP-2 (Invitrogen) diluted with the buffer mentioned above and 32 nmol/L of terbium-labeled anti-GST antibody (Invitrogen) were added to each well. After incubating the plate at room temperature for 16 to 24 hours, the fluorescence at 495 nm and 520 nm when excited at 320 nm was measured for each well and the ratio (fluorescence value at 520 nm/fluorescence value at 495 nm) was calculated.

The fold change with addition of the test compound (ratio with addition of the test compound/ratio of the background), the fold change of the control (ratio of the control/ratio of the background), and the fold change of the background (ratio of the background/ratio of the background) were calculated, and then the inhibition rate of binding between RORγ-LBD and a coactivator (hereinafter referred to as RORγ-coactivator binding inhibition rate) (%) was calculated from Formula 1:

RORγ-coactivator binding inhibition rate(%)=(1−((Fold change with addition of the test compound)−(Fold change of the background))/((Fold change of the control)−(Fold change of the background)))×100   Formula 1

The RORγ-coactivator binding inhibition rate (%) at 33 μmol/L of the test compound is shown in Tables 2-1 and 2-2.

TABLE 2-1

| Test compound | RORγ-coactivator binding inhibition rate (%) |
|---|---|
| Compound of Example 1 | 90.9 |
| Compound of Example 2 | 91.9 |
| Compound of Example 3 | 88.2 |
| Compound of Example 4 | 90.3 |
| Compound of Example 5 | 96.9 |
| Compound of Example 8 | 95.2 |
| Compound of Example 10 | 100.1 |
| Compound of Example 13 | 101.4 |
| Compound of Example 14 | 94.0 |
| Compound of Example 15 | 100.1 |
| Compound of Example 16 | 99.3 |
| Compound of Example 17 | 93.8 |
| Compound of Example 18 | 95.9 |
| Compound of Example 19 | 93.4 |
| Compound of Example 20 | 100.7 |
| Compound of Example 21 | 98.2 |
| Compound of Example 22 | 92.4 |
| Compound of Example 23 | 98.4 |
| Compound of Example 25 | 94.2 |
| Compound of Example 28 | 100.9 |
| Compound of Example 29 | 101.3 |
| Compound of Example 32 | 94.7 |
| Compound of Example 36 | 97.2 |
| Compound of Example 37 | 103.5 |
| Compound of Example 39 | 98.8 |
| Compound of Example 40 | 98.7 |
| Compound of Example 42 | 92.8 |
| Compound of Example 43 | 99.0 |
| Compound of Example 44 | 97.1 |
| Compound of Example 45 | 92.0 |
| Compound of Example 46 | 99.3 |
| Compound of Example 47 | 98.8 |
| Compound of Example 48 | 101.6 |
| Compound of Example 49 | 99.3 |
| Compound of Example 50 | 101.1 |
| Compound of Example 51 | 100.4 |
| Compound of Example 52 | 97.3 |
| Compound of Example 53 | 104.7 |
| Compound of Example 54 | 101.5 |
| Compound of Example 55 | 103.5 |
| Compound of Example 56 | 103.5 |
| Compound of Example 57 | 103.0 |
| Compound of Example 58 | 100.5 |

TABLE 2-2

| Test compound | RORγ-coactivator binding inhibition rate (%) |
|---|---|
| Compound of Example 59 | 95.5 |
| Compound of Example 60 | 93.6 |
| Compound of Example 61 | 101.9 |
| Compound of Example 64 | 97.3 |
| Compound of Example 65 | 91.7 |
| Compound of Example 66 | 103.2 |
| Compound of Example 67 | 99.1 |
| Compound of Example 69 | 95.9 |

These results revealed that the cyclic amine derivative (I) or a pharmacologically acceptable salt thereof markedly inhibits the binding between RORγ-LBD and a coactivator.

Example 72

Suppressive Effect on IL-17 Production in Mouse Splenocytes

Using mouse splenocytes, the suppressive effect of the cyclic amine derivative (I) or a pharmacologically acceptable salt thereof on IL-17 production by IL-23 stimulation was evaluated by a partially modified method mentioned in The Journal of Biological Chemistry, 2003, Vol. 278, No. 3, p. 1910-1914.

A single cell suspension was prepared from the spleen of C57BL/6J mice (male, 7 to 23 weeks old) (Charles River Laboratories Japan, Inc.) and splenocytes were prepared using Histopaque-1083 (Sigma-Aldrich Japan). The culture medium was used by adding 10% FBS (Gibco), 50 U/mL of penicillin 50 μg/mL of streptomycin (Gibco), 50 μmol/L of 2-mercaptoethanol (Gibco), and 100 U/mL of human IL-2 (Cell Science & Technology Institute, Inc.) to RPMI1640 medium (Gibco). The test compound was dissolved in DMSO and then diluted with the culture medium to have a final concentration of DMSO of 0.1% before use. Splenocytes ($3 \times 10^5$ cells/well) prepared in the culture medium were seeded in wells of a 96-well flat-bottom plate (Corning Incorporated), the test compound and 10 ng/mL of human IL-23 (R & D systems, Inc.) were added thereto, and the cells were cultured at 37° C. under 5% $CO_2$ for 3 days. A well without addition of human IL-23 and without addition of the test compound and a well with addition of human IL-23 and without addition of the test compound were prepared. After completion of the culture, the culture supernatant was collected and the IL-17 production amount in the supernatant was determined by ELISA method (R & D systems, Inc.).

The IL-17 production inhibition rate (%) was calculated from Formula 2.

IL-17 production inhibition rate(%)=(1−((IL-17 production amount with addition of IL-23 and with addition of the test compound)−(IL-17 production amount without addition of IL-23 and without addition of the test compound))/((IL-17 production amount with addition of IL-23 and without addition of the test compound)−(IL-17 production amount without addition of IL-23 and without addition of the test compound)))×100   Formula 2

The IL-17 production inhibition rate (%) at 5 μmol/L of the test compound is shown in Tables 3-1 and 3-2.

TABLE 3-1

| Test compound | IL-17 production inhibition rate (%) |
|---|---|
| Compound of Example 1 | 94.0 |
| Compound of Example 2 | 96.2 |
| Compound of Example 3 | 98.6 |
| Compound of Example 4 | 99.7 |
| Compound of Example 5 | 99.5 |
| Compound of Example 6 | 91.6 |
| Compound of Example 7 | 99.0 |
| Compound of Example 8 | 99.2 |
| Compound of Example 9 | 94.6 |
| Compound of Example 10 | 98.6 |
| Compound of Example 11 | 94.1 |
| Compound of Example 12 | 96.1 |
| Compound of Example 13 | 98.2 |
| Compound of Example 14 | 90.5 |
| Compound of Example 15 | 99.4 |
| Compound of Example 16 | 98.0 |
| Compound of Example 17 | 91.8 |
| Compound of Example 18 | 90.8 |
| Compound of Example 19 | 99.8 |
| Compound of Example 20 | 99.7 |
| Compound of Example 21 | 99.8 |
| Compound of Example 22 | 98.1 |
| Compound of Example 23 | 99.4 |
| Compound of Example 24 | 95.7 |
| Compound of Example 25 | 99.4 |
| Compound of Example 26 | 96.4 |
| Compound of Example 27 | 97.4 |
| Compound of Example 28 | 98.6 |
| Compound of Example 29 | 100.1 |
| Compound of Example 30 | 99.8 |
| Compound of Example 31 | 99.1 |
| Compound of Example 32 | 98.8 |
| Compound of Example 33 | 98.3 |
| Compound of Example 34 | 100.3 |
| Compound of Example 35 | 94.9 |
| Compound of Example 36 | 96.9 |
| Compound of Example 37 | 99.1 |
| Compound of Example 38 | 99.0 |
| Compound of Example 39 | 99.2 |
| Compound of Example 40 | 98.2 |
| Compound of Example 41 | 99.1 |
| Compound of Example 42 | 99.8 |
| Compound of Example 43 | 92.4 |

TABLE 3-2

| Test compound | IL-17 production inhibition rate (%) |
|---|---|
| Compound of Example 44 | 91.5 |
| Compound of Example 45 | 99.9 |
| Compound of Example 46 | 99.2 |
| Compound of Example 47 | 96.3 |
| Compound of Example 48 | 99.4 |
| Compound of Example 49 | 98.3 |
| Compound of Example 50 | 94.5 |
| Compound of Example 51 | 98.6 |
| Compound of Example 52 | 99.3 |
| Compound of Example 53 | 101.6 |
| Compound of Example 54 | 98.7 |
| Compound of Example 55 | 99.7 |
| Compound of Example 56 | 107.4 |
| Compound of Example 57 | 101.2 |
| Compound of Example 58 | 99.7 |
| Compound of Example 59 | 99.8 |
| Compound of Example 60 | 99.7 |
| Compound of Example 61 | 98.8 |
| Compound of Example 62 | 100.2 |
| Compound of Example 63 | 99.9 |
| Compound of Example 64 | 99.4 |
| Compound of Example 65 | 99.6 |
| Compound of Example 66 | 99.5 |
| Compound of Example 67 | 98.7 |
| Compound of Example 68 | 99.4 |
| Compound of Example 69 | 99.5 |
| Compound of Example 70 | 99.7 |

These results revealed that the cyclic amine derivative (I) or a pharmacologically acceptable salt thereof suppresses IL-17 production.

Example 73

Symptom Suppressive Effect on Mouse Experimental Autoimmune Encephalomyelitis Model Using increase in the neurological symptom score as an index of exacerbation of symptoms, the effect of the cyclic amine derivative (I) or a pharmacologically acceptable salt thereof in a mouse experimental autoimmune encephalomyelitis model was evaluated. The mouse experimental autoimmune encephalomyelitis model was prepared by a partially modified method by Hindinger et al. (Journal of Neuroscience Research, 2006, Vol. 84, p. 1225-1234).

A total of 0.1 mL (0.05 mL on each side) of an MOG35-55 administration solution prepared by mixing a PBS solution containing partial synthetic peptides of myelin oligodendrocyte glycoproteins (MOG35-55; CSBio, Inc.) prepared to a concentration of 4 mg/mL with Freund's complete adjuvant at equal amount was intradermally inoculated to both flank sides of C57BL/6J mice (male, 8 weeks old) (Charles River Laboratories Japan, Inc.). Furthermore, 200 µL of pertussis toxin (Sigma-Aldrich Japan) prepared to a concentration of 1 µg/mL was intraperitoneally administered to the mice on the day of inoculation and 2 days after inoculation of the MOG35-55 administration solution.

After inoculation of the MOG35-55 administration solution, the test compound was administered to the mice. As the test compound, the compound of Example 20, the compound of Example 29, and the compound of Example 57 were used. The compound of Example 20 was suspended in a 0.5 w/v % methylcellulose solution and orally administered once daily at a dose of 3 mg/kg every day from 2 days after inoculation of the MOG35-55 administration solution. The compound of Example 29 and the compound of Example 57 were suspended in a 0.5 w/v % methylcellulose solution and orally administered once daily at a dose of 1 mg/kg every day from 13 days after inoculation of the MOG35-55 administration solution. The group in which the compound of Example 20 was administered to mice was defined as the Example-20 compound administration group, the group in which the compound of Example 29 was administered was defined as the Example-29 compound administration group, and the group in which the compound of Example 57 was administered was defined as the Example-57 compound administration group. In the vehicle administration group, a vehicle of each test compound (0.5 w/v % methylcellulose solution) was similarly administered.

After inoculation of the MOG35-55 administration solution, the neurological symptom scores in the groups in which test compound was administered and the corresponding vehicle administration groups were scored (0: normal, 1: limp tail or hind limb weakness, 2: limp tail and hind limb weakness, 3: partial hind limb paralysis, 4: complete hind limb paralysis, 5: moribund state). As the scoring method, the method mentioned in Current Protocols in Immunology (John Wiley & Sons. Inc, 2000, p. 15.1.1-15.1.20) was used.

Figure 2:
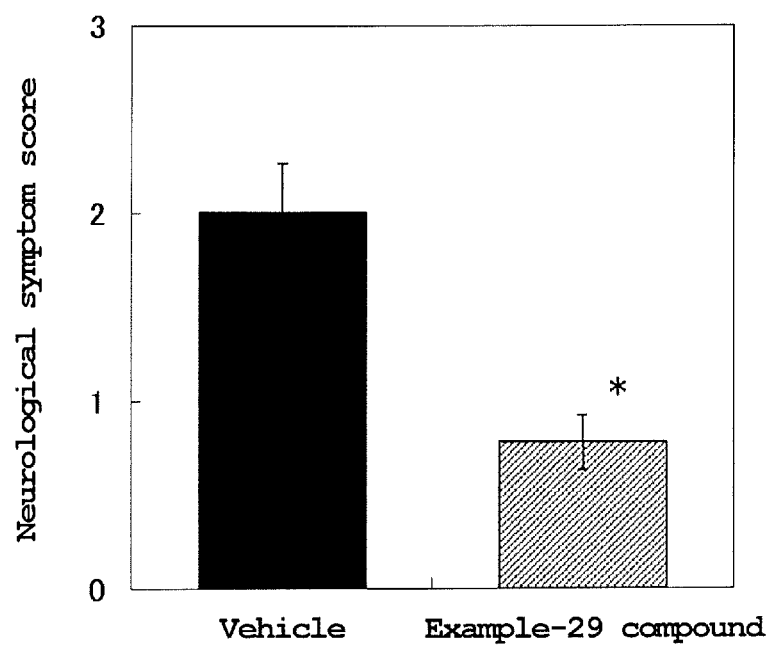
FIG. 2 is a graph showing the suppressive effect of the compound of Example 29 on the increase in neurological symptom score in a mouse experimental autoimmune encephalomyelitis model.
Figure 3:
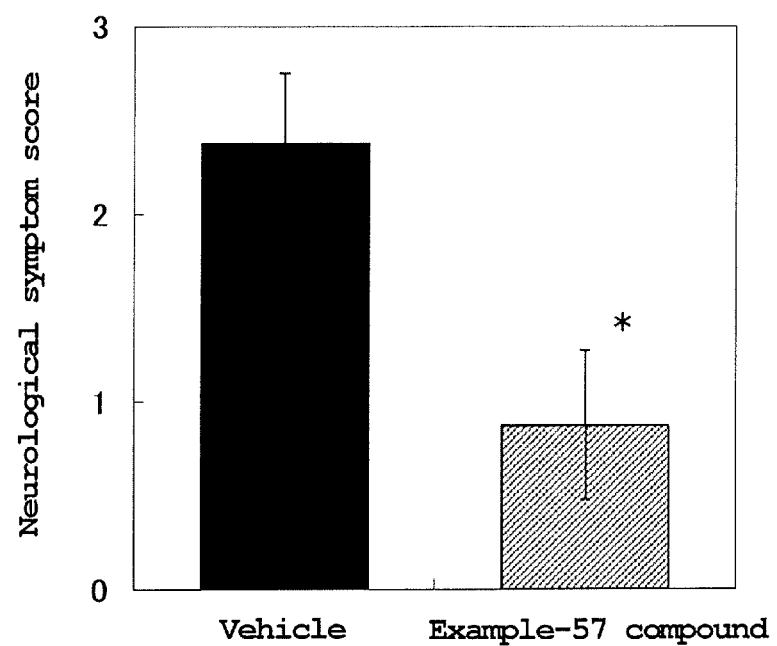
FIG. 3 is a graph showing the suppressive effect of the compound of Example 57 on the increase in the neurological symptom score in a mouse experimental autoimmune encephalomyelitis model.

The results are shown in FIGS. 1, 2 and 3. The vertical axis represents the neurological symptom score (mean±standard error, n=8 to 9). "Vehicle" on the horizontal axis represents the vehicle administration group, the "Example-20 compound" represents the Example-20 compound administration group, the "Example-29 compound" represents the Example-29 compound administration group, and the "Example-57 compound" represents the Example-57 compound administration group. FIG. 1 shows the neurological symptom score on the 13th day after inoculation of the MOG35-55 administration solution, FIG. 2 shows the neurological symptom score on the 23rd day after inoculation of the MOG35-55 administration solution, and FIG. 3 shows the neurological symptom score on the 30th day after inoculation of the MOG35-55 administration solution. The mark of asterisk (*) indicates statistical significance compared to the vehicle administration group (Wilcoxon test) (*: P<0.05).

Inoculation of the MOG35-55 administration solution increased the neurological symptom score in the vehicle administration group to 1.0 to 2.4. This increase in the neurological symptom score was statistically significantly suppressed by administration of the compound of Example 20, the compound of Example 29, or the compound of Example 57.

These results revealed that the cyclic amine derivative (I) or a pharmacologically acceptable salt thereof shows marked symptom suppressive effect on multiple sclerosis.

Example 74

Symptom Suppressive Effect on Imiquimod-Induced Mouse Psoriasis Model

Using increase in the ear thickness as an index of exacerbation of symptoms, the effect of the cyclic amine derivative (I) or a pharmacologically acceptable salt thereof in an imiquimod-induced mouse psoriasis model was evaluated. The imiquimod-induced mouse psoriasis model was prepared by a partially modified method by Schaper et al. (The Journal of Dermatological Science, 2013, Vol. 71, No. 1, p. 29-36).

BALB/c mice (male, 7 weeks old) (Charles River Laboratories Japan, Inc.) were used at 8 weeks old after preliminary breeding. To induce psoriasis-like symptoms, 5 mg each of BESELNA CREAM 5% was applied once daily to the outside of the right and left auricles of the mice for 8 days from the day of first administration of imiquimod (hereinafter referred to as induction day) to 7 days after induction (dose of imiquimod, 0.5 mg/body/day).

The test compound at a dose of 10 mg/kg was administered to the mice once daily for 5 days from 3 days after induction to 7 days after induction. As the test compound, the compound of Example 20, the compound of Example 29, and the compound of Example 57 were used. The compound of Example 20, the compound of Example 29, and the compound of Example 57 were suspended in a 0.5 w/v % methylcellulose solution and orally administered. The group in which the compound of Example 20 was administered to mice was defined as the Example-20 compound administration group, the group in which the compound of Example 29 was administered was defined as the Example-29 compound administration group, and the group in which the compound of Example 57 was administered was defined as the Example-57 compound administration group. In the vehicle administration group, a vehicle of each test compound (0.5 w/v % methylcellulose solution) was similarly administered.

The right and left ear thickness before administration of imiquimod (before induction) on the induction day and the right and left ear thickness on the 8th day after induction were measured with a digital micrometer (Mitutoyo Corporation). The mean of the right and left ear thickness was regarded as ear thickness, and the change in the ear thickness (ear thickness on the 8th day after induction−ear thickness before induction) was used as an index of the drug efficacy evaluation.

Figure 4:
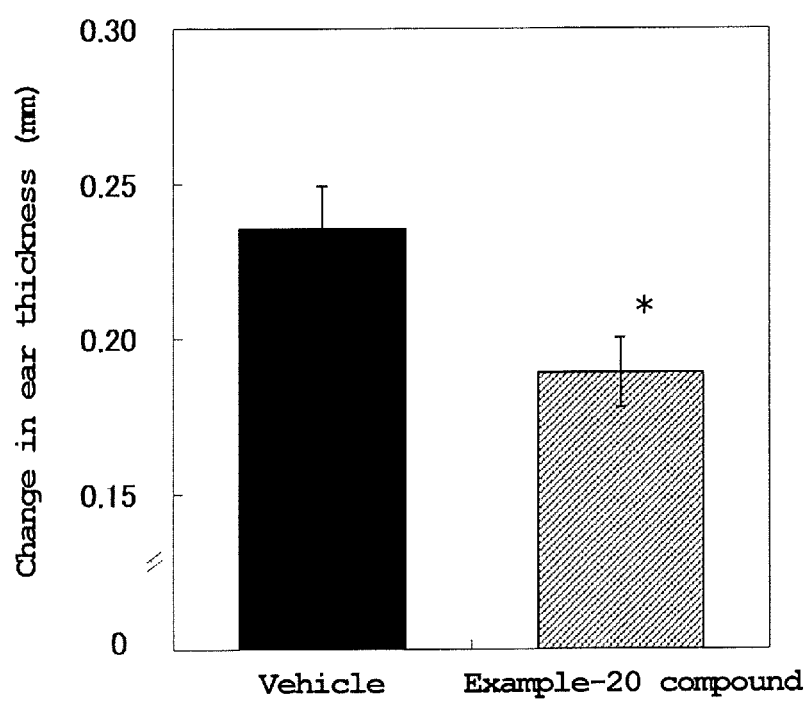
FIG. 4 is a graph showing the suppressive effect of the compound of Example 20 on the increase in ear thickness in an imiquimod-induced mouse psoriasis model.
Figure 5:
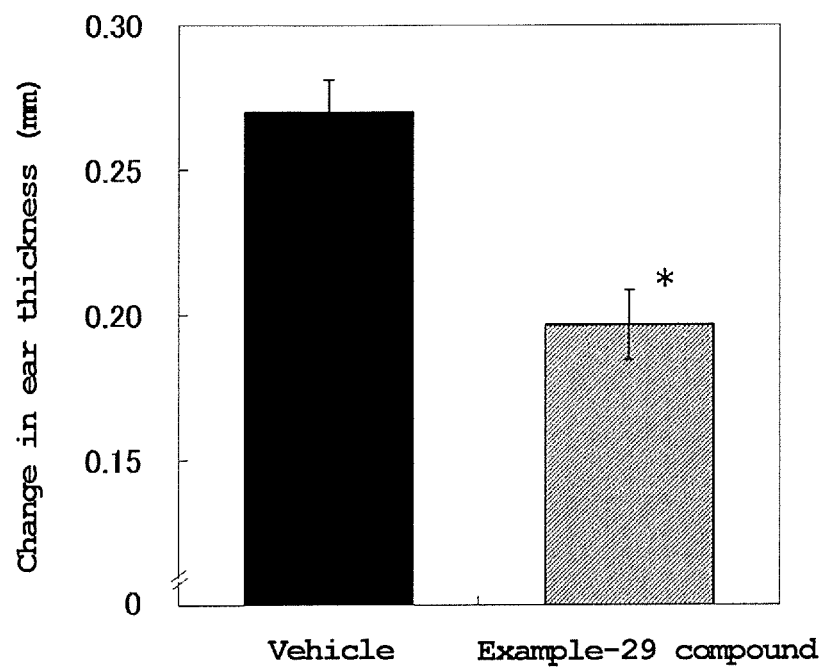
FIG. 5 is a graph showing the suppressive effect of the compound of Example 29 on the increase in ear thickness in an imiquimod-induced mouse psoriasis model.
Figure 6:
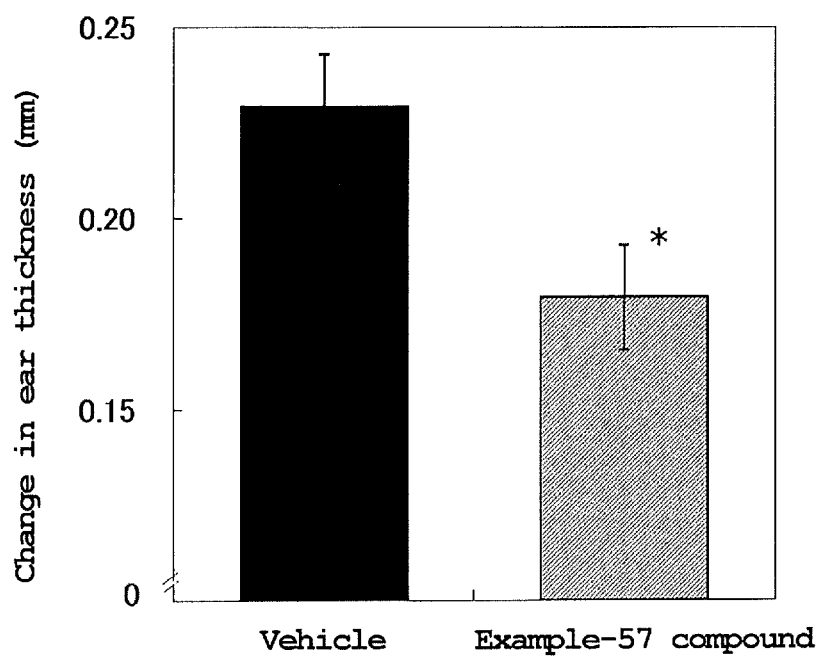
FIG. 6 is a graph showing the suppressive effect of the compound of Example 57 on the increase of ear thickness in an imiquimod-induced mouse psoriasis model.

The results are shown in FIGS. 4, 5, and 6. The vertical axis represents the change in the ear thickness (mm) (mean±standard error, n=6). "Vehicle" on the horizontal axis represents the vehicle administration group, the "Example-20 compound" represents the Example-20 compound administration group, the "Example-29 compound" represents the Example-29 compound administration group, and the "Example-57 compound" represents the Example-57 compound administration group. The mark of asterisk (*) indicates statistical significance compared to the vehicle administration group (Student's t-test) (*: P<0.05).

Induction by imiquimod increased the ear thickness on the 8th day after induction in the vehicle administration group by 0.23 mm to 0.27 mm compared to the ear thickness before induction. This increase in the ear thickness was statistically significantly suppressed by administration of the compound of Example 20, the compound of Example 29, or the compound of Example 57.

These results revealed that the cyclic amine derivative (I) or a pharmacologically acceptable salt thereof shows marked symptom suppressive effect on psoriasis.

Example 75

Symptom Suppressive Effect on DNFB-Induced Mouse Allergic Dermatitis Model

Using increase in the ear swelling rate as an index of exacerbation of symptoms, the effect of the cyclic amine derivative (I) or a pharmacologically acceptable salt thereof in a DNFB-induced mouse allergic dermatitis model was evaluated. The DNFB-induced mouse allergic dermatitis model was prepared by a partially modified method by Curzytek et al. (Pharmacological Reports, 2013, Vol. 65, p. 123'7-1246).

BALB/c mice (female, 6 weeks old) (Charles River Laboratories Japan, Inc.) were used at 7 weeks old after preliminary breeding. To the back of the mice, 25 µL of a 0.5 v/v % DNFB solution dissolved in acetone:olive oil (4:1) was applied. The next day, the same operation was repeated to sensitize the mice. Four days after the sensitization, 10 µL each of a 0.2 v/v % DNFB solution dissolved in acetone:olive oil (4:1) was applied to both sides of the right auricle of the sensitized mice to induce inflammation.

One hour before induction, the compound of Example 20, the compound of Example 29, or the compound of Example 57 was administered at a dose of 10 mg/kg to the mice. The compound of Example 20, the compound of Example 29, and the compound of Example 57 were suspended in a 0.5 w/v % methylcellulose solution and orally administered. The group in which the compound of Example 20 was administered to mice was defined as the Example-20 compound administration group, the group in which the compound of Example 29 was administered was defined as the Example-29 compound administration group, and the group in which the compound of Example 57 was administered was defined as the Example-57 compound administration group. In the vehicle administration group, a vehicle of each test compound (0.5 w/v % methylcellulose solution) was similarly administered.

The right ear thickness before application of the DNFB solution (before induction) on the induction day and the right ear thickness at the 24th hour after induction were measured with a digital micrometer (Mitutoyo Corporation). The swelling rate of the auricle was calculated by Formula 3 and used as an index of the drug efficacy evaluation.

Ear swelling rate(%)=((Right ear thickness at the 24th hour after induction)−(Right ear thickness before induction))/Right ear thickness before induction×100     Formula 3

Figure 7:
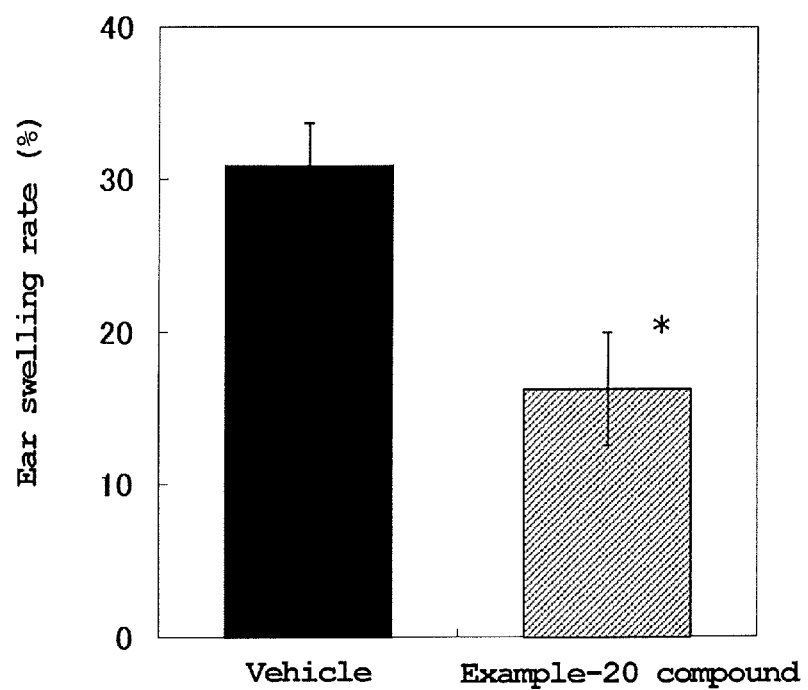
FIG. 7 is a graph showing the suppressive effect of the compound of Example 20 on the increase in ear swelling rate in a dinitrofluorobenzene-induced mouse allergic dermatitis model.
Figure 8:
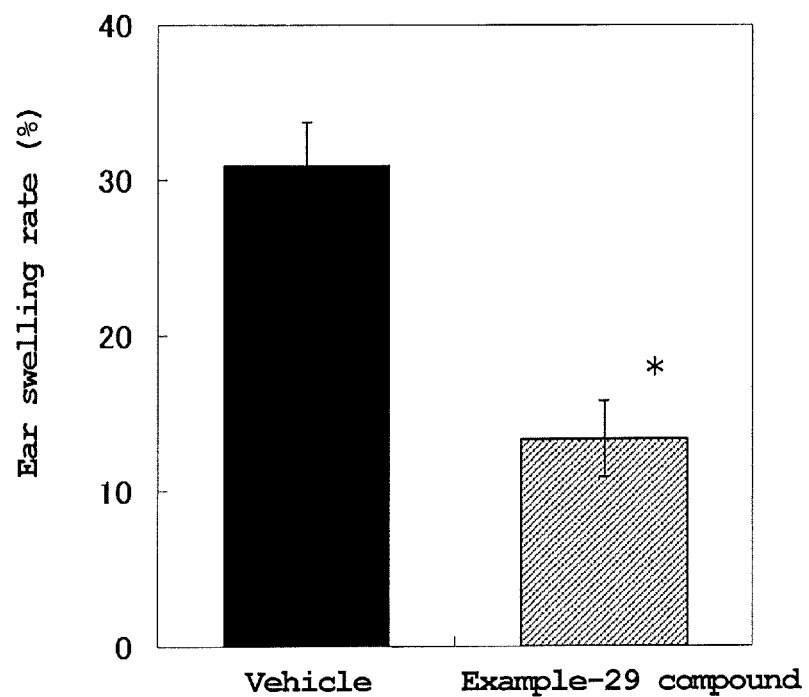
FIG. 8 is a graph showing the suppressive effect of the compound of Example 29 on the increase in ear swelling rate in a dinitrofluorobenzene-induced mouse allergic dermatitis model.
Figure 9:
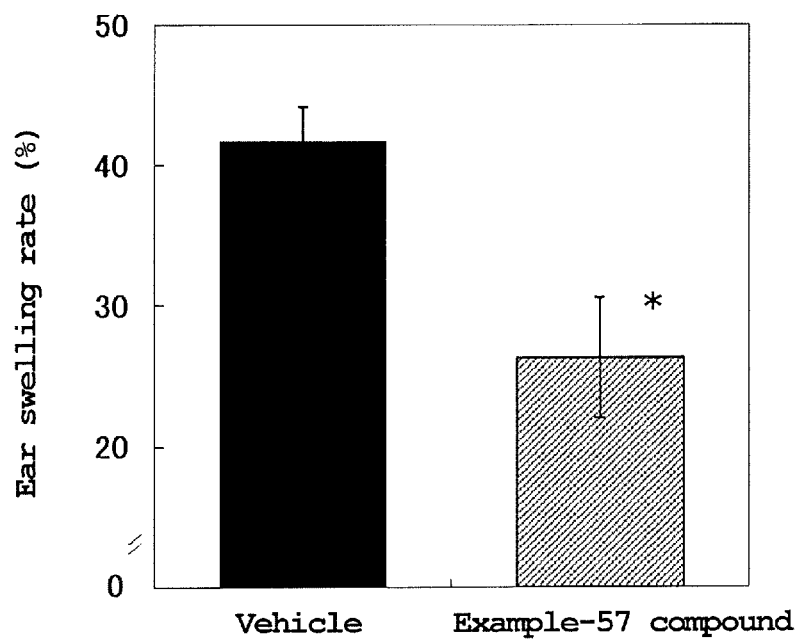
FIG. 9 is a graph showing the suppressive effect of the compound of Example 57 on the increase in ear swelling rate in a dinitrofluorobenzene-induced mouse allergic dermatitis model.

The results are shown in FIGS. 7, 8, and 9. The vertical axis represents the ear swelling rate (%) (mean±standard error, n=6 to 8). "Vehicle" on the horizontal axis represents the vehicle administration group, the "Example-20 compound" represents the Example-20 compound administration group, the "Example-29 compound" represents the Example-29 compound administration group, and the "Example-57 compound" represents the Example-57 compound administration group. The mark of asterisk (*) indicates statistical significance compared to the vehicle administration group (Student's t-test) (*: P<0.05).

Application of the DNFB solution to the auricle increased the ear swelling rate in the vehicle administration group by 30.9% to 41.7%. This increase in the ear swelling rate was statistically significantly suppressed by administration of the compound of Example 20, the compound of Example 29, or the compound of Example 57.

This result revealed that the cyclic amine derivative (I) or a pharmacologically acceptable salt thereof shows marked symptom suppressive effect on allergic dermatitis, particularly contact dermatitis.

Example 76

Symptom Suppressive Effect on Oxazolone-Induced Mouse Atopic Dermatitis Model

Using increase in the ear thickness as an index of exacerbation of symptoms, the effect of the cyclic amine derivative (I) or a pharmacologically acceptable salt thereof in an oxazolone-induced mouse atopic dermatitis model was evaluated. The oxazolone-induced mouse atopic dermatitis model was prepared by a partially modified method by Nakajima et al. (Journal of Investigative Dermatology, 2014, Vol. 134, p. 2122-2130).

BALB/c mice (female, 7 weeks old) (Charles River Laboratories Japan, Inc.) were used at 8 or 9 weeks old after preliminary breeding. To the back of the mice, 25 µL of a 3 w/v % oxazolone solution dissolved in ethanol was applied to sensitize the mice. Every other day from 5 days to 13 days after the sensitization, 10 µL each of a 0.6 w/v % oxazolone solution dissolved in ethanol was applied to both sides of the right auricle of the sensitized mice to induce inflammation.

The test compound at a dose of 10 mg/kg was administered to the mice once daily for 15 days from the sensitization day to 14 days after sensitization. As the test compound, the compound of Example 20, the compound of Example 29, and the compound of Example 57 were used. The compound of Example 20, the compound of Example 29, and the compound of Example 57 were suspended in a 0.5 w/v % methylcellulose solution and orally administered. The group in which the compound of Example 20 was administered to mice was defined as the Example-20 compound administration group, the group in which the compound of Example 29 was administered was defined as the Example-29 compound administration group, and the group in which the compound of Example 57 was administered was defined as the Example-57 compound administration group. In the vehicle administration group, a vehicle of each test compound (0.5 w/v % methylcellulose solution) was similarly administered.

The right ear thickness before application of the oxazolone solution (before sensitization) on the sensitization day and the right ear thickness on the next day of final induction were measured with a digital micrometer (Mitutoyo Corporation). The change in the ear thickness (right ear thickness on the next day of final induction—right ear thickness before sensitization) was used as an index of the drug efficacy evaluation.

Figure 10:
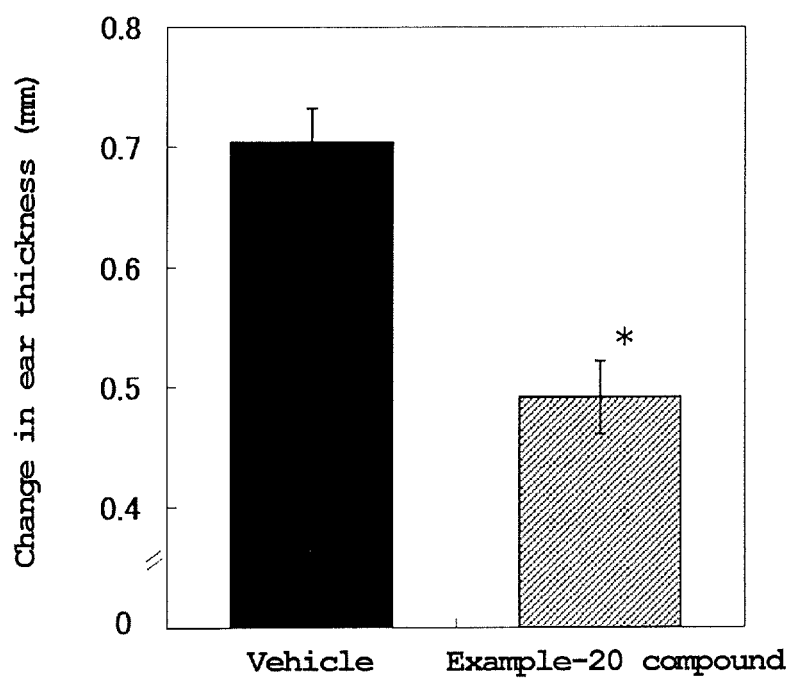
FIG. 10 is a graph showing the suppressive effect of the compound of Example 20 on the increase in ear thickness in an oxazolone-induced mouse atopic dermatitis model.
Figure 11:
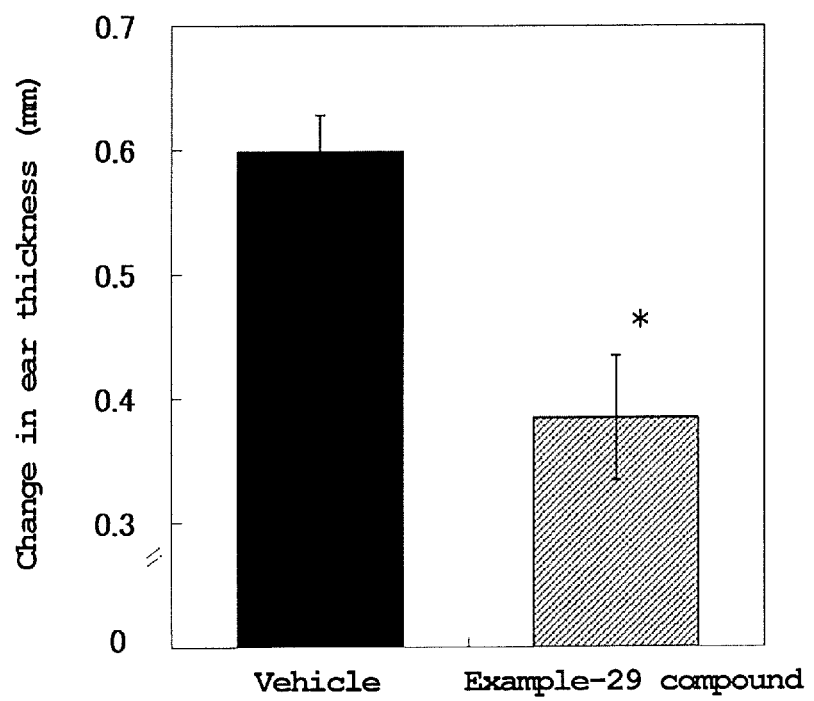
FIG. 11 is a graph showing the suppressive effect of the compound of Example 29 on the increase in ear thickness in an oxazolone-induced mouse atopic dermatitis model.
Figure 12:
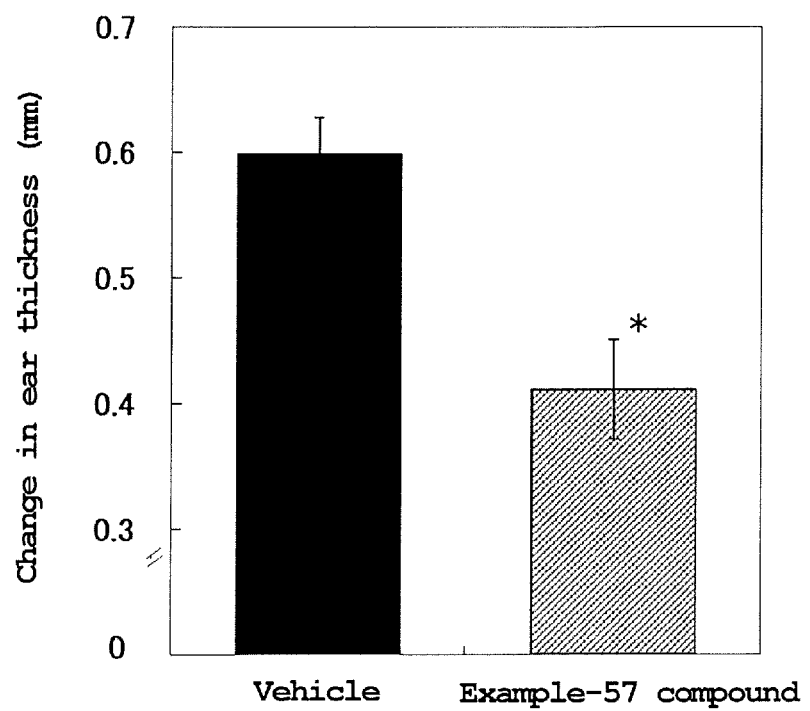
FIG. 12 is a graph showing the suppressive effect of the compound of Example 57 on the increase in ear thickness in an oxazolone-induced mouse atopic dermatitis model.

The results are shown in FIGS. 10, 11, and 12. The vertical axis represents the change in the ear thickness (mm) (mean±standard error, n=7). "Vehicle" on the horizontal axis represents the vehicle administration group, the "Example-20 compound" represents the Example-20 compound administration group, the "Example-29 compound" represents the Example-29 compound administration group, and the "Example-57 compound" represents the Example-57 compound administration group. The mark of asterisk (*) indicates statistical significance compared to the vehicle administration group (Student's t-test) (*: P<0.05).

Application of the oxazolone solution to the auricle increased the ear thickness on the next day of final induction in the vehicle administration group by 0.60 mm to 0.70 mm compared to the ear thickness before sensitization. This increase in the ear thickness was statistically significantly suppressed by administration of the compound of Example 20, the compound of Example 29, or the compound of Example 57.

This result revealed that the cyclic amine derivative (I) or a pharmacologically acceptable salt thereof shows marked symptom suppressive effect on allergic dermatitis, particularly atopic dermatitis.

INDUSTRIAL APPLICABILITY

Since the cyclic amine derivative or a pharmacologically acceptable salt thereof has excellent RORγ antagonist activity, it can be used as a medicament for diseases in which improvement in the pathological state or remission of symptoms can be expected by suppression of the function of RORγ. Particularly, the cyclic amine derivative or a pharmacologically acceptable salt thereof can be used as a therapeutic agent or preventive agent for autoimmune diseases such as multiple sclerosis or psoriasis, or allergic diseases, including allergic dermatitis or the like such as contact dermatitis or atopic dermatitis.

The invention claimed is:

1. A cyclic amine derivative represented by formula (I):

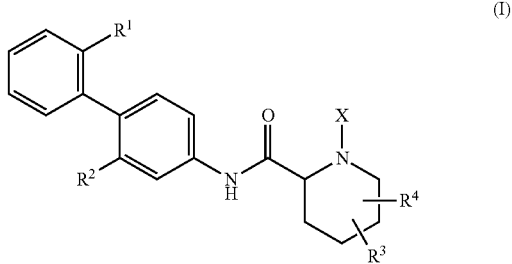

wherein
R¹ represents an alkyloxy group having 1 to 3 carbon atoms, any 1 to 3 hydrogen atoms of which are optionally substituted with a halogen atom(s);
R² represents a halogen atom;
R³ represents a hydrogen atom, a halogen atom, or a hydroxy group;
R⁴ represents a hydrogen atom or a halogen atom;
X represents —C(=O)—(CH$_2$)$_n$—R⁵ or —S(=O)$_2$—R⁶;
n is an integer of 0 to 5;
R⁵ represents a hydrogen atom, —OR⁷, —SR⁷, —S(=O)$_2$—R⁷, —C(=O)—OR⁷, —N(R⁷)R⁸, an alkyl group having 1 to 3 carbon atoms, any 1 to 3 hydrogen atoms of which are optionally substituted with a halogen atom(s), or a heteroaryl group, any hydrogen atom(s) of which is/are optionally substituted with an alkyl group(s) having 1 to 3 carbon atoms;
R⁶ represents an alkyl group having 1 to 5 carbon atoms;
R⁷ represents a hydrogen atom or an alkyl group having 1 to 3 carbon atoms, any 1 to 3 hydrogen atoms of which are optionally substituted with a halogen atom(s); and
R⁸ represents a hydrogen atom, an alkyl group having 1 to 3 carbon atoms, an acyl group having 2 to 4 carbon atoms, or an alkylsulfonyl group having 1 to 3 carbon atoms,
or a pharmacologically acceptable salt thereof.

2. The cyclic amine derivative according to claim 1, wherein:
R¹ is an alkyloxy group having 1 to 3 carbon atoms, any 1 to 3 hydrogen atoms of which are optionally substituted with a fluorine atom(s) or a chlorine atom(s);
R² is a fluorine atom or a chlorine atom;
R³ is a hydrogen atom, a fluorine atom, a chlorine atom, or a hydroxy group;
R⁴ is a hydrogen atom, a fluorine atom, or a chlorine atom;
R⁵ is a hydrogen atom, —OR⁷, —SR⁷, —S(=O)$_2$—R⁷, —C(=O)—OR⁷, —N(R⁷)R⁸, an alkyl group having 1 to 3 carbon atoms, any 1 to 3 hydrogen atoms of which are optionally substituted with a fluorine atom(s) or a chlorine atom(s), or a heteroaryl group, any hydrogen atom(s) of which is/are optionally substituted with a methyl group(s);
R⁶ is an alkyl group having 1 to 3 carbon atoms; and
R⁷ is a hydrogen atom or an alkyl group having 1 to 3 carbon atoms, any 1 to 3 hydrogen atoms of which are optionally substituted with a fluorine atom(s) or a chlorine atom(s),
or a pharmacologically acceptable salt thereof.

3. The cyclic amine derivative according to claim 1, wherein:
R¹ is a methoxy group, any 1 to 3 hydrogen atoms of which are optionally substituted with a fluorine atom(s);
R² is a fluorine atom or a chlorine atom;
R³ is a hydrogen atom, a fluorine atom, or a hydroxy group;
R⁴ is a hydrogen atom or a fluorine atom;
n is an integer of 0 to 4;
R⁵ is a hydrogen atom, —OR⁷, —N(R⁷)R⁸, an alkyl group having 1 to 3 carbon atoms, any 1 to 3 hydrogen atoms of which are optionally substituted with a fluorine atom(s), or a 5-membered ring heteroaryl group, any hydrogen atom(s) of which is/are optionally substituted with a methyl group(s);
R⁶ is a methyl group or an ethyl group;
R⁷ is a hydrogen atom or an alkyl group having 1 to 3 carbon atoms, any 1 to 3 hydrogen atoms of which are optionally substituted with a fluorine atom(s); and
R⁸ is a hydrogen atom, a methyl group, an acyl group having 2 to 4 carbon atoms, or an alkylsulfonyl group having 1 to 3 carbon atoms,
or a pharmacologically acceptable salt thereof.

4. The cyclic amine derivative according to claim 1, wherein:
R¹ is a trifluoromethoxy group;
R² is a chlorine atom;
R³ is a hydrogen atom;
R⁴ is a hydrogen atom;
X is —C(=O)—(CH$_2$)$_n$—R⁵;
n is an integer of 0 to 3;
R⁵ is a methyl group, a trifluoromethyl group, —N(R⁷)R⁸, or an imidazolyl, triazolyl, or tetrazolyl group, any hydrogen atom(s) of which is/are optionally substituted with a methyl group(s);
R⁷ is a hydrogen atom, a methyl group, or an ethyl group; and
R⁸ is a hydrogen atom, a methyl group, an acetyl group, a propionyl group, a methylsulfonyl group, or an ethylsulfonyl group,
or a pharmacologically acceptable salt thereof.

5. A medicament comprising the cyclic amine derivative according to claim 1 or a pharmacologically acceptable salt thereof as an active ingredient.

6. A retinoid-related orphan receptor γ antagonist comprising the cyclic amine derivative according to claim 1 or a pharmacologically acceptable salt thereof as an active ingredient.

7. A therapeutic agent for an autoimmune disease comprising the cyclic amine derivative according to claim 1 or a pharmacologically acceptable salt thereof as an active ingredient.

8. A therapeutic agent for multiple sclerosis or psoriasis comprising the cyclic amine derivative according to claim 1 or a pharmacologically acceptable salt thereof as an active ingredient.

9. A therapeutic agent for an allergic disease comprising the cyclic amine derivative according to claim 1 or a pharmacologically acceptable salt thereof as an active ingredient.

10. A therapeutic agent for allergic dermatitis comprising the cyclic amine derivative according to claim 1 or a pharmacologically acceptable salt thereof as an active ingredient.

11. A therapeutic agent for contact dermatitis or atopic dermatitis comprising the cyclic amine derivative according to claim 1 or a pharmacologically acceptable salt thereof as an active ingredient.

* * * * *